(12) United States Patent
Gartner et al.

(10) Patent No.: US 12,077,826 B2
(45) Date of Patent: Sep. 3, 2024

(54) LIPID-MODIFIED OLIGONUCLEOTIDES AND METHODS OF USING THE SAME

(71) Applicant: The Regents of The University of California, Oakland, CA (US)

(72) Inventors: Zev J. Gartner, San Francisco, CA (US); David Patterson, San Francisco, CA (US); Eric D. Chow, San Francisco, CA (US); Robert Weber, San Francisco, CA (US); Christopher McGinnis, San Francisco, CA (US)

(73) Assignee: The Regents of The University of California

( * ) Notice: Subject to any disclaimer, the term of this patent is extended or adjusted under 35 U.S.C. 154(b) by 564 days.

(21) Appl. No.: 17/258,420

(22) PCT Filed: Jul. 8, 2019

(86) PCT No.: PCT/US2019/040898
§ 371 (c)(1),
(2) Date: Jan. 6, 2021

(87) PCT Pub. No.: WO2020/010366
PCT Pub. Date: Jan. 9, 2020

(65) Prior Publication Data
US 2021/0388447 A1    Dec. 16, 2021

Related U.S. Application Data

(60) Provisional application No. 62/694,970, filed on Jul. 6, 2018, provisional application No. 62/847,916, filed on May 14, 2019.

(51) Int. Cl.
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *C12Q 2600/158* (2013.01)

(58) Field of Classification Search
CPC ............ C12Q 1/6886; C12Q 2600/158; C12Q 1/6869; C12Q 2521/107; C12Q 2563/107; C12Q 2563/159; C12Q 2563/179; C12Q 2565/629; C12Q 2535/122
See application file for complete search history.

(56) References Cited

U.S. PATENT DOCUMENTS

| | | | |
|---|---|---|---|
| 6,812,339 | B1 | 11/2004 | Venter et al. |
| 9,650,407 | B2 | 5/2017 | Gartner et al. |
| 2010/0317714 | A1 | 12/2010 | Xi et al. |
| 2012/0142088 | A1 | 6/2012 | Hsiao et al. |
| 2016/0257993 | A1 | 9/2016 | Fu et al. |
| 2017/0305955 | A1 | 10/2017 | Gartner et al. |
| 2018/0037885 | A1 | 2/2018 | Lebofsky et al. |

FOREIGN PATENT DOCUMENTS

| | | |
|---|---|---|
| CN | 107674920 | 2/2018 |
| WO | WO 2014071388 | 5/2014 |
| WO | WO 2016040476 | 3/2016 |
| WO | WO-2018/022581 A1 | 2/2018 |

OTHER PUBLICATIONS

Raouane et al., 2012, Bioconjugate Chemistry, 23, 1091-1104 (Year: 2012).*
McGinnis et al, Multi-seq: sample multiplexing for single-cell RNA sequencing using lipid-tagged indices, Nature Methods, vol. 16, Jul. 2019, 619-626. (Post Art) (Year: 2019).*
Marlon Stoeckius et al. "Simultaneous epitope and transcriptome measurement in single cells", Published online Jul. 31, 2017; doi: 10.1038/nmeth.4380, Nature Methods, pp. 1-10.
Robert J. Weber et al. "Efficient Targeting of Fatty-Acid Modified Oligonucleotides to Live Cell Membranes through Stepwise Assembly" dx.doi.org/10.1021/bm501467h | Biomacromolecules 2014, 15, pp. 4621-4626.
Chinese Office Action 201980058374.X, Issued Nov. 3, 2022.
European Search Report for EP Application No. 19831435.3 dated Mar. 23, 2022.
Ramsköld, D., et al., Full-length mRNA-seq from single cell levels of RNA and individual circulating tumor cells, Nat. Biotechnol., 2012, 30(8):777-782.
Hashimshony, T., et al., CEL-Seq: single-cell RNA-Seq by multiplexed linear amplification, Cell Rep., 2012, 2(3):666-673.
Gierahn, T. M., et al., Seq-Well: portable, low-cost RNA sequencing of single cells at high throughput, Nat. Methods, 2017, 14(4):395-398.
Cao, J., et al., Comprehensive single-cell transcriptional profiling of a multicellular organism, Science. 2017, 357(6352):661-667.

(Continued)

*Primary Examiner* — Narayan K Bhat
(74) *Attorney, Agent, or Firm* — The Regents of the University of California

(57) ABSTRACT

Disclosed are compositions comprising a first lipid-conjugated oligonucleotide comprising a first lipid moiety, a first hybridization region, and a first primer region; a second lipid-conjugated oligonucleotide comprising a second hybridization region and a second lipid moiety, wherein the second hybridization region is the reverse complement of the first hybridization region; and a third oligonucleotide comprising a second primer region, a barcode region, and a capture sequence, wherein the second primer region is the reverse complement of the first primer region; compositions comprising a lipid-conjugated DNA oligonucleotide comprising a lipid moiety, a barcode region, and a capture sequence; and composition comprising a first lipid-conjugated DNA oligonucleotide comprising a lipid moiety and a first primer region; and a second DNA oligonucleotide comprising a second primer region, a barcode region, and a capture sequence, wherein the second primer region is the reverse complement of the first primer region. Also disclosed are membranes and cells comprising such compositions and uses of such compositions.

18 Claims, 41 Drawing Sheets
Specification includes a Sequence Listing.

(56) References Cited

OTHER PUBLICATIONS

Rosenberg, A. B., et al., Single-cell profiling of the developing mouse brain and spinal cord with split-pool barcoding, Science, 2018, 360(6385):176-182.

Macosko, E. Z., et al., Highly parallel genome-wide expression profiling of individual cells using nanoliter droplets, Cell, 2015, 161(5):1202-1214.

Klein, A. M., et al., Droplet barcoding for single-cell transcriptomics applied to embryonic stem cells, Cell, 2015, 161(5):1187-1201.

Zheng, G. X., et al., Massively parallel digital transcriptional profiling of single cells, Nat. Commun., 2017, 8:14049.

Habib, N., et al., Massively parallel single-nucleus RNA-seq with DroNc-seq, Nat. Methods, 2017, 14(10):955-958.

Tabula Muris Consortium, Single-cell transcriptomic characterization of 20 organs and tissues from individual mice creates a *Tabula Muris*, Nature, 2018, 562(7727):367-372.

Regev, A., et al., The human cell atlas, eLife, 2017, 6:e27041.

Wagner, D. E., et al., Single-cell mapping of gene expression landscapes and lineage in the zebrafish embryo, Science, 2018, 360(6392):981-987.

Ordovas-Montanes, J., et al., Allergic inflammatory memory in human respiratory epithelial progenitor cells, Nature, 2018, 560(7720):649-654.

Kang, H. M., et al., Multiplexed droplet single-cell RNA-sequencing using natural genetic variation, Nat. Biotechnol., 2018, 36(1):89-94.

Dixit, A., et al., Perturb-seq: Dissecting molecular circuits with scalable single-cell rna profiling of pooled genetic screens, Cell, 2016, 167(7):1853-1866.

Adamson, B., et al., A multiplexed single-cell CRISPR screening platform enables systematic dissection of the unfolded protein response, Cell, 2016, 167(7):1867-1882.

Jaitin, D. A., et al., Dissecting immune circuits by linking CRISPR-pooled screens with single-cell RNA-seq, Cell, 2016, 167(7):1883-1896.

Aarts, M., et al., Coupling shRNA screens with single-cell RNA-seq identifies a dual role for mTOR in reprogramming-induced senescence, Genes Dev., 2017, 31(20):2085-2098.

Shin, D., et al., Multiplexed single-cell RNA-seq via transient barcoding for drug screening, 2018, Preprint bioRxiv, doi: https://doi.org/10.1101/359851.

Guo, C., et al., CellTag indexing: A genetic barcode-based multiplexing tool for single-cell technologies, 2019, Preprint bioRxiv, doi: http://dx.doi.org/10.1101/335547.

Stoeckius, M., et al., Cell Hashing with barcoded antibodies enables multiplexing and doublet detection for single cell genomics, Genome Biol., 2018, 19:224.

Gehring, J., et al., Highly multiplexed single-cell rna-seq for defining cell population and transcriptional spaces, 2018, Preprint bioRxiv, doi: https://doi.org/10.1101/315333.

Gaublomme, J. T., et al., Nuclei multiplexing with barcoded antibodies for single-nucleus genomics, 2018, Preprint bioRxiv, doi: https://doi.org/10.1101/476036.

Weber, R. J., et al., Efficient targeting of fatty-acid modified oligonucleotides to live cell membranes through stepwise assembly, Biomacromolecules, 2014, 15(12):4621-4626.

Wu, H., et al., Advantages of single-nucleus over single-cell RNA sequencing of adult kidney: Rare cell types and novel cell states revealed in fibrosis, J. Am. Soc. Nephrol., 2019, 30(1):23-32.

Coutelier, J. P., et al., Binding and functional effects of thyroid stimulating hormone on human immune cells, J. Clin. Immunol., 1990, 10(4): 204-210 (Abstract only).

Jeffrey, K. L., et al., Positive regulation of immune cell function and inflammatory responses by phosphatase PAC-1, Nat. Immunol., 2006, 7(3):274-283.

Ziegler, S. F., et al., The activation antigen CD69, Stem Cells, 1994, 12(5):456-465 (Abstract only).

Lieberman, J., et al., Nuclear war: The granzyme A-bomb, Curr. Opin. Immunol., 2003, 15(5):553-559 (Abstract only).

Garbe, J. C., et al., Molecular distinctions between stasis and telomere attrition senescence barriers shown by long-term culture of normal human mammary epithelial cells, Cancer Res., 2009, 69(19):7557-7568.

Brisken, C., Progesterone signalling in breast cancer: a neglected hormone coming into the limelight, Nat. Rev. Cancer, 2013, 13(6):385-396.

Mcginnis, C. S., et al., DoubletFinder: Doublet detection in single-cell RNA sequencing data using artificial nearest neighbors, 2019, Cell Systems, 2019, 8(4):329-337.

Wolock, S. L., et al., Scrublet: Computational identification of cell doublets in single-cell transcriptomic data, Cell Systems, 2019, 8(4):281-291.

Chitale, D., et al., An integrated genomic analysis of lung cancer reveals loss of DUSP4 in EGFR-mutant tumors, Oncogene, 2009, 28(31):2773-2783.

Fearon, A. E., et al., PHLDA1 mediates drug resistance in receptor tyrosine kinase-driven cancer, Cell Rep., 2018, 22(9):2469-2481.

Savage, P., Blanchet-Cohen A, Revil T, et al. A targetable EGFR-dependent tumor-initiating program in breast cancer, Cell Rep., 2017, 21(5):1140-1149.

DeRose, Y. S., et al., Tumor grafts derived from women with breast cancer authentically reflect tumor pathology, growth, metastasis and disease outcomes, Nat. Med., 2011, 17(11):1514-1520.

Jiang, K., et al., RNA sequencing from human neutrophils reveals distinct transcriptional differences associated with chronic inflammatory states, BMC Med. Genomics, 2015, 8:55.

Lun, A. T. L., et al., EmptyDrops: Distinguishing cells from empty droplets in droplet-based single-cell RNA sequencing data, Genome Biol., 2019, 20:63.

Reyfman, P. A., et al., Single-cell transcriptomic analysis of human lung provides insights into the pathobiology of pulmonary fibrosis, Am. J. Respir. Crit. Care Med., 2019, 199(12): 1517-1536.

Jablonska, J., et al., The regulation of pre-metastatic niche formation by neutrophils, Oncotarget, 2017, 8(67):112132-112144.

Sharma, S. K et al., Pulmonary alveolar macrophages contribute to the premetastatic niche by suppressing antitumor T cell responses in the lungs, J. Immunol., 2015, 194(11):5529-5538.

Condamine, T., et al., Regulation of tumor metastasis by myeloid-derived suppressor cells, Annu. Rev. Med., 2015, 66:97-110.

Kitamura, T., et al., Monocytes differentiate to immune suppressive precursors of metastasis-associated macrophages in mouse models of metastatic breast cancer, Front. Immunol., 2018, 8:2004.

Catena, R., et al., Bone marrow-derived Gr1+ cells can generate a metastasis-resistant microenvironment via induced secretion of thrombospondin-1, Cancer Discov., 2013, 3(5):578-589.

Ouzounova, M., et al., Monocytic and granulocytic myeloid derived suppressor cells differentially regulate spatiotemporal tumour plasticity during metastatic cascade, Nat. Commun., 2017; 8:14979.

Nabavi, S., et al., EMDomics: A robust and powerful method for the identification of genes differentially expressed between heterogeneous classes, Bioinformatics, 2016, 32(4):533-541.

Subramanian, A., et al., A next generation connectivity map: L1000 platform and the first 1,000,000 profiles, Cell, 2017, 171(6):1437-1452.e17.

Ye, C., et al., Drug-seq for miniaturized high-throughput transcriptome profiling in drug discovery, Nat. Commun., 2018, 9(1):4307.

Romero, J. M., et al., Coordinated downregulation of the antigen presentation machinery and HLA class I/$\beta$2-microglobulin complex is responsible for HLA-ABC loss in bladder cancer, Int. J. Cancer, 2005, 113(4):605-610.

Stoeckius, M., et al., Simultaneous epitope and transcriptome measurement in single cells, Nat. Methods, 2017, 14(9):865-868.

Lim, E., et al., Aberrant luminal progenitors as the candidate target population for basal tumor development in BRCA1 mutation carriers, Nat. Med., 2009, 15(8):907-913.

Lawson, D. A., et al., Single-cell analysis reveals a stem-cell program in human metastatic breast cancer cells, Nature, 2015, 526(7571):131-135.

Satija, R., et al., Spatial reconstruction of single-cell gene expression data, Nat. Biotechnol., 2015, 33(5):495-502.

(56) References Cited

OTHER PUBLICATIONS

Butler, A., et al., Integrating single-cell transcriptomic data across different conditions, technologies, and species, Nat. Biotechnol., 2018, 36(5):411-420.
Van der Maaten, L. J. P., Accelerating t-SNE using tree-based algorithms, Journal of Machine Learning Research, 2014, 15:3221-3245.
McDavid, A., et al., Data exploration, quality control and testing in single-cell qPCR-based gene expression experiments, Bioinformatics, 2013. 29(4):461-467.
Morgan, M., et al., ShortRead: A Bioconductor package for input, quality assessment and exploration of high-throughput sequence data, Bioinformatics, 2009, 25(19):2607-2608.
Van der Loo, M. P. J., The stringdist package for approximate string matching, The R Journal, 2014, 6:111-122.
McGinnis, C. S., et al., Multi-seq: Sample multiplexing for single-cell RNA sequencing using lipid-tagged indices, Nature Methods, 2019, 16(7):619-626.
International Search Report and Written Opinion of the International Searching Authority for PCT/US2019/040898 Mailed Nov. 11, 2019.
International Preliminary Report on Patentability for PCT/US2019/040898 Issued Jan. 12, 2021.

* cited by examiner

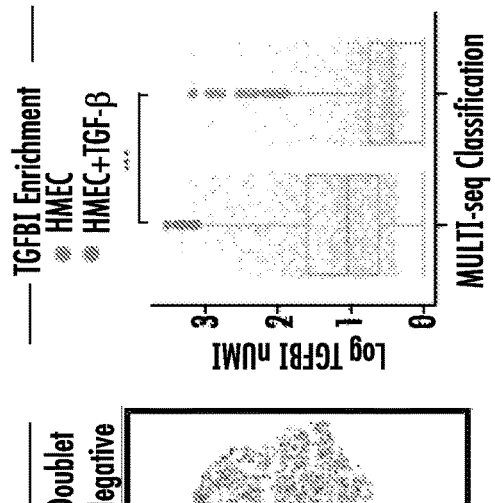
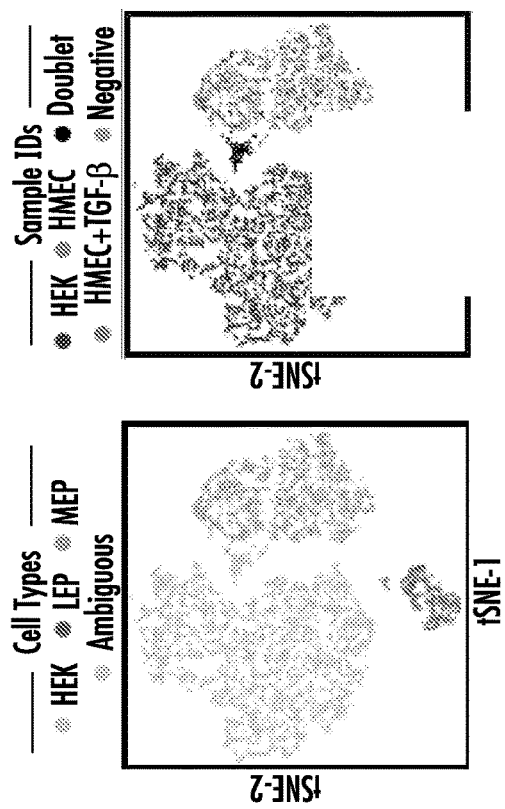
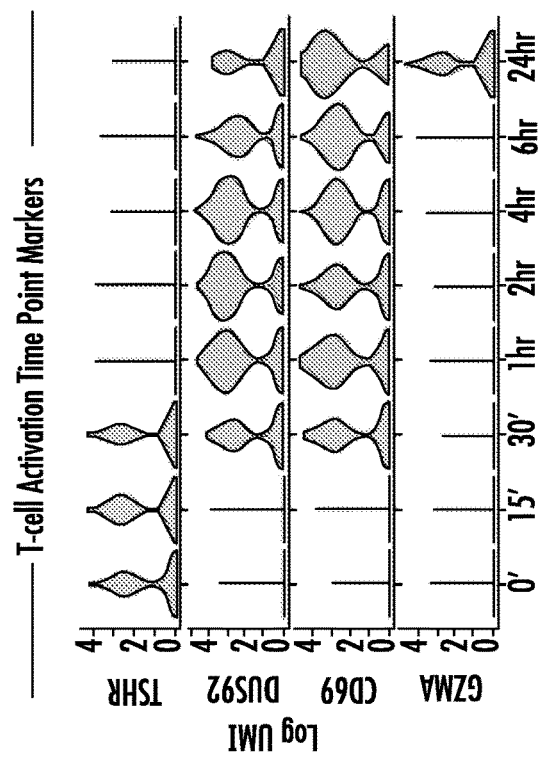
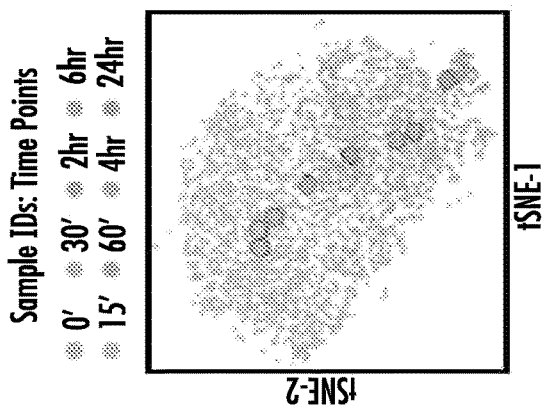
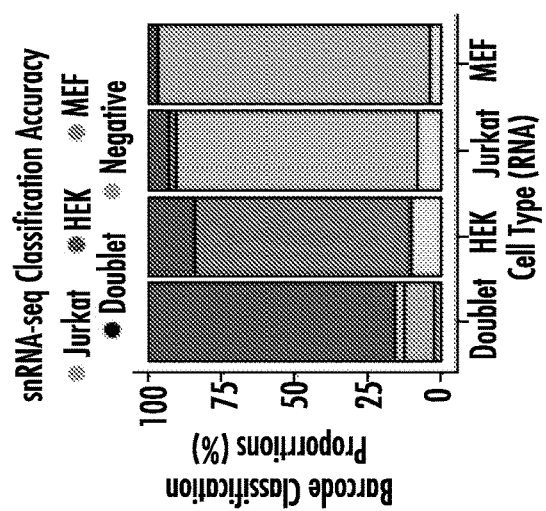

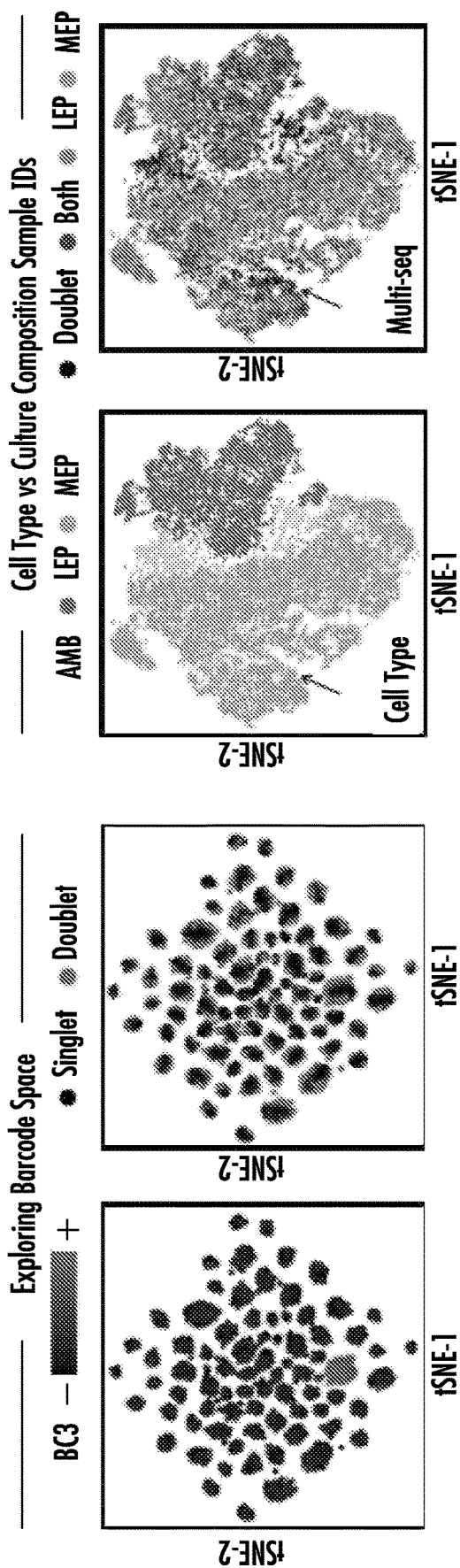
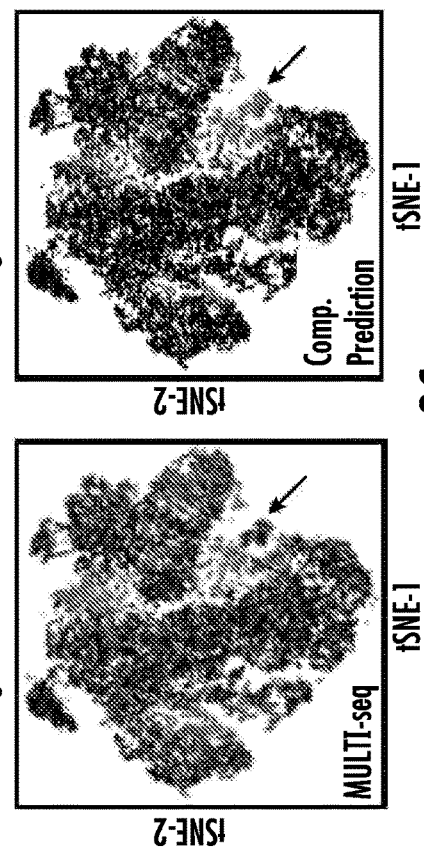
FIG. 9A
FIG. 9B
FIG. 9C

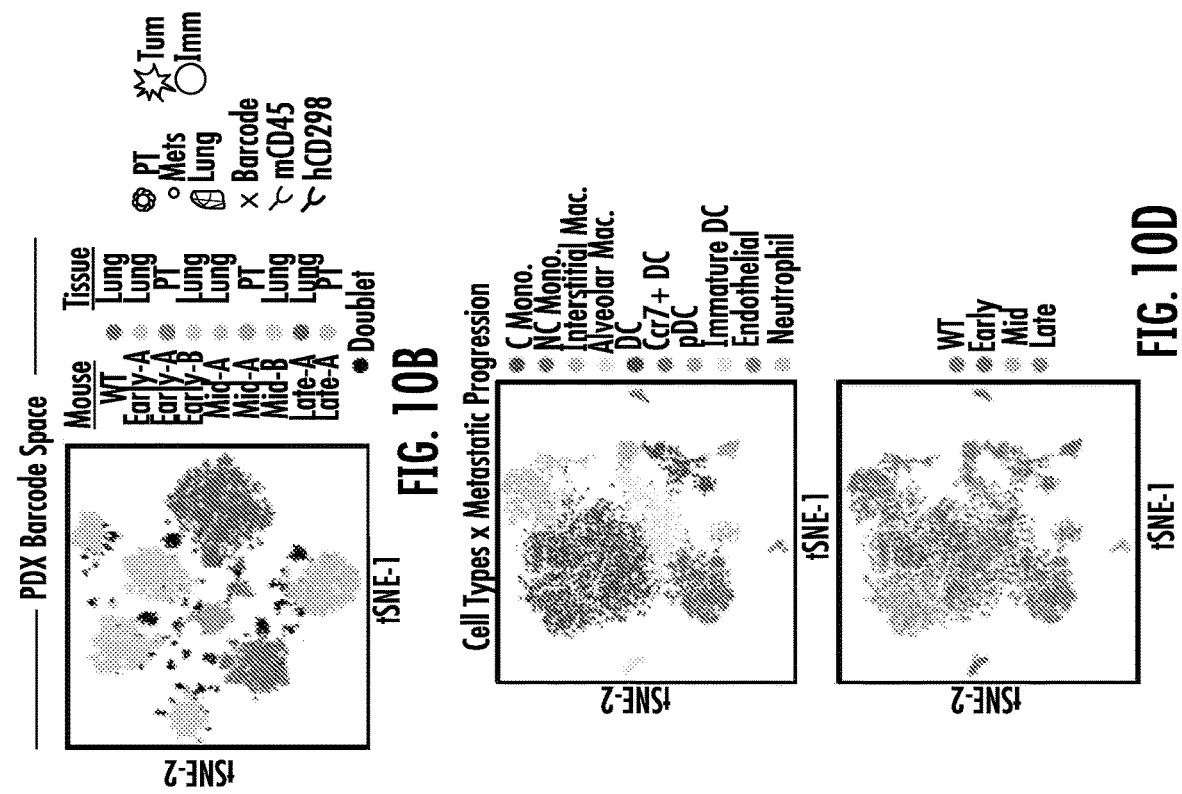

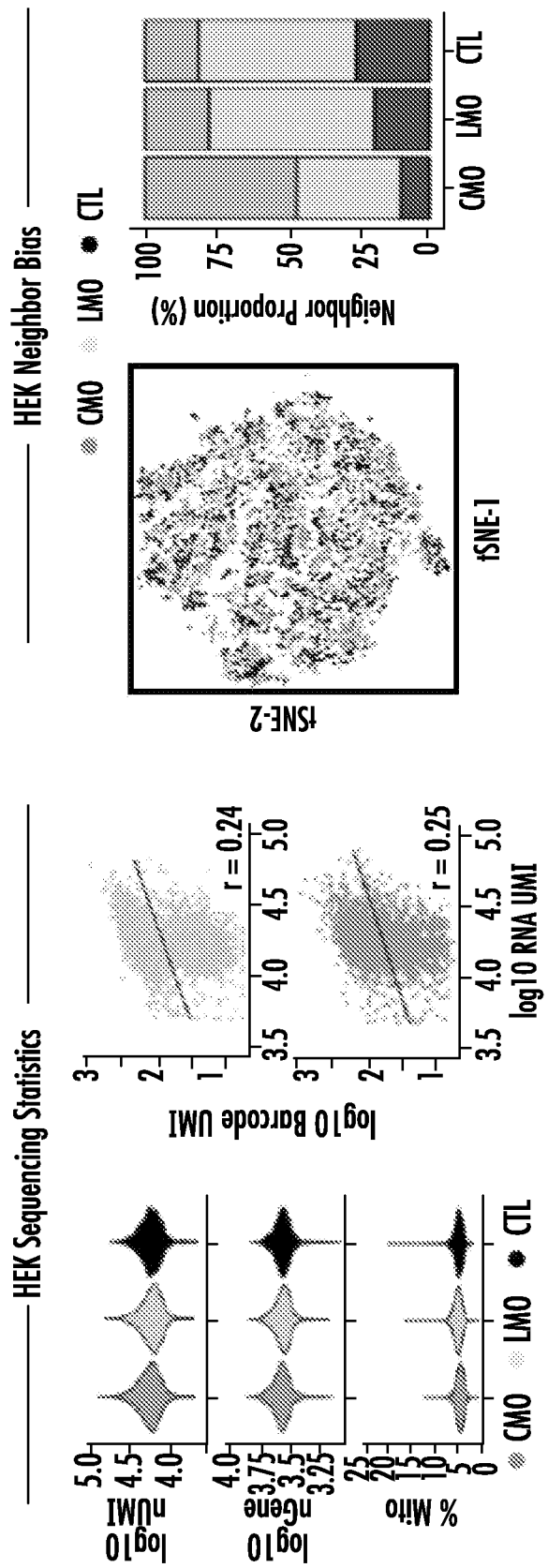
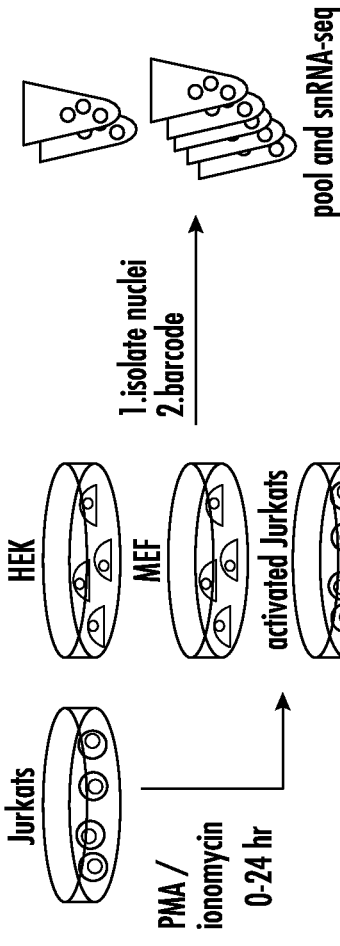
FIG. 12C
FIG. 12D
FIG. 12E

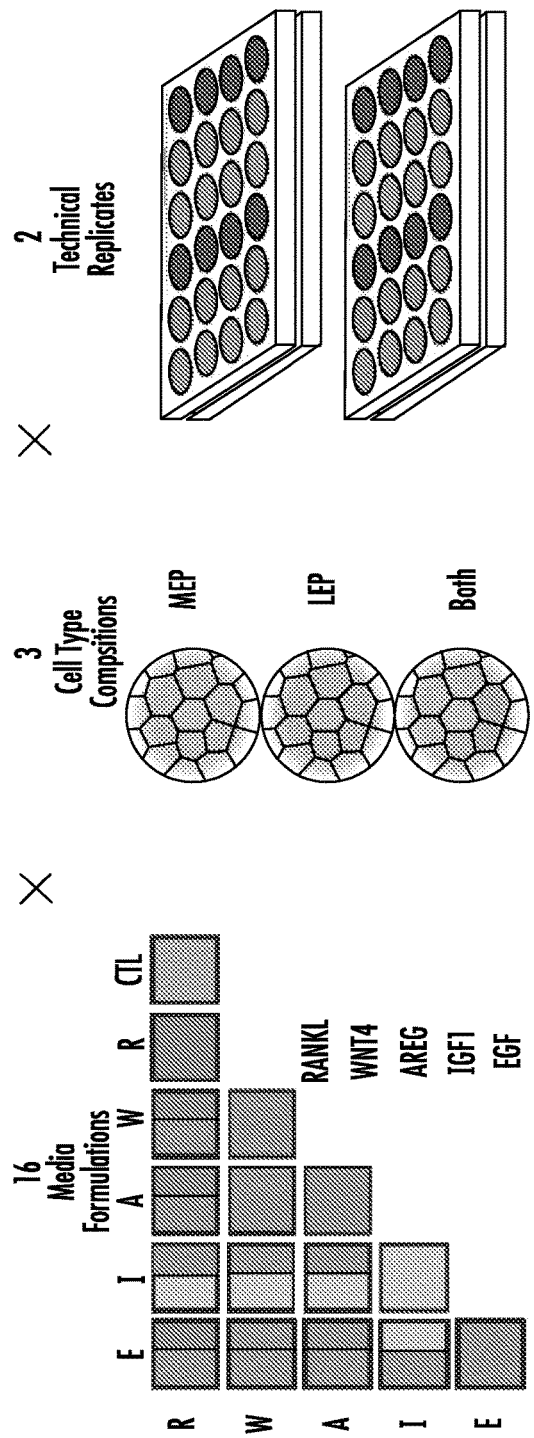
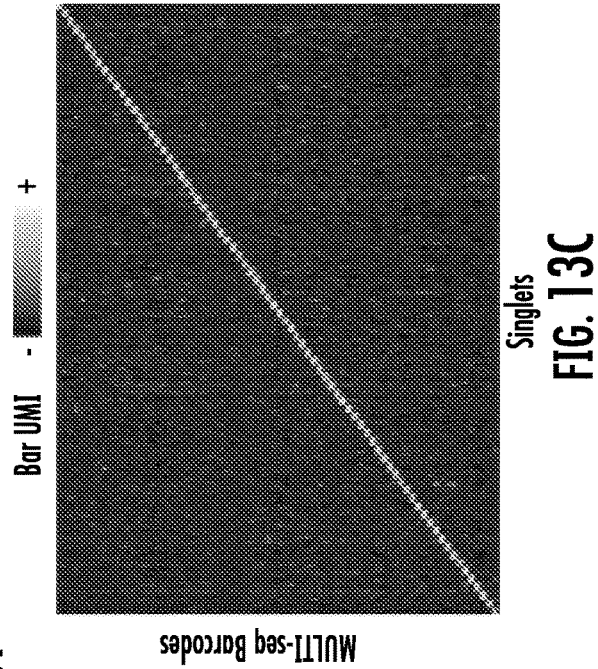
FIG. 13A
FIG. 13B
FIG. 13C

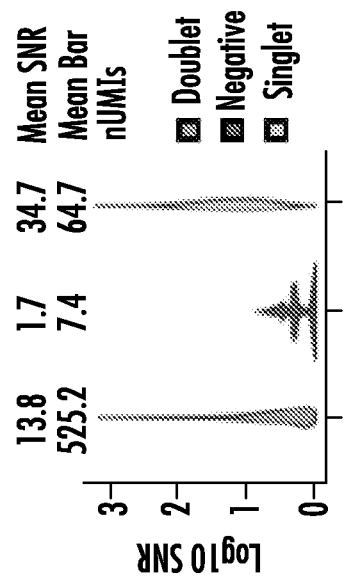
FIG. 13G
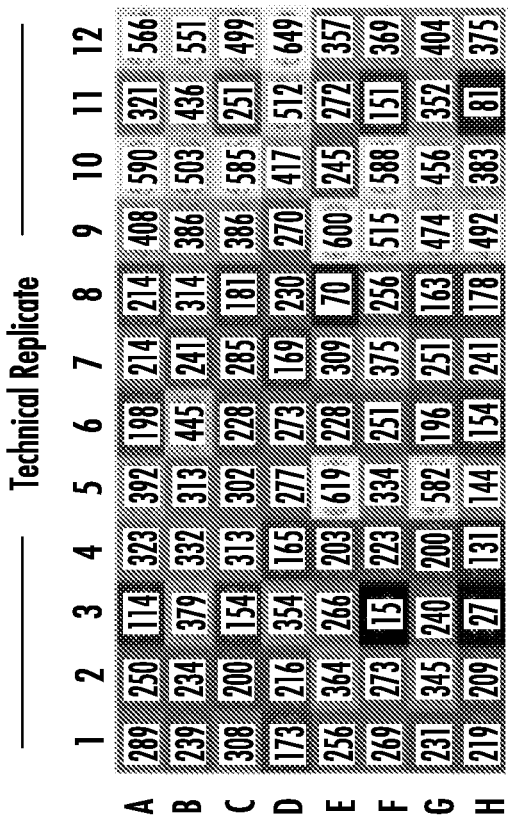
FIG. 13E
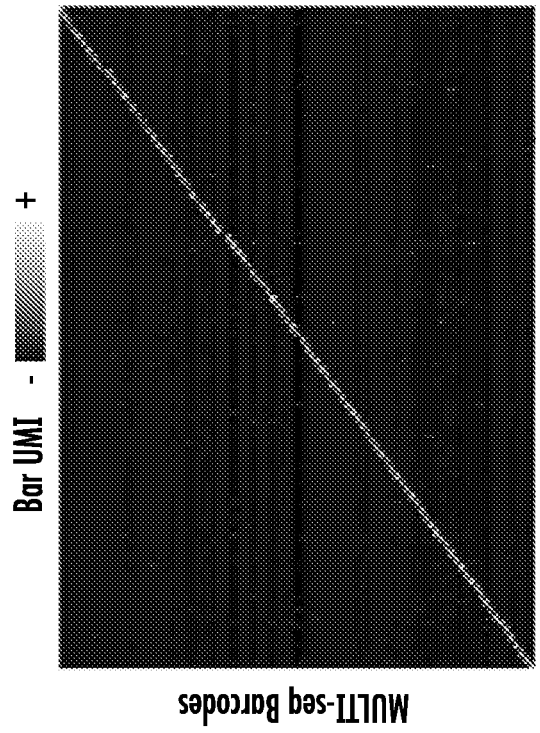
FIG. 13D
FIG. 13F

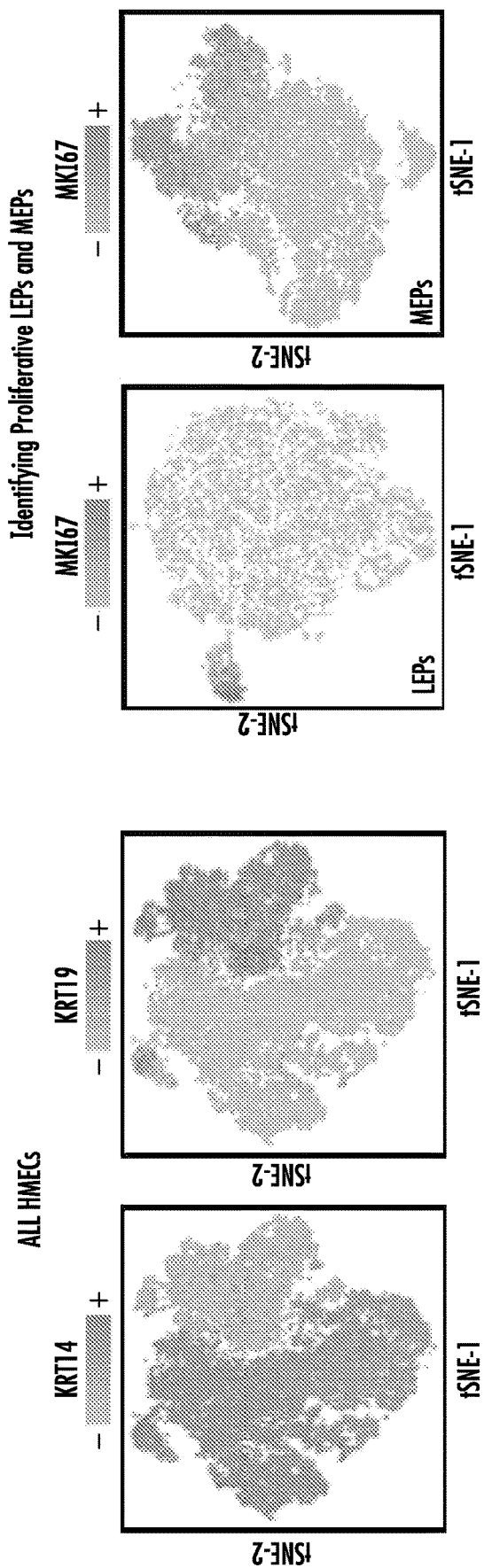
FIG. 15A
FIG. 15B
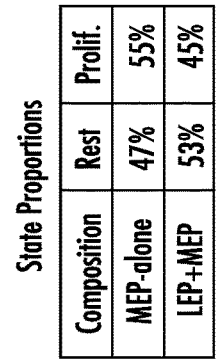
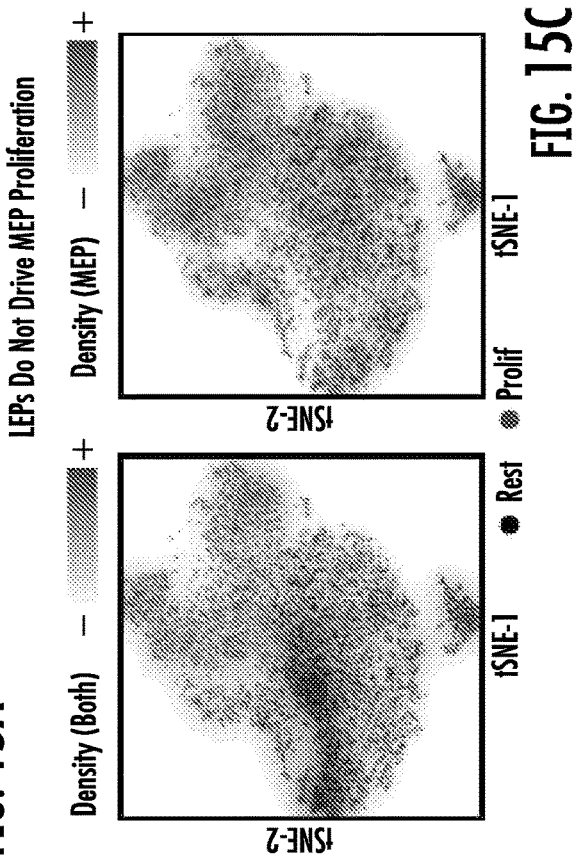
FIG. 15C

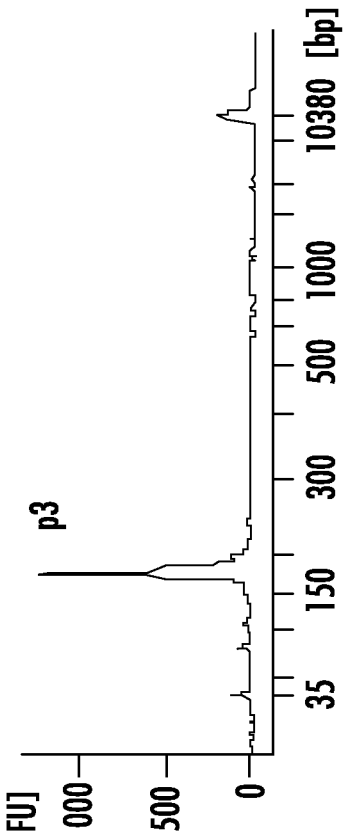
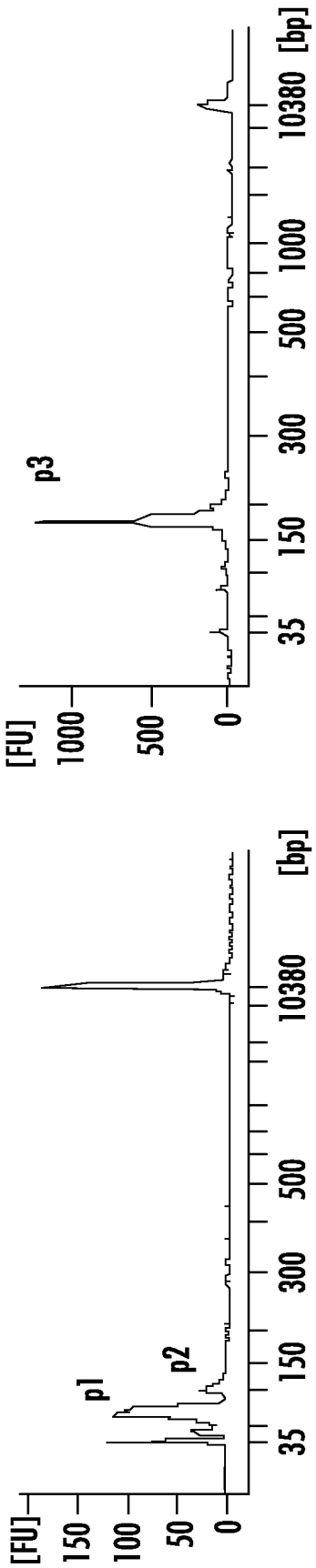
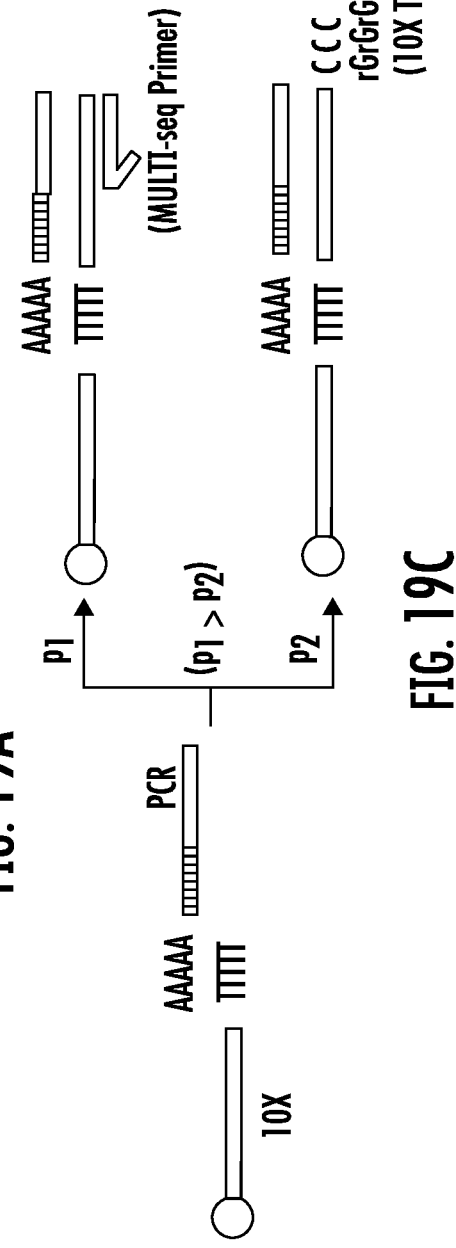

| Comparison | Markers | FC | Comparison | Markers | FC | Comparison | Markers | FC |
|---|---|---|---|---|---|---|---|---|
| LMO vs UN | MIF | 2.8 | LMO vs CMO | SNORA76 | 1.7 | CMO vs UN | MIF | 1.9 |
| | KRTCAP2 | 1.5 | | NMT1 | 1.5 | | S100A2 | 1.6 |
| | TOMM5 | 1.5 | | | | | MT2A | 1.5 |
| | | | | | | | AP2B1 | -1.5 |
| | | | | | | | TOP2A | -1.5 |
| | | | | | | | MALAT1 | -1.5 |
| | | | | | | | SNORA76 | -1.7 |
| | | | | | | | NMT1 | -1.8 |

LMO = LMO-labeled HEKs, CMO = CMO-labeled HEKs,
UN = Unlabeled HEKs, FC = Fold-change

FIG. 20

| Dataset | %Aligned | %Duplicate UMI | UMIs/cell | SNR | NGS Format |
|---|---|---|---|---|---|
| POC-LMO | 93.8 | 6.25 | 77 | 69 | HiSeq 4000 (33.3%) |
| POC-CMO | 94.4 | 5.74 | 55 | 41 | HiSeq 4000 (33.3%) |
| HMEC-orig | 97.1 | 12.62 | 5095 | 199 | HiSeq 4000 (100%) |
| HMEC-rep | 97.3 | 13.67 | 65 | 34.7 | HiSeq 4000 (50%) |
| PDX | 99.0 | 17.36 | 4453 | 49.6 | NovaSeq (2.5%) |
| Nuclei (LMO) | 98.8 | 28.67 | 731 | 2.3 | NovaSeq (1.25%) |
| Nuclei (CMO) | 98.6 | 28.18 | 8415 | 91.5 | NovaSeq (1.25%) |

% Aligned = Alignment rate, i.e., the proportion of reads aligning to any reference barcode.
SNR = Signal-to-noise ratio, i.e., the primary classification barcode divided by the next most abundant barcode.
All sequencing statistics were computed on the subset of reads associated with classified singlets.
POC = Proof-of-concept. PDX = Patient-Derived Xenograft, HMEC = Human mammary epithelial cell.

FIG. 21

| Sample | MouseID | #Cells | Viability | pHu-FACS | pHu-10X | pMo-FACS | pMo-10X |
|---|---|---|---|---|---|---|---|
| Early-1-PT | 1 | 280K | 0.647 | 0 | 0 | 1 | 1 |
| Mid-1-PT | 2 | 580K | 0.0153 | 0 | 0 | 1 | 1 |
| Late-PT | 3 | 665K | 0.0845 | 0 | 0 | 1 | 1 |
| Early-1-Lung | 1 | 700K | 0.33 | 0 | 0.01 | 1 | 0.99 |
| Early-2-Lung | 4 | 340K | 0.38 | 0 | 0 | 1 | 1 |
| Mid-1-Lung | 2 | 370K | 0.50 | 0.02 | 0.02 | 0.98 | 0.98 |
| Mid-2-Lung | 5 | 550K | 0.309 | 0.01 | 0.01 | 0.99 | 0.99 |
| Late-Lung | 3 | 550K | 0.314 | 0.22 | 0.15 | 0.78 | 0.85 |
| WT-Lung | 6 | 460K | 0.392 | 0 | 0 | 1 | 1 |

Number of cells and viability refer to the LMO labeling reaction.
pHu-FACS, pMo-FACS = Proportion of human and mouse cells sorted using FACS.
pHu-10X, pMo-10X = Proportion of human and mouse cells present in the final dataset.

FIG. 22

Classified

| Cluster | Markers | FC |
|---|---|---|
| Monocyte | Pou2f2 | 4.2 |
| | Rpsa | 2.6 |
| | Csf1r | 2.6 |
| | Ahnak | 2.7 |
| | Cx3cr1 | 4.0 |
| Interstitial Mac. | C1qa | 11.0 |
| | C1qb | 9.0 |
| | Apoe | 6.1 |
| | C1qc | 7.6 |
| | Ccl8 | 20.4 |
| Alveolar Mac. | Ear2 | 16.0 |
| | Ear10 | 17.7 |
| | Ctsd | 6.4 |
| | Chil3 | 7.5 |
| | Lpl | 7.7 |
| Neutrophil | S100a8 | 61.1 |
| | S100a9 | 57.6 |
| | Il1b | 9.3 |
| | Msrb1 | 5.8 |
| | Srgn | 5.0 |
| Endothelial | Ramp2 | 58.2 |
| | Ly6c1 | 60.2 |
| | Cldn5 | 38.1 |
| | Ctla2a | 34.4 |
| | Aqp1 | 25.3 |

Unlassified

| Cluster | Markers | FC |
|---|---|---|
| Broken-1 | Xist | 4.3 |
| | Lgals1 | 1.6 |
| | Rpl25 | 1.6 |
| | Rps20 | 1.8 |
| | Grn | 1.9 |
| Broken-2 | mt-Nd4 | 2.3 |
| | mt-Nd1 | 2.4 |
| | Rpl14 | 1.7 |
| | mt-Co2 | 2.4 |
| | mt-Co3 | 2.5 |
| Neutrophil | S100a9 | 47.4 |
| | S100a8 | 48.6 |
| | Retnlg | 48.3 |
| | Pglyrp1 | 13.1 |
| | S100a11 | 9.2 |

FIG. 23

| CLUSTER | MARKERS | FC |
|---|---|---|
| WT | Ear2 | 2.3 |
| | Rsrp1 | 2.1 |
| | Plaur | 1.7 |
| | Rgcc | 2.1 |
| | Klf4 | 1.7 |
| | Jund | 1.6 |
| | Wsb1 | 1.6 |
| | Pdlim1 | 1.6 |
| | Tagln2 | 1.6 |
| | Pglyrp1 | 2.0 |
| | Fn1 | 1.5 |
| | Ezr | 1.5 |
| | Tsc22d3 | 1.5 |
| | Cks2 | 1.8 |
| | Hspa1a | 1.6 |
| EARLY/MID | Isg15 | 1.8 |
| | Thbs1 | 1.7 |
| MID-2 | Tppp3 | 2.4 |
| | Adgre5 | 1.7 |
| | Tagln2 | 1.7 |
| | Crip1 | 1.6 |
| | Metrnl | 1.8 |
| | Emp3 | 1.6 |
| | Cd74 | 2.1 |
| | Cd300a | 1.6 |
| | Btg2 | 1.5 |
| | Pou2f2 | 1.7 |
| | Sgk1 | 1.6 |
| | Il1b | 1.8 |
| | Gngt2 | 1.5 |
| | Hist1h1c | 1.6 |

| CLUSTER | MARKERS | FC |
|---|---|---|
| LATE-1 | Fos | 2.6 |
| | Dusp1 | 2.3 |
| | Jun | 2.6 |
| | Atf3 | 2.2 |
| | Ier3 | 2.0 |
| | Ccl3 | 2.6 |
| | Tsc22d3 | 1.7 |
| | S100a8 | 3.7 |
| | Ccl2 | 2.0 |
| | Saa3 | 2.5 |
| | Fosb | 1.7 |
| | Socs3 | 1.8 |
| | Wfdc21 | 2.4 |
| | Klf6 | 1.5 |
| | S100a9 | 2.2 |
| | Egr1 | 1.5 |
| | Hspa1a | 1.8 |
| | Lcn2 | 1.6 |
| | Lrg1 | 1.6 |
| | Ccl4 | 1.9 |
| LATE-2 | Rgcc | 2.8 |
| | Rsrp1 | 2.8 |
| | Nfkbia | 2.4 |
| | Mmp19 | 2.4 |
| | Cxcr4 | 2.3 |
| | Arg2 | 2.3 |
| | Lmna | 2.2 |
| | Saa3 | 2.0 |

FIG. 24

| CM Subtype | Markers | FC |
|---|---|---|
| Thsb1+ Cd14+ Late CMs | Cd14 | 2.4 |
| | Cepbp | 1.5 |
| | Lmna | 2.2 |
| | Btg1 | 1.5 |
| | Plaur | 1.6 |
| | Rgcc | 1.9 |
| | Nfkbia | 1.6 |
| | Tnpo3 | 1.6 |
| | Tlr2 | 1.6 |
| | Tubb6 | 1.6 |
| | C5ar1 | 1.6 |
| | Mmp19 | 1.6 |
| | Cxcr4 | 1.7 |
| | Tppp3 | 1.7 |
| | Ninj1 | 1.5 |
| | Skil | 1.5 |
| | Thbs1 | 1.6 |
| | Dmkn | 1.6 |

| CM Subtype | Markers | FC |
|---|---|---|
| Thsb1- Cd14- Late CMs | Fos | 2.8 |
| | Dusp1 | 2.4 |
| | Jun | 2.5 |
| | Atf3 | 2.1 |
| | Ccl3 | 2.7 |
| | Tsc22d3 | 1.7 |
| | Rgs2 | 1.7 |
| | S100a8 | 3.2 |
| | S100a9 | 2.6 |
| | Txnip | 1.6 |
| | Egr1 | 1.6 |
| | Ccl4 | 2.2 |
| | Ccl2 | 1.5 |
| | Wfdc21 | 1.5 |

FIG. 25

Experimental Workflow ~ Adult Gut
FIG. 26A
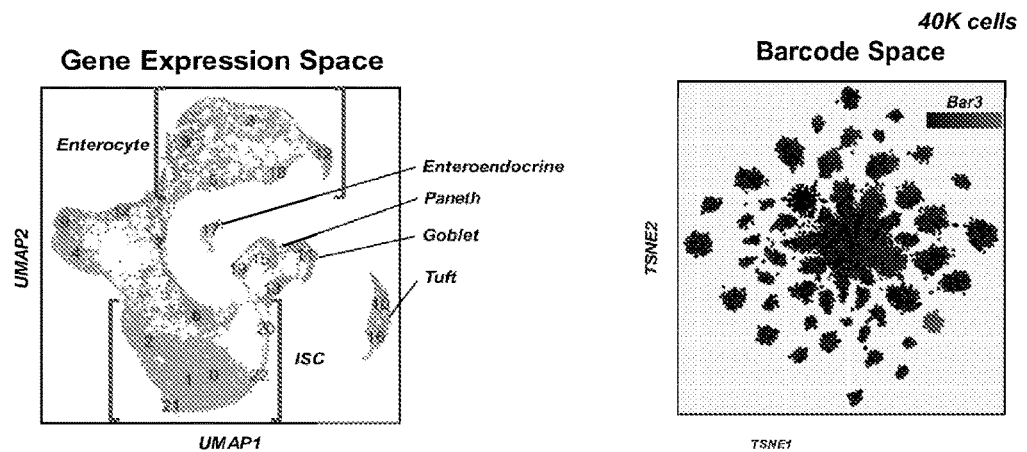
FIG. 26B    FIG. 26C
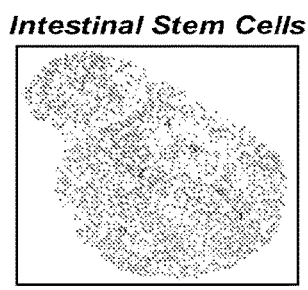    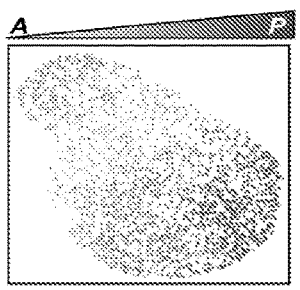
FIG. 26D    FIG. 26E
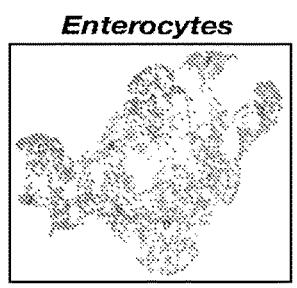    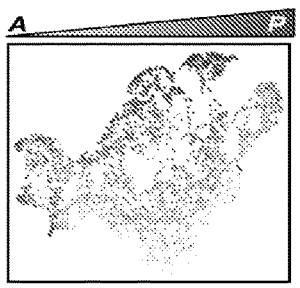
FIG. 26F    FIG. 26G
Spatial position informs gene expression patterns in intestinal stem cells and enterocytes

Experimental Workflow – Developing Gut
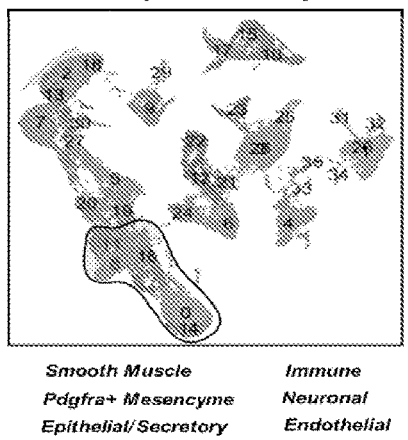
FIG. 27A
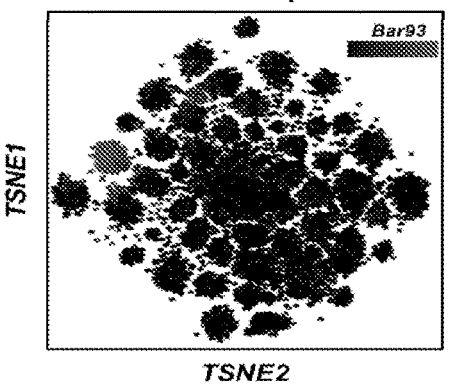
FIG. 27B
FIG. 27C
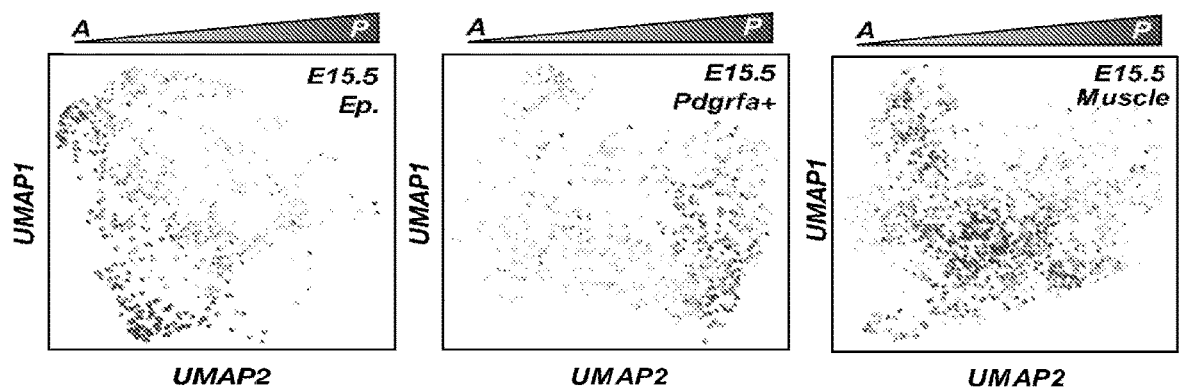
FIG. 27D   FIG. 27E   FIG. 27F

SEQUENCE LISTING

<160> NUMBER OF SEQ ID NOS: 14

<210> SEQ ID NO 1
<211> LENGTH: 41
<212> TYPE: DNA
<213> ORGANISM: Homo sapiens

<400> SEQUENCE: 1
gtaacgatcc agctgtcact tggaattctc gggtgccaag g                41

<210> SEQ ID NO 2
<211> LENGTH: 20
<212> TYPE: DNA
<213> ORGANISM: Homo sapiens

<400> SEQUENCE: 2
agtgacagct ggatcgttac                                        20

<210> SEQ ID NO 3
<211> LENGTH: 59
<212> TYPE: DNA
<213> ORGANISM: Homo sapiens
<220> FEATURE:

```
<221> NAME/KEY: misc_feature
<222> LOCATION: (22)..(27)
<223> OTHER INFORMATION: n is a, c, g, or t

<400> SEQUENCE: 3
ccttggcacc cgagaattcc annnnnnaaa aaaaaaaaaa aaaaaaaaaa aaaaaaaa      59

<210> SEQ ID NO 4
<211> LENGTH: 20
<212> TYPE: DNA
<213> ORGANISM: Homo sapiens

<400> SEQUENCE: 4
gtaacgatcc agctgtcact                                               20

<210> SEQ ID NO 5
<211> LENGTH: 21
<212> TYPE: DNA
<213> ORGANISM: Homo sapiens

<400> SEQUENCE: 5
tggaattctc gggtgccaag g                                             21

<210> SEQ ID NO 6
<211> LENGTH: 21
<212> TYPE: DNA
<213> ORGANISM: Homo sapiens

<400> SEQUENCE: 6
ccttggcacc cgagaattcc a                                             21

<210> SEQ ID NO 7
<211> LENGTH: 32
<212> TYPE: DNA
<213> ORGANISM: Homo sapiens

<400> SEQUENCE: 7
aaaaaaaaaa aaaaaaaaaa aaaaaaaaaa aa                                 32

<210> SEQ ID NO 8
<211> LENGTH: 41
<212> TYPE: DNA
<213> ORGANISM: Artificial Sequence
<220> FEATURE:
<223> OTHER INFORMATION: DNA oligo

<400> SEQUENCE: 8
gtaacgatcc agctgtcact tggaattctc gggtgccaag g                       41

<210> SEQ ID NO 9
<211> LENGTH: 20
<212> TYPE: DNA
<213> ORGANISM: Artificial Sequence
<220> FEATURE:
<223> OTHER INFORMATION: DNA oligo

<400> SEQUENCE: 9
agtgacagct ggatcgttac                                               20

<210> SEQ ID NO 10
<211> LENGTH: 59
<212> TYPE: DNA
<213> ORGANISM: Artificial Sequence
<220> FEATURE:
<223> OTHER INFORMATION: DNA oligo
```

```
<220> FEATURE:
<221> NAME/KEY: misc_feature
<222> LOCATION: (12)..(17)
<223> OTHER INFORMATION: N is any of A, T, C, or G
<220> FEATURE:
<221> NAME/KEY: misc_feature
<222> LOCATION: (22)..(27)
<223> OTHER INFORMATION: N is any of A, T, C, or G

<400> SEQUENCE: 10
ccttggcacc cgagaattcc annnnnnaaa aaaaaaaaaa aaaaaaaaaa aaaaaaaa        59

<210> SEQ ID NO 11
<211> LENGTH: 30
<212> TYPE: DNA
<213> ORGANISM: Artificial Sequence
<220> FEATURE:
<223> OTHER INFORMATION: DNA oligo
<220> FEATURE:
<221> NAME/KEY: misc_feature
<222> LOCATION: (22)..(29)
<223> OTHER INFORMATION: N is any of A, T, C, or G

<400> SEQUENCE: 11
ccttggcacc cgagaattcc annnnnnnna                                       30

<210> SEQ ID NO 12
<211> LENGTH: 63
<212> TYPE: DNA
<213> ORGANISM: Artificial Sequence
<220> FEATURE:
<223> OTHER INFORMATION: DNA oligo
<220> FEATURE:
<221> NAME/KEY: misc_feature
<222> LOCATION: (25)..(30)
<223> OTHER INFORMATION: N is any of A, T, C, or G

<400> SEQUENCE: 12
caagcagaag acggcatacg agatnnnnnn gtgactggag ttccttggca cccgagaatt      60
cca                                                                    63

<210> SEQ ID NO 13
<211> LENGTH: 58
<212> TYPE: DNA
<213> ORGANISM: Artificial Sequence
<220> FEATURE:
<223> OTHER INFORMATION: DNA oligo

<400> SEQUENCE: 13
aatgatacgg cgaccaccga gatctacact ctttccctac acgacgctct tccgatct        58

<210> SEQ ID NO 14
<211> LENGTH: 20
<212> TYPE: DNA
<213> ORGANISM: Artificial Sequence
<220> FEATURE:
<223> OTHER INFORMATION: DNA oligo

<400> SEQUENCE: 14
ccttggcacc cgagaattcc                                                  20
```

LIPID-MODIFIED OLIGONUCLEOTIDES AND METHODS OF USING THE SAME

RELATED APPLICATIONS

The present application is a National Stage application filed under 35 U.S.C. § 371 of International Application No. PCT/US2019/040898, filed on Jul. 8, 2019, which claims priority to U.S. Provisional Application No. 62/694,970, filed Jul. 6, 2018, and U.S. Provisional Application No. 62/847,916, filed May 14, 2019, the contents of the aforementioned applications are hereby incorporated by reference in their entireties.

STATEMENT REGARDING FEDERALLY SPONSORED RESEARCH

This invention was made with government support under Grant No. HD080351 awarded by the National Institutes of Health and Grant No. W81XWH-13-1-0221 awarded by the United States Army Medical Research and Materiel Command. The Government has certain rights in the invention.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 37944.0009U3_SL. The size of the text file is 4 KB and the text file was created on Jan. 6, 2021.

FIELD

The disclosure generally relates to methods and applications of single-cell barcoding and methods of nucleotide sequencing using composition comprising lipid-modified oligonucleotides.

BACKGROUND

Single-cell RNA sequencing has become a powerful tool for mapping transcriptional changes in cells. The main advantage of this technique is the ability to survey a diversity of cells in a sample. All single-cell RNA-sequencing protocols share a common initial step in which transcribed RNA from cells is converted to cDNA. The next step is amplification by methods such as PCR and in vitro transcription (IVT). The subsequent steps, culminating in sequencing, allow the expression level of gene products to be quantified. Isolation and barcoding of RNA from single cells is the first and crucial limiting step in single-cell RNA-seq.

Recently, large scale screens (genetic perturbation using shRNA or CRISPR) combined with single-cell RNA sequencing were performed to understand complex biological phenomena. These have a distinct advantage of easy identification/barcoding of samples by shRNA or CRISPR gRNA sequence. Genetic perturbation techniques can be directly coupled with barcode introduction (i.e., by adding polyA+barcodes to the gRNA or shRNA, themselves), whereas, chemical/drug/patient screens that do not involve genetic manipulation have not been able to be barcoded in a fashion that can be "read-out" via scRNA-seq. See, e.g., Adamson et al., Cell 167(7):1867-82 (2016); Aarts et al., Genes Dev. 31(20):2085-98 (2017); Jaitin et al., Cell 167 (7):1883-96 (2016).

In single-cell RNA sequencing assays, multiplexing is traditionally achieved through the addition of molecular barcodes to cDNA fragments or beads, depending the application. This is done after isolating cells either using droplet microfluidics or using microwells. To allow labeling of cDNA from cells isolated in individual droplets (or microwells), beads can be used with reverse transcription (RT) primers that also contain a barcode (or in some cases with the barcode on the bead). RT and barcoding can therefore happen in each individual droplet or well. The current methods have at least the following drawbacks: high cost, low efficiency and low multiplexing capabilities. The current sample multiplexing capacity of commercial droplet microfluidics-based single-cell RNA sequencing is limited to eight due to the number of discrete channels used for cellular emulsion and co-encapsulation with mRNA capture beads.

SUMMARY OF EMBODIMENTS

The disclosure relates to composition comprising oligonucleotides specifically designed to label cells and compositions of pooled cells labeled with distinct exogenous oligonucleotide barcodes that correspond to different sample preparations (e.g., patients, perturbations, replicates of a single experiment, etc.). By incorporating sample-specific information in the form of lipid-modified exogenous oligonucleotides, sample throughput levels will no longer be limited to being defined by the physical dimensions of microfluidics devices. Enhancing sample multiplexing will reduce the cost of single-cell RNA sequencing, limit technical noise arising from batch effects, and make single-cell transcriptome datasets more informative.

The disclosure relates to compositions and methods of using those compositions for barcoding single cells and for RNA sequencing analysis using lipid-modified oligonucleotides. The disclosure also relates to a method of multiplexing droplets comprising single cells. The disclosure also relates to methods to process a greater amount of a single sample without the confounding artifact of cell doublets. The sample can then be split into several aliquots, each with a different barcoded lipid-modified oligonucleotide and then pooled before running on a single-cell RNA system. This will enable the removal of cell doublets computationally while increasing the total number of single cells processed.

One aspect is for a composition comprising: (a) a first lipid-conjugated DNA oligonucleotide comprising a first lipid moiety, a first hybridization region, and a first primer region; (b) a second lipid-conjugated DNA oligonucleotide comprising a second hybridization region and a second lipid moiety, wherein the second hybridization region is the reverse complement of the first hybridization region; and (c) a third DNA oligonucleotide comprising a second primer region, a barcode region, and a capture sequence, wherein the second primer region is the reverse complement of the first primer region. Alternatively, in some aspects, the composition can comprise a lipid-conjugated DNA oligonucleotide comprising a lipid moiety, a barcode region, and a capture sequence. In some aspects the composition can comprise: (a) a first lipid-conjugated DNA oligonucleotide comprising a lipid moiety and a first primer region; and (b) a second DNA oligonucleotide comprising a second primer region, a barcode region, and a capture sequence, wherein the second primer region is the reverse complement of the first primer region.

Another aspect is for a membrane comprising the aforementioned composition.

A further aspect is for a cell comprising the aforementioned composition.

An additional aspect is for a kit comprising the aforementioned composition.

Another aspect is for a method of RNA sequencing comprising contacting a cell with the aforementioned composition.

A further aspect is for a method of quantifying mRNA levels of at least one gene in a sample, the method comprising contacting the sample with the aforementioned composition.

An additional aspect is for a method of quantifying mRNA levels in a sample, the method comprising: (a) adding two or more single cells from the sample to two or more vessels on a solid support comprising at least one surface, wherein each vessel comprises a single cell from the sample and is addressable from a point external to the solid support; and (b) contacting each of the single cells with the aforementioned composition such that each cell comprises the composition, and each cell is independently addressable to measure differences in mRNA levels between the at least two cells.

Another aspect is for a method of determining the toxicity of a compound, the method comprising contacting one or more compounds with one or more cells comprising the aforementioned composition.

A further aspect is for a method of diagnosing a disorder in a subject, the method comprising measuring expression of a marker gene in a sample obtained from the subject, wherein the measuring comprises contacting the sample with the aforementioned composition, and wherein an increase or decrease in expression of the marker gene from a predetermined level indicates that the subject is afflicted with the disorder.

An additional aspect is for a method of quantifying the number of modified cells in a sample, the method comprising contacting the sample with the aforementioned composition.

Another aspect is for a method of determining a cellular expression pattern, the method comprising: (a) contacting a cell with a chemical compound; and (b) measuring expression of one or more genes from the cell as compared to expression of the one or more genes from an equivalent cell that has not been contacted with the chemical compound, wherein the measuring comprises contacting the cell with the aforementioned composition.

BRIEF DESCRIPTION OF DRAWINGS

FIG. 8C shows cell type annotations for LMO-labeled cells demonstrate separation between HEKs (pink), MEPs (cyan), and LEPs (dark teal) in gene expression space (see FIG. 12A). Ambiguous cells positive for multiple marker genes are displayed in grey. n=6,186 MULTI-seq barcoded cells.

FIG. 8D shows MULTI-seq sample classifications for HEKs (dark red), unstimulated HMECs (green), and TGF-β-stimulated HMECs (blue) match cell state annotations. Cells classified as doublets (black) predominantly overlap with ambiguously-annotated cells. n=6,186 MULTI-seq barcoded cells.

FIG. 8E shows a TGF-β-stimulated HMECs (blue) exhibited elevated TGFBI expression relative to unstimulated HMECs (green). ***=Wilcoxon rank sum test (two-sided), p<=10-16. n=1,950 MULTI-seq barcoded HMECs. Data are represented as mean±SEM.

FIG. 8F shows a Single nucleus MULTI-seq sample classification proportions for each cell type identified by clustering in gene expression space (see FIG. 12E-G). n=5,894 MULTI-seq barcoded nuclei.

FIG. 8G shows MULTI-seq sample classifications illuminate temporal gene expression patterns in Jurkat cells following activation with ionomycin and PMA for varying amounts of time. Time-point centroids in gene expression space are denoted with larger circles. n=3,709 Jurkat nuclei.

FIG. 8H shows violin plots of gene expression marking different stages of Jurkat cell activation. n=3,709 Jurkat nuclei.

FIG. 9A shows barcode UMI abundances (left) and doublet classifications (right) mapped onto barcode space. MULTI-seq barcode #3 is used as a representative example. Doublets localize to the peripheries of sample groups in large-scale sample multiplexing experiments. n=25,166 cells.

FIG. 9B shows cell state annotations demonstrate separation between MEPs (cyan) and LEPs (dark teal) in gene expression space (left, see FIG. 15A). Ambiguous cells positive for multiple marker genes are displayed in grey. MULTI-seq classifications grouped by culture composition (right)—e.g., LEP-alone (blue), MEP-alone (green), and both cell types together (dark red)—match cell state annotations. Discordant region where annotated MEPs are classified as doublets by MULTI-seq is indicated with arrows. n=25,166 cells.

FIG. 9C shows MULTI-seq doublet classifications (left) and computational predictions produced by DoubletFinder (right) largely overlap in gene expression space. Discordant region where DoubletFinder-defined doublets that are classified as singlets by MULTI-seq indicated with arrows. n=25,166 cells.

FIG. 10A shows a schematic overview of PDX experiment.

FIG. 10B shows MULTI-seq sample classifications (WT, early, mid, late tumor progression) mapped onto barcode space. Replicate tissues are denoted as 'A' or 'B'. n=10,427 cells.

FIG. 10C shows MULTI-seq classifications facilitate low-RNA and low-quality cell deconvolution. CellRanger discards cells barcodes with low RNA UMI counts (red dotted line). Gene expression profiles for classified low-RNA cells reflect established immune cell types (top right, see FIG. 16F). Unclassified low-RNA cells resemble low-quality single-cell transcriptomes (bottom right, see FIG. 23). n=2,580 (classified), 583 (unclassified) cells.

FIG. 10D shows cell state annotations (top) and tumor stages (bottom) for lung immune cells in gene expression space. Mono.=monocyte, C=classical, NC=non-classical, Mac.=macrophage, DC=dendritic cell, pDC=plasmacytoid DC. Cells with undeterminable annotations displayed in grey. n=5,965 cells.

FIG. 12C shows violin plots (left) describing the number of detected UMIs, number of detected genes, and percentage of mitochondrial gene expression for LMO-labeled (gold), CMO-labeled (purple), and unlabeled control HEKs (black). Distributions are largely identical, suggesting that LMO- and/or CMO-labeling does not negatively influence endogenous mRNA capture. This point is further supported by the observation that barcode UMIs and RNA UMIs are slightly positively correlated for both LMO- and CMO-labeled cells (right), suggesting that sample barcodes do not outcompete endogenous transcripts during mRNA capture. n=7,888 HEK cells. r=Pearson's correlation.

FIG. 12D shows HEK gene expression space colored by whether cells were LMO-labeled (gold), CMO-labeled (purple), or unlabeled (black) reveals sub-structure specific to CMO-labeling. Quantifying the proportion of LMO-, CMO-, and unlabeled cells amongst each cell's 100 nearest-neighbors in gene expression space emphasizes CMO-specific sub-structure. Unlabeled and LMO-labeled cells have similar neighborhoods while CMO-labeled cells preferentially co-localize in gene expression space. n=7,888 HEK cells.

FIG. 12E shows a schematic overview of a proof-of-concept snRNA-seq experiment using MULTI-seq. Nuclei were isolated from 10 distinct cell samples (HEKs (dark red), MEFs (blue), and Jurkats (green) stimulated with ionomycin and PMA for 8 distinct time points) prior to LMO barcoding and sequencing. CMO-labeled and unlabeled HEK and MEF nuclei were sequenced in parallel.

FIG. 13A shows a schematic overview of 96-plex HMEC scRNA-seq analysis. 96 distinct HMEC cultures consisting of LEPs alone (blue), MEPs alone (green), or both cell types together (dark red) were grown in media supplemented with 15 distinct signaling molecules or signaling molecule combinations and one control.

FIG. 13B shows 96-well plate schematic overlaid with a heat map showing the number of cells assigned to each sample barcode group. Twenty samples—predominantly those arising from column 2—were not represented in the original large-scale HMEC experiment due to technical error during sample preparation.

FIG. 13C shows a normalized barcode UMI heat map demonstrating that sample groups are predominantly associated with single MULTI-seq barcodes.

FIG. 13D shows violin plots describing the barcode UMI SNR for negative cells, doublets, and singlets. n=40,009 cells.

FIG. 13E shows the same analysis as described in FIG. 14A, except with the 96-plex HMEC technical replicate experiment. All samples were classified in the technical replicate.

FIG. 13F shows the same analysis as described in FIG. 14B, except with the 96-plex HMEC technical replicate experiment.

FIG. 13G shows the same analysis as described in FIG. 14C, except with the 96-plex HMEC technical replicate experiment. n=48,091 cells.

MKI67 enrichment was used as a proxy for distinguishing proliferative and resting LEPs and MEPs. n=6,159 (LEP) and 14,428 (MEP) cells.

FIG. 15C shows MEPs co-cultured with LEPs are not induced to proliferate relative to MEPs grown in monoculture. Clusters corresponding to resting (black) and proliferative (blue) LEPs are identifiable in gene expression space (FIG. 15B). Projecting sample classification densities onto gene expression space for co-cultured MEPs (red, left) and MEPs cultured alone (green, middle) illustrates that both culture compositions are equally proliferative (table, right). n=14,428 cells.

Figure 15E:
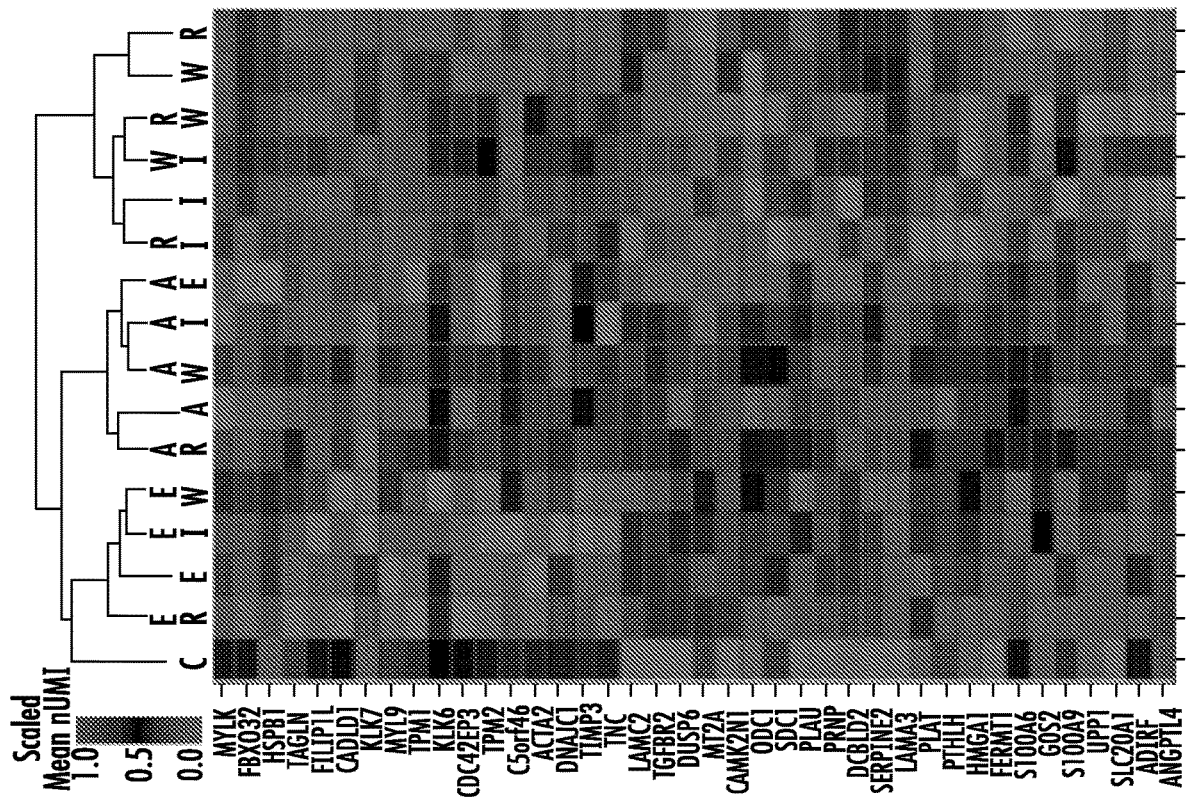
FIG. 15A shows distributions of marker gene expression used to identify MEPs (KRT14) and LEPs (KRT19) in gene expression space. n=25,166 cells.
FIG. 15B shows distributions of MKI67 expression in gene expression space for LEPs (left) and MEPs (right).
Figure 15D:
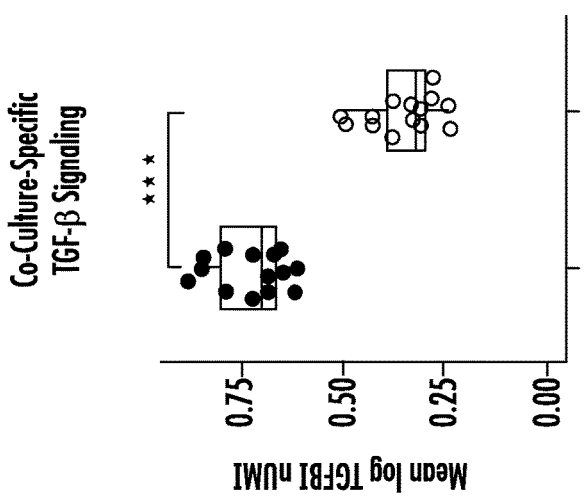

FIG. 15D shows MEPs co-cultured with LEPs exhibit enriched TGF-$\beta$ signaling (as measured by TGFBI expression) relative to MEPs grown in monoculture. Each point represents an average of MEPs grouped according signaling molecule treatment. ***=Wilcoxon rank sum test (two-sided), p=1.5×10−6. n=32 signaling molecule condition groups. Data are represented as mean±SEM.

FIG. 15E shows hierarchical clustering and heat map analysis of MEPs grouped by signaling molecule treatment highlights an EGFR signaling transcriptional response specific to EGF and AREG treatment. Dendrogram labels: E=EGF, W=WNT4, A=AREG, I=IGF-1, R=RANKL, C=Control.

Figure 16A:
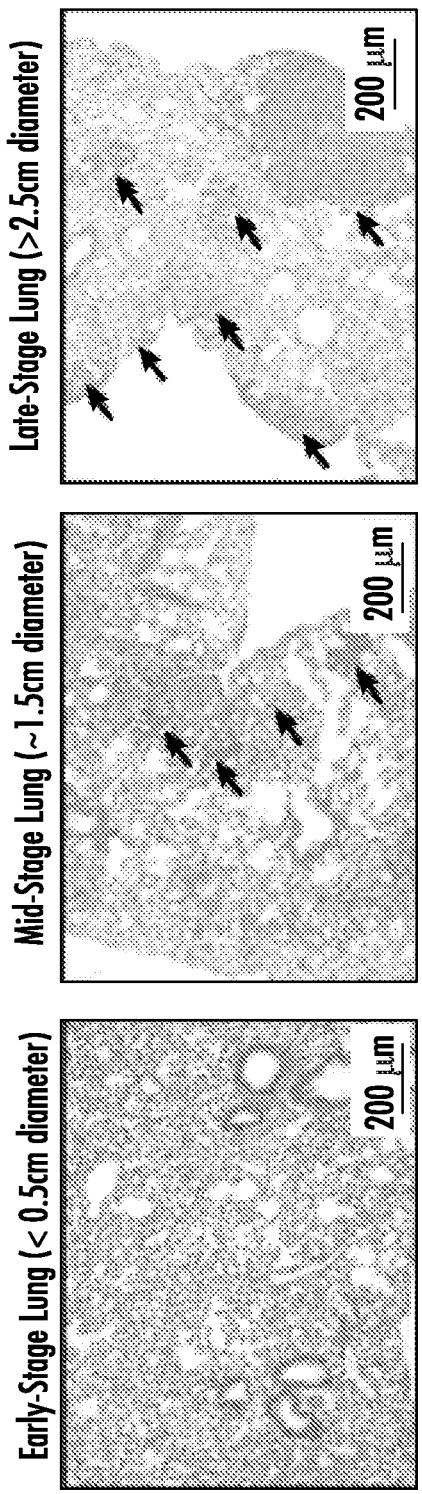

FIG. 16A shows a representative histology of lung tissue illustrates metastatic progression in early, mid, and late-stage PDX mice. Individual metastases denoted with black arrows. H&E staining was performed 3 times (early), 4 times (mid), and 10 times (late), yielding the same result.

Figure 16D:
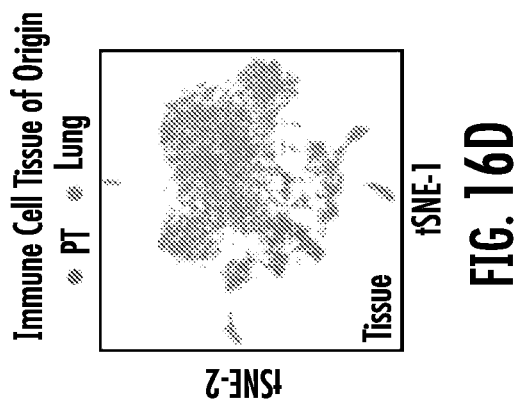
Figure 16C:
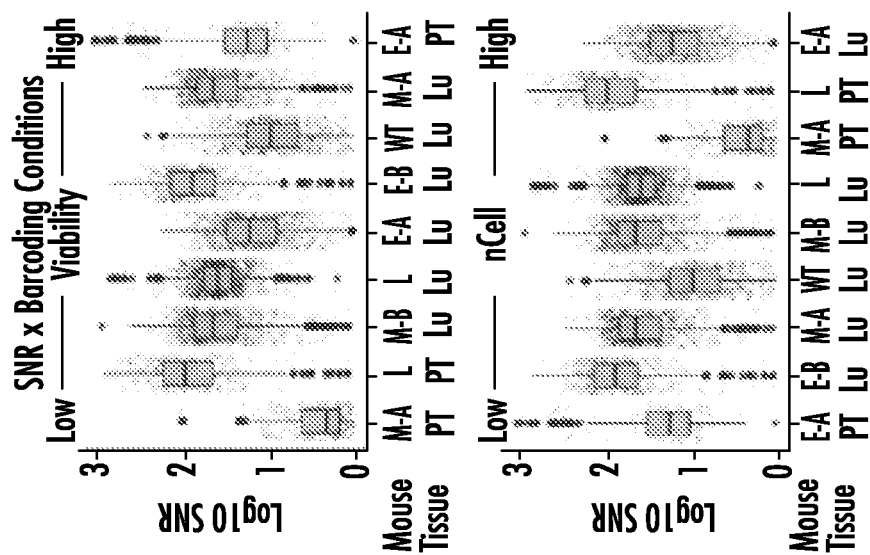
Figure 16B:
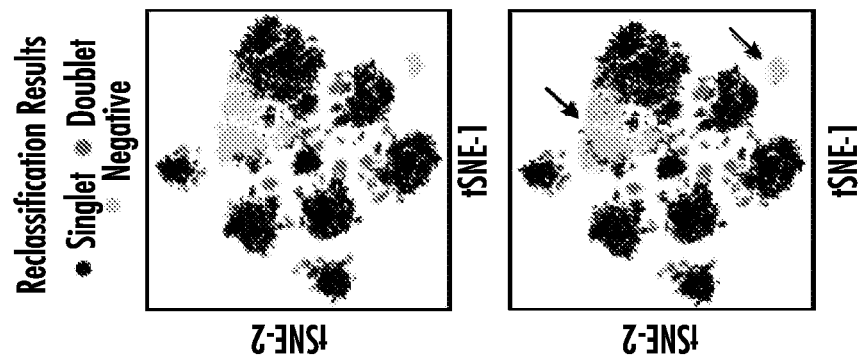

FIG. 16B shows negative cell reclassification improves sample classification results. Singlets (black) localize into clusters in barcode space whereas doublets (red) localize between singlet clusters. Negative cells either co-localize with singlet or doublet clusters (blue outline, bottom) or cluster separately (red outline, bottom). Negative cell reclassification is insensitive to the true-negatives that cluster separately, while rescuing a subset of false-negatives that cluster amongst singlets and doublets. n=12,086 cells.

FIG. 16C shows barcode SNR comparisons between samples ordered according to the viability (top) or total cell number (nCell, bottom) of the MULTI-seq barcoding conditions. See FIG. 22 for details. Data are represented as mean±SEM. n=10,427 cells.

FIG. 16D shows Mouse immune cells in gene expression space colored according to tissue of origin. Lung immune cells (brown) cluster separately from primary tumor immune cells (teal). n=8,420 cells.

Figure 16E:
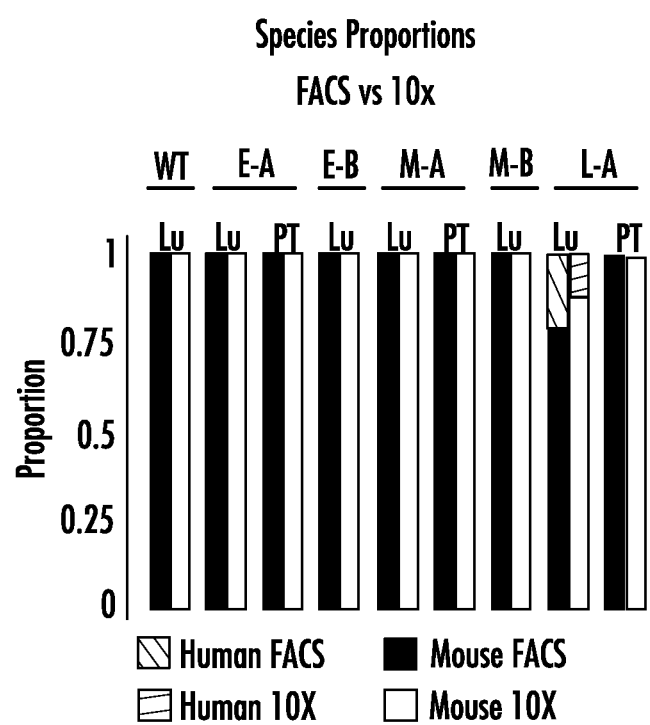

FIG. 16E shows bar plots describing the proportion of mouse (pink) and human (blue) cells detected during FACS enrichment and detected in the final 10× dataset. Classification of human and mouse cells from the L-A lung demonstrates sample classification accuracy and species-independence.

Figures 16F, 16G:
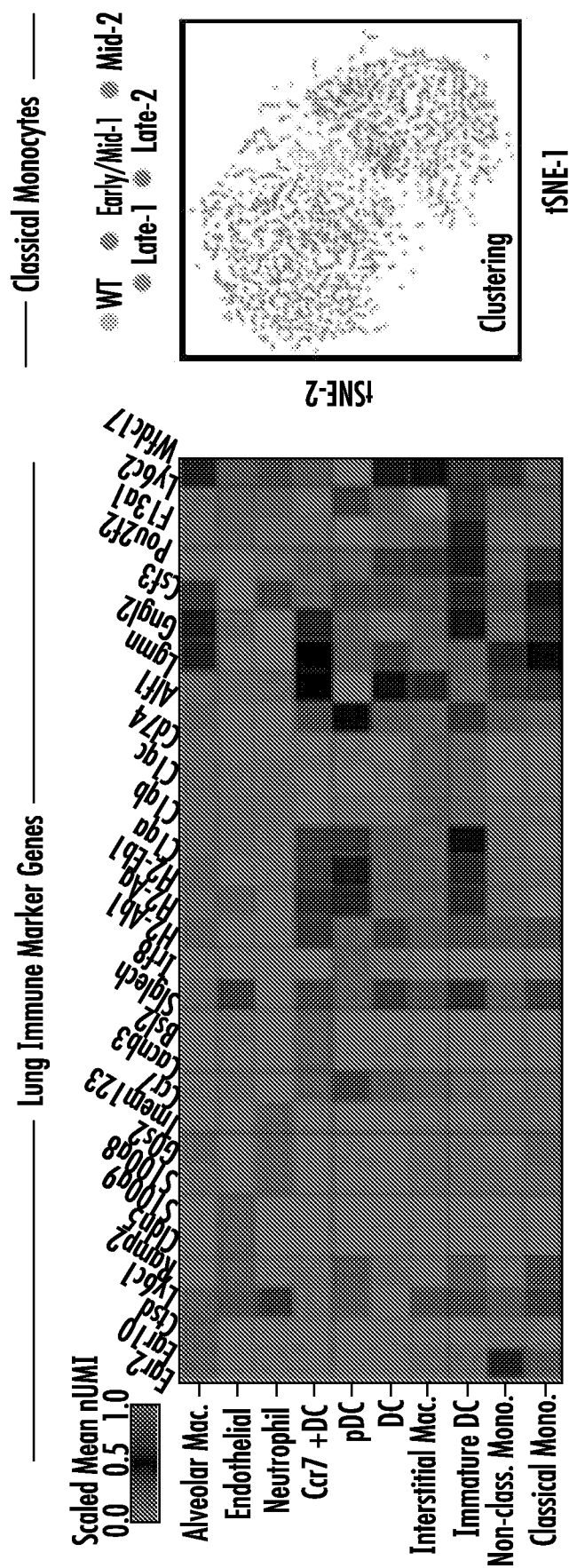

FIG. 16F shows a marker gene heat map describing markers utilized for defining cell type annotations. RNA UMI abundances are scaled from 0-1 for each gene. Values correspond to the average expression within each annotation group. Displayed genes represent the top 3 most statistically-significant genes for each cell type (Likelihood-ratio test for single cell gene expression with Bonferroni multiple comparisons adjustment).

Figure 10E:
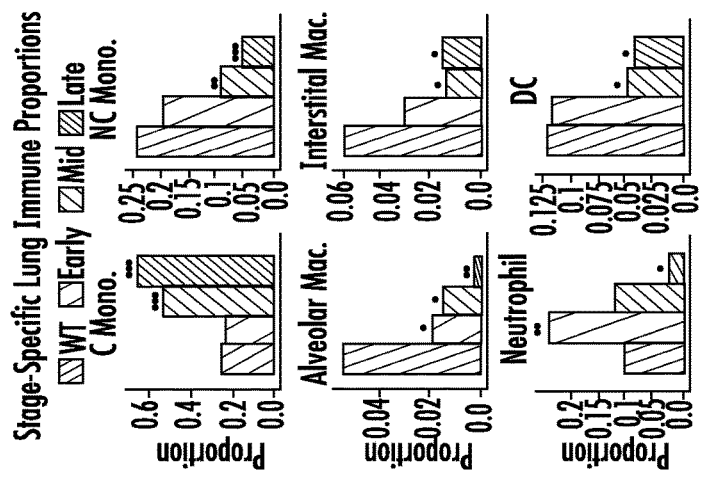
FIG. 10E shows statistically-significant shifts in lung immune cell type proportions for each tumor stage relative to WT. Two-proportion z-test with Bonferroni multiple comparisons adjustment, *=0.05>p>10-10; =10-10>p>10-20; *=p<10-20. n=44 tumor-stage/cell type groups. Statistically-insignificant proportional shifts omitted.

FIG. 16G shows unsupervised clustering of classical monocytes recapitulates intercellular heterogeneity due to metastatic progression (displayed in FIG. 10D). See FIG. 25 for differential gene expression analysis results. n=2,496 cells.

Figure 17:
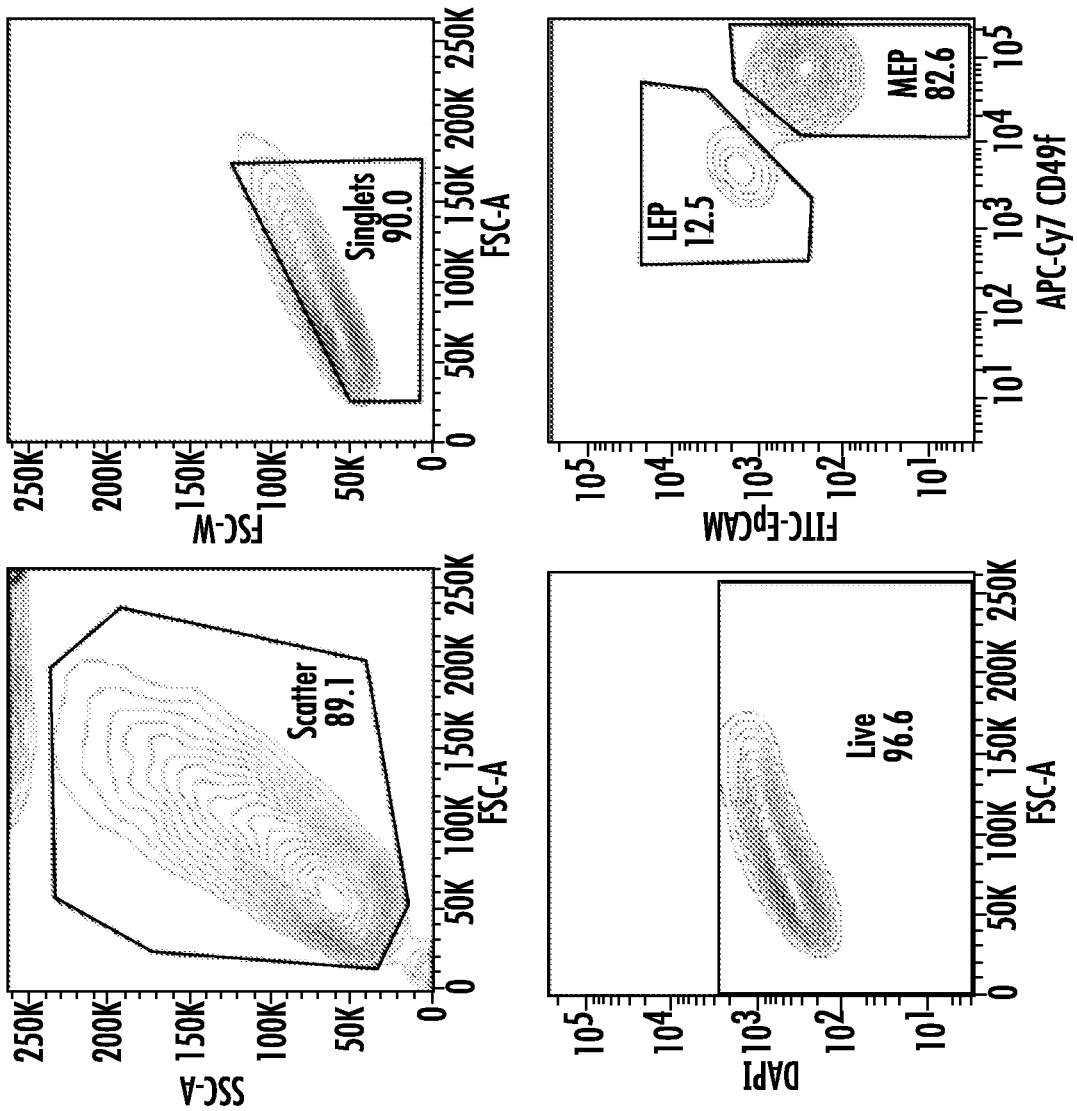
Figure 18A:
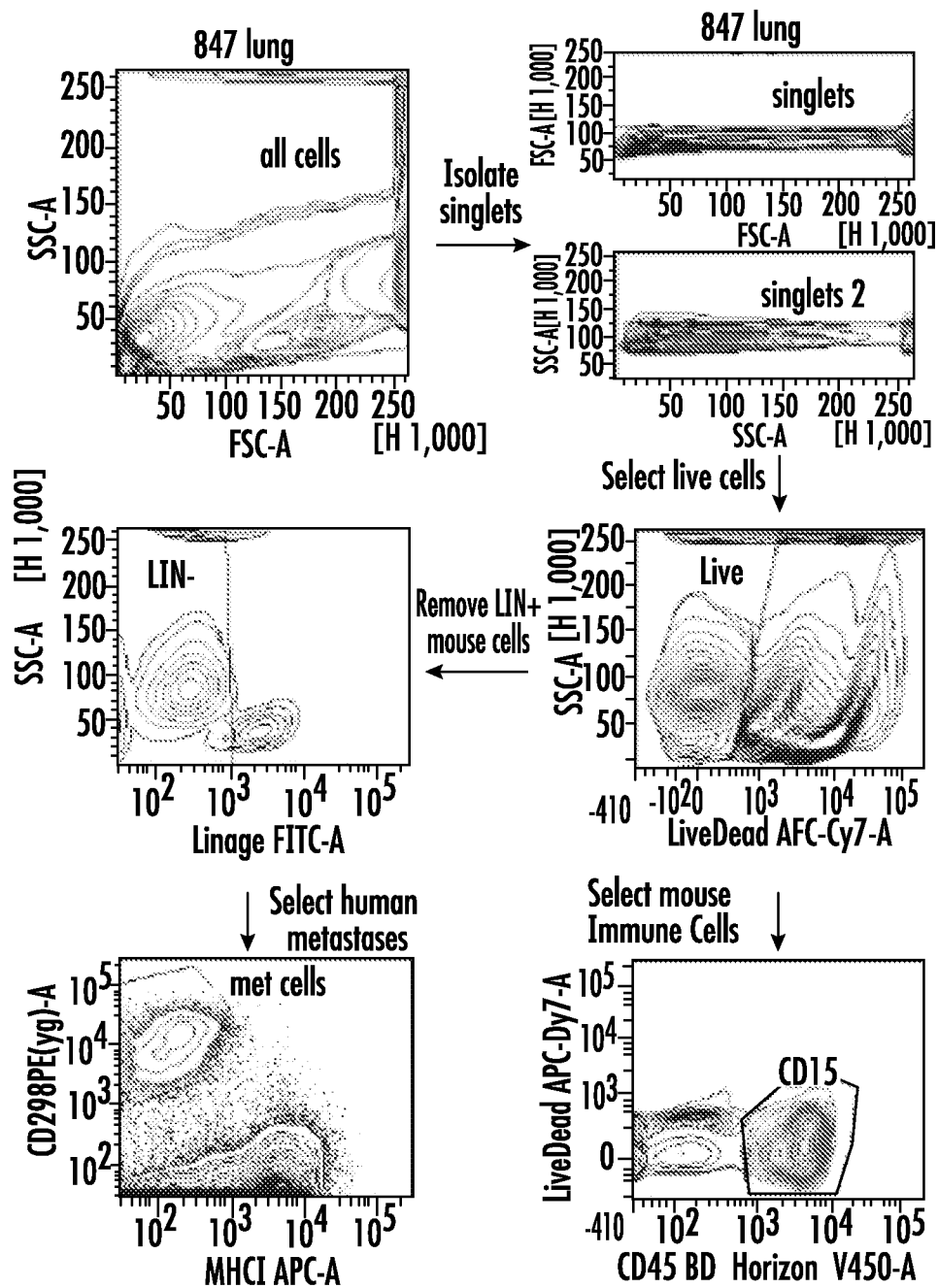

FIG. 17 shows bulk HMECs were labeled with FITC anti-EpCAM and APC-Cy7 anti-CD49f to identify and isolate LEPs and MEPs. LEPs are identified as EpCAM high and CD49f low, while MEPs are CD49f high and EpCAM low. Gating strategy causes minor cell type impurities in final sorted population FIG. 18A shows dissociated human metastases and mouse immune cells were separated from dissociate PDX mouse lungs using hCD298 and mCD45 following gating for live singlets. Mouse 847 (Sample L-A) is presented here as a representative example.

Figure 18B:
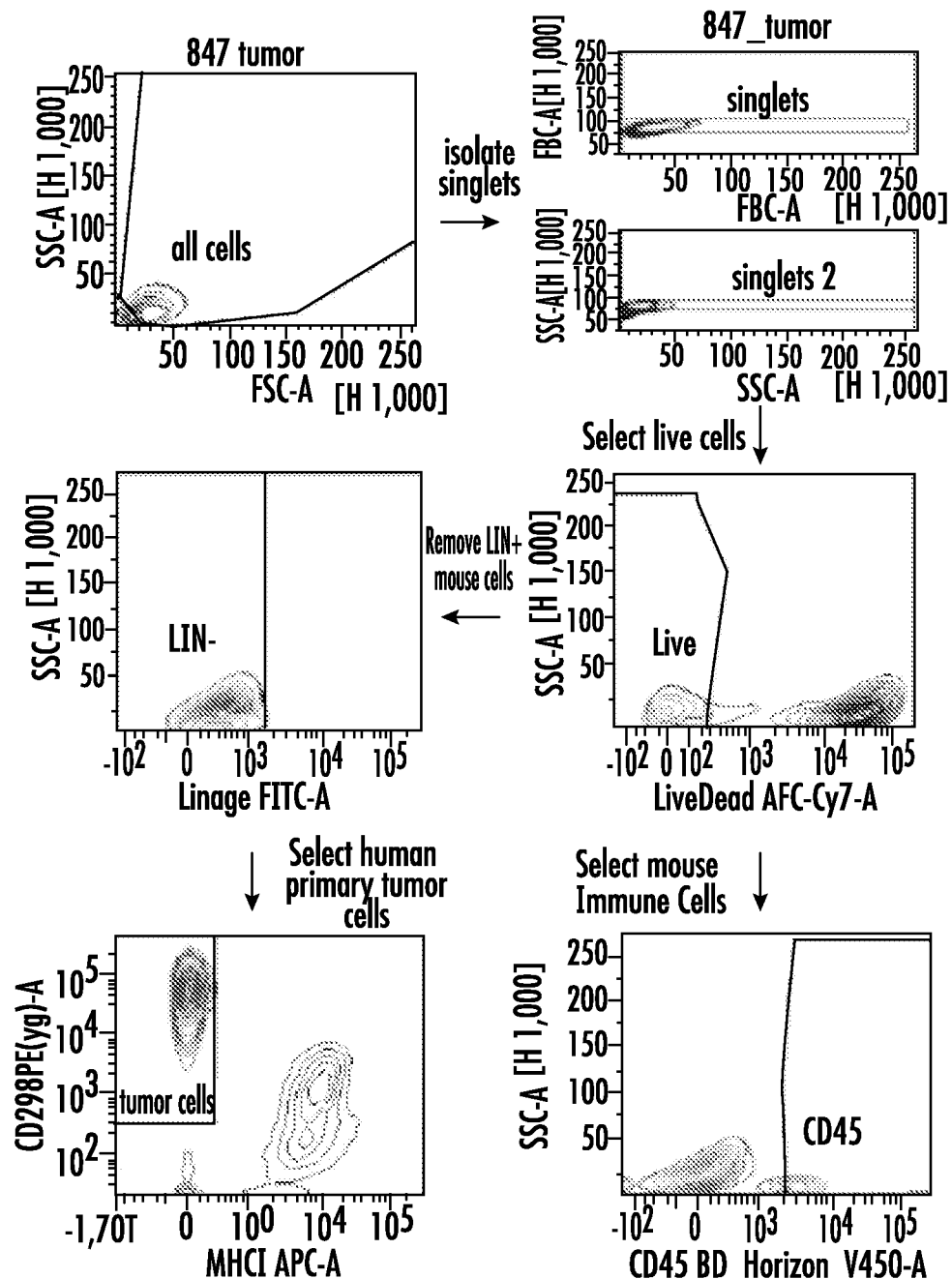

FIG. 18B shows dissociated human primary tumor cells and mouse tumor-associated immune cells were separated using hCD298 and mCD45 following gating for live, singlets. Sample A is presented here as a representative example for all other primary tumor samples.

FIG. 19A shows bioanalyzer traces following cDNA amplification and MULTI-seq barcode enrichment using 3.2×SPRI with 1.8×100% isopropanol exhibits two distinct peaks. Bioanalyzer traces are representative of all datasets presented in this study (n=4). The first peak (p1) is an average of 65-70 bp in length and likely corresponds to barcodes amplified via the MULTI-seq additive primer. The second peak (p2) is an average of 100 bp in length and likely corresponds to barcodes that successfully underwent MMLV-RTase template switching and were subsequently amplified by the standard 10× Genomics Single Cell V2 primer.

FIG. 19B shows a bioanalyzer analysis following library preparation PCR exhibits one distinct peak (p3) with an average length of 173 bp, matching expectations. Bioanalyzer traces are representative of all datasets presented in this study (n=4).

FIG. 19C shows a schematic illustrating the two species of reverse-transcribed MULTI-seq barcodes with and without template switching. Processive reverse-transcription without template switching (p1) is more likely than reverse-transcription with template switching (p2), resulting in relative enrichment of the 65-70 bp product following cDNA amplification.

FIG. 20 shows a list of genes with >1.5-fold expression difference between LMO/CMO-labeled and unlabeled HEKs, related to FIG. 8.

FIG. 21 shows MULTI-seq barcode sequencing statistics.

Figure 10F:
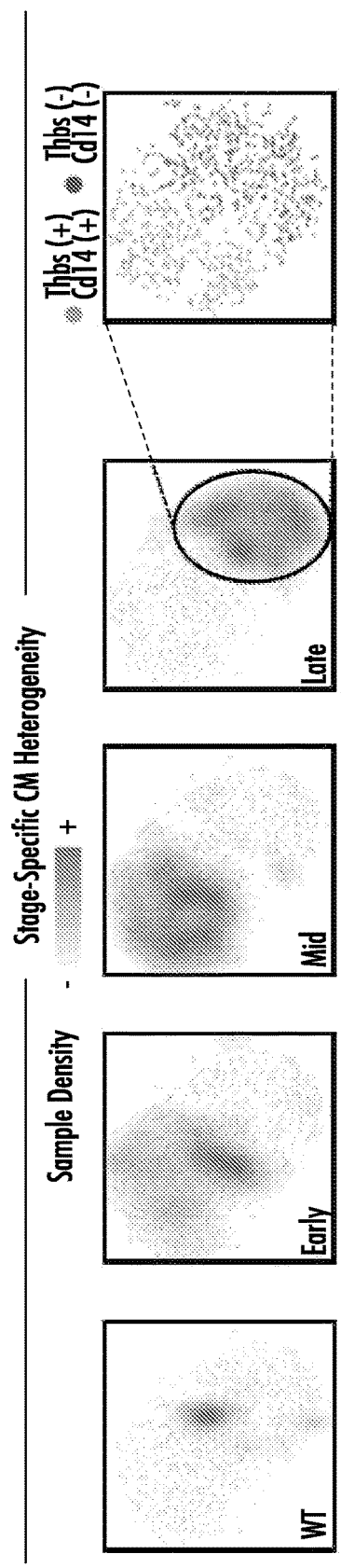
FIG. 10F shows subsetted classical monocyte gene expression space overlaid with sample classification densities corresponding to tumor stage. Inset illustrates heterogeneity within late-stage classical monocytes characterized by differential expression of Thbs1 and Cd14. n=2,496 (all), 1,087 (inset) cells.

FIG. 22 shows PDX metadata, related to FIG. 10.

FIG. 23 shows the top 5 marker genes for each low-RNA cluster within classified and unclassified datasets, related to FIG. 10.

FIG. 24 shows a list of genes with >1.5-fold expression difference between classical monocytes at distinct stages of metastatic progression, related to FIG. 10.

FIG. 25 shows a list of genes with >1.5-fold expression difference between late-stage classical monocytes, related to FIG. 10.

FIG. 26.A-26G depicts an experiment to correlate sequence expression profiles to spatial position with a sample or tissue by using unique barcoding of each 1 mm slice of tissue in segments within a series of vessels in a multiwall plate where the barcodes correspond to spatial location of expression profile in the subject.

FIG. 27A-27F depict an experiment to correlate sequence expression profiles to spatial position with a sample or tissue by using unique barcoding of each 1 cm slice of tissue in segments within a series of vessels in a multiwall plate where the barcodes correspond to spatial location of expression profile in the subject.

Figure 28:
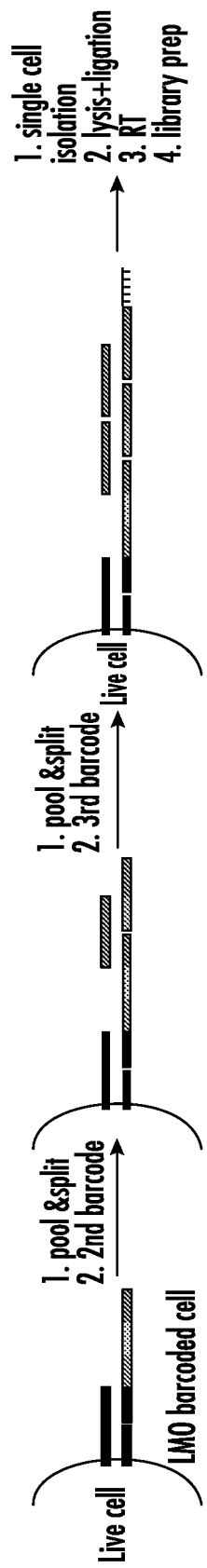

FIG. 28 shows a flow diagram for the split-pool barcoding and mRNA capture with LMOs of Example 4.

DETAILED DESCRIPTION OF EMBODIMENTS

The present disclosure provides lipid-modified or hydrophobic-anchored oligonucleotides and compositions comprising the lipid-modified or hydrophobic-anchored oligonucleotides. Also provided are methods for the synthesis of the lipid-modified or hydrophobic-anchored oligonucleotides, compositions comprising such lipid-modified or hydrophobic-anchored oligonucleotides, and the use of such lipid-modified or hydrophobic-anchored oligonucleotides and compositions thereof in, e.g., coupling single-cell RNA sequencing to chemical screens or other methods of multiplexed perturbations. The wealth of information that can be gained from single-cell RNA sequencing-based screening approaches is demonstrated with the recent development of CRISPR- and short-hairpin RNA-based genetic perturbation techniques. These methods introduce genetic-perturbation-specific barcodes in the sequencing data.

Before exemplary embodiments are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which this present disclosure belongs. Although any methods and materials similar or equivalent to those described herein can be used in the practice or testing of the disclosed embodiments, some potential and exemplary methods and materials may now be described. Any and all publications mentioned herein are incorporated herein by reference in their entireties to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a lipid-modified oligonucleotide" includes a plurality of such lipid-modified oligonucleotides and reference to "the oligonucleotide" includes reference to one or more oligonucleotides, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

Definitions

Before the present compositions and methods are described, it is to be understood that this disclosure is not limited to the particular molecules, compositions, methodologies or protocols described, as these may vary. It is also to be understood that the terminology used in the description is for the purpose of describing the particular versions or embodiments only, and is not intended to limit the scope of the present disclosure which will be limited only by the appended claims. It is understood that these embodiments are not limited to the particular methodology, protocols, cell lines, vectors, and reagents described, as these may vary. It also is to be understood that the terminology used herein is for the purpose of describing particular embodiments only, and is not intended to limit the scope of the present embodiments or claims.

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference. Nothing herein is to be construed as an admission that the disclosure is not entitled to antedate such disclosure by virtue of prior disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the phrase "integer from X to Y" means any integer that includes the endpoints. That is, where a range is disclosed, each integer in the range including the endpoints is disclosed. For example, the phrase "integer from X to Y" discloses 1, 2, 3, 4, or 5 as well as the range 1 to 5.

The term "lipid-modified oligonucleotide", "lipid-DNA", "hydrophobic-anchored oligonucleotide" and similar terms are to be broadly construed to include any oligonucleotide or polynucleotide that is attached by any means to a hydrophobic, lipophilic, or amphiphilic region that can be inserted into a membrane, regardless of whether the "lipid-modified oligonucleotide", "lipid-DNA", "hydrophobic-anchored oligonucleotide", or portion thereof is actually inserted into a membrane.

The term "membrane" or any similar term is used broadly and generically herein to refer to any lipid-containing membrane, cellular membrane, nuclear membrane, monolayer, bilayer, vesicle, liposome, lipid bilayer, etc., and the present disclosure is not meant to be limited to any particular membranes.

As used herein, the term "subject," "individual" or "patient," used interchangeably, means any animal, including mammals, such as mice, rats, other rodents, rabbits, dogs, cats, swine, cattle, sheep, horses, or primates, such as humans.

As used herein, the term "kit" refers to a set of components provided in the context of a system for sequencing nucleotides and/or isolating nucleotides sequences and/or diagnosing a subject with having a disease or infection based upon the presence, absence and/or quantity of expressed nucleotide sequences from a sample or a cell. Such systems may include, for example, systems that allow for storage, identification, or delivery of expressed genes in one or a plurality of cells (e.g., oligonucleotides, oligonucleotides that encode enzymes, extracellular matrix components etc. in appropriate containers) and/or supporting materials (e.g., buffers, media, cells, written instructions for performing the assay etc.) from one location to another. For example, in some embodiments, kits include one or more enclosures (e.g., boxes) containing relevant reaction reagents and/or supporting materials. As used herein, the term "fragmented kit" refers to a diagnostic assay comprising two or more separate containers that each contain a subportion of total kit components. Containers may be delivered to an intended recipient together or separately. For example, a first container may contain a solid support or polystyrene plate for use in a cell culture assay, while a second container may contain cells, such as control cells. As another example, the kit may comprise a first container comprising a solid support such as a chip or slide with one or a plurality of ligands with affinities to one or a plurality of biomarkers disclosed herein and a second container comprising any one or plurality of reagents necessary for the detection and/or quantification of the amount of lipid-modified oligonucleotides in a sample. The term "fragmented kit" is intended to encompass kits containing Analyte Specific Reagents (ASR's) regulated under section 520(e) of the Federal Food, Drug, and Cosmetic Act, but are not limited thereto. Any delivery system comprising two or more separate containers that each contain a sub-portion of total kit components are included in the term "fragmented kit." In contrast, a "combined kit" refers to a delivery system containing all components in a single container (e.g., in a single box housing each of the desired components). The term "kit" includes both fragmented and combined kits.

As used herein, the term "animal" includes, but is not limited to, humans and non-human vertebrates such as wild animals, rodents, such as rats, ferrets, and domesticated animals, and farm animals, such as dogs, cats, horses, pigs, cows, sheep, and goats. In some embodiments, the animal is a mammal. In some embodiments, the animal is a human. In some embodiments, the animal is a non-human mammal.

As used herein, the term "mammal" means any animal in the class Mammalia such as rodent (i.e., a mouse, a rat, or a guinea pig), a monkey, a cat, a dog, a cow, a horse, a pig, or a human. In some embodiments, the mammal is a human. In some embodiments, the mammal refers to any non-human mammal. The present disclosure relates to any of the methods or compositions of matter disclosed herein wherein the sample is taken from a mammal or non-human mammal. The present disclosure relates to any of the methods or compositions of matter disclosed herein wherein the sample is taken from a human.

As used herein, the phrase "in need thereof" means that the animal or mammal has been identified or suspected as having a need for the particular method or treatment that is needed based upon the presence, absence and/or quantity of a biomarker. In some embodiments, the identification can be by any means of diagnosis or observation. In any of the methods and treatments described herein, the animal or mammal can be in need thereof. In some embodiments, the animal or mammal is in an environment or will be traveling to an environment in which a particular disorder or condition is prevalent or more likely to occur.

The particular use of terms "nucleic acid," "oligonucleotide," and "polynucleotide" should in no way be considered limiting and may be used interchangeably herein. "Oligonucleotide" is used when the relevant nucleic acid molecules typically comprise less than about 100 bases. "Polynucleotide" is used when the relevant nucleic acid molecules typically comprise more than about 100 bases. Both terms are used to denote DNA, RNA, modified or synthetic DNA or RNA (including, but not limited to nucleic acids comprising synthetic and naturally-occurring base analogs, dideoxy or other sugars, thiols or other non-natural or natural polymer backbones), or other nucleobase containing polymers capable of hybridizing to DNA and/or RNA. Accordingly, the terms should not be construed to define or limit the length of the nucleic acids referred to and used herein, nor should the terms be used to limit the nature of the polymer backbone to which the nucleobases are attached.

Polynucleotides of the present disclosure may be single-stranded, double-stranded, triple-stranded, or include a combination of these conformations. Generally polynucleotides contain phosphodiester bonds, although in some cases, as outlined below, nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include morpholinos, locked nucleic acids (LNAs), as well as those with positive backbones, non-ionic backbones, and non-ribose backbones. Nucleic acids containing one or more carbocyclic sugars are also included within the definition of nucleic acids. These modifications of the ribose-phosphate backbone may be done to facilitate the addition of additional moieties such as labels, or to increase the stability and half-life of such molecules in physiological environments.

The term "nucleic acid sequence" or "polynucleotide sequence" refers to a contiguous string of nucleotide bases and in particular contexts also refers to the particular placement of nucleotide bases in relation to each other as they appear in a polynucleotide.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the terms "fluorogenic probe" refers to any molecule (dye, peptide, or fluorescent marker) that emits a known and/or detectable wavelength of light upon exposure to a known wavelength of light. In some embodiments, the substrates or peptides with known cleavage sites recognizable by any of the enzymes expressed by the one or plurality of animals or single-cell organisms. In some embodiments, the fluorogenic probe is attached to a any of the one or plurality of oligonucleotide sequences disclosed herein. In some embodiments, the attachment of the fluorogenic probe to the oligonucleotides disclosed herein creates a chimeric molecule capable of a fluorescent emission or emissions upon exposure of the substrate to the enzyme and the known wavelength of light, such that exposure to an enzyme creates a reaction product which is quantifiable in the presence of a fluorimeter or spectrophotometer. In some embodiments, the fluorogenic probe is fully quenched upon exposure to the known wavelength of light before enzymatic cleavage of the substrate and the fluorogenic probe emits a known wavelength of light the intensity of which is quantifiable by absorbance readings or intensity levels in the presence of a fluorimeter and, optionally, after cleavage of the probe from the oligonucleotide on which is bound. In some embodiments, the fluorogenic probe is a coumarin-based dye or rhodamine-based dye with fluorescent emission spectra measurable or quantifiable in the presence of or exposure to a predetermined wavelength of light. In some embodiments, the fluorogenic probe comprises rhodamine. In some embodiments, the fluorogenic probe comprises rhodamine-100. Coumarin-based fluorogenic probes are known in the art, for example in a U.S. Pat. Nos. 7,625,758 and 7,863,048, which are herein incorporated by reference in their entireties. In some embodiments, the fluorogenic probes are a component to, covalently bound to, non-covalently bound to, intercalated with one or a plurality of substrates to any of the enzymes disclosed herein. In some embodiments, the fluorogenic probes are chosen from ACC or AMC. In some embodiments, the fluorogenic probe is a fluorescein molecule. In some embodiments, the fluorogenic probe is capable of emitting a resonance wave detectable and/or quantifiable by a fluorimeter after exposure to one or a plurality of enzymes catalyzing the cleavage of one or a plurality of lipid-modified oligonucleotides disclosed herein.

As used herein, the term "score" refers to a single value that can be used as a component in a predictive model for the diagnosis, prognosis, or the likelihood of the presence, absence or quantity of expressed genes in a sample, wherein the single value is calculated by combining and/or normalizing raw data values with or against a control value based upon features or metrics measured in the system. In some embodiments, the score is calculated by through an interpretation function or algorithm. In some embodiments, the subject is suspected of having, is at risk of developing, or has an infection or a hyperproliferative cell.

As used herein, the term "score" refers to a single value that can be used as a component in a predictive model for the diagnosis, prognosis, or clinical treatment plan for a subject, wherein the single value is calculated by combining and/or normalizing raw data values with or against a control value based upon features or metrics measured in the system. In some embodiments, the score is calculated by through an interpretation function or algorithm. In some embodiments, the subject is suspected of having expression of a gene that promotes or contributes to the likelihood of acquiring a disease state or whose expression is correlative to the presence of a pathogen.

To facilitate the detection of a lipid-modified oligonucleotide disclosed herein, such as a detectable substance may be pre-applied to a surface, for example a plate, well, bead, or other solid support comprising one or a plurality of reaction vessels. In some embodiments, sample may be pre-mixed with a diluent or reagent before it is applied to a surface. The detectable substance may function as a lipid-oligonucleotide that is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light. In some embodiments, the lipid-modified oligonucleotide comprises a probe. In some embodiments, the detectable probe comprises or consists of a luminescent compound that produces an optically detectable signal that corresponds to the level or quantity of lipid-oligonucleotide in the sample. For example, suitable fluorescent molecules may include, but are not limited to, fluorescein, europium chelates, phycobiliprotein, phycoerythrin, phycocyanin, allophycocyanin, o-phthaldehyde, fluorescamine, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin; porphine; and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart. et al.; U.S. Pat. No. 6,004,530 to Sagner, et al.; and U.S. Pat. No. 6,582,930 to Ponomarev, et al., which are incorporated herein in their entirety by reference thereto for all purposes.

As used herein, "sequence identity" is determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). To use the term "homologus to" is synonymous with a measured "sequence identity."

As used herein, the term "sample" refers generally to a limited quantity of something which is intended to be similar to and represent a larger amount of that thing. In the present disclosure, a sample is a collection, swab, brushing, scraping, biopsy, removed tissue, or surgical resection that is to be tested for an assay or method disclosed herein. In some embodiments, samples are taken from a patient or subject that is believed to comprise a hyperproliferative cell. In some embodiments, a sample believed to contain an infection is compared to a "control sample" that is known not to contain one or plurality of cells. In some embodiments, a sample believed to contain a pathogen cell is compared to a control sample that is known to not contain a pathogen cell. In some embodiments, a sample believed to contain a hyperproliferative cell is compared to a control sample that is known not to contain a hyperproliferative cell. In some embodiments, the sample is a brushing of an environmental are or location, such as a lab bench or medical device. This disclosure contemplates using any one or a plurality of disclosed methods herein to identify, detect, and/or quantify the amount of potentially harmful expression of genes or the amount of harmful pathogens or harmful cells on a particular item or location based upon the expression of harmful genes or nucleotide sequences.

The terms "complementary" or "complementarity" refer to polynucleotides (i.e., a sequence of nucleotides) related by base-pairing rules, For example, the sequence "5'-AGT-3'," is complementary to the sequence "5'-ACT-3". Complementarity may be "partial," in which only some of the nucleic acids' bases are matched according to the base pairing rules, or there may be "complete" or "total" complementarity between the nucleic acids. The degree of complementarity between nucleic acid strands can have significant effects on the efficiency and strength of hybridization between nucleic acid strands under defined conditions. This is of particular importance for methods that depend upon binding between nucleic acid bases.

Any probe disclosed herein may be an antibody. The term "antibody" as used herein refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. As used herein, a "targeted binding agent" is an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope or antigen on the surface of a cell comprising one or more of the modified oligonucleotides disclosed herein. "Binding fragments" of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay). An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and di-sulphide stabilized variable region (dsFv). As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known See, for example, Bowie et al. *Science* 253:164 (1991), which is incorporated by reference in its entirety. Antibodies can be fragmented using conventional techniques and the fragments screened for utility in the same manner as described above for the whole antibodies. For example, F(ab')2 fragments can be generated by treating antibody with pepsin. The resulting F(ab')2 fragment can be treated to reduce disulfide bridges to produce Fab' fragments.

The invention also contemplates using one or a plurality of chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the selected antigens on the surface of differentiated cells or tumor cells. See, for example, Morrison et al., 1985; Proc. Natl. Acad. Sci. U.S.A. 81, 6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B. In any of the disclosed methods, the methods may comprise exposing any antibody that have an affinity for any of the reaction products created by cleavage of a known substrate after exposure of the substrate to any one or plurality of enzymes set forth in Table 1.

Chemical conjugation is based on the use of homo- and heterobifunctional reagents with E-amino groups or hinge region thiol groups. Homobifunctional reagents such as 5,5'-Dithiobis(2-nitrobenzoic acid) (DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridylditio)propionate (SPDP) combine exposed amino groups of antibodies and Fab fragments, regardless of class or isotype (Van Dijk et al., 1989).

Various formats may be used to test for the presence or absence of a lipid-modified oligonucleotide or nucleic acid sequence or functional fragment thereof in a sample or cell isolated from a subject using the assay devices of the present disclosure. For instance, a "sandwich" format typically involves mixing the test sample with lipid-modified nucleic acid sequences conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte or antigen on any one of the cells disclosed herein. This technique may be used to obtain quantitative or semi-quantitative results. Some examples of such sandwich-type assays are described by U.S. Pat. No. 4,168,146.

As used herein, the term "hybridization" is used in reference to the pairing of complementary nucleic acids. Hybridization and the strength of hybridization(i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence.

Hybridization is carried out in conditions permitting specific hybridization. The length of the complementary sequences, the secondary structure, and GC content affect the thermal melting point $T_m$ of the hybridization conditions necessary for obtaining specific hybridization of the target site to the target nucleic acid. Hybridization may be carried out under stringent conditions. The phrase "stringent hybridization conditions" refers to conditions under which a probe will hybridize to its target subsequence, typically in a complex mixture of nucleic acid, but to no other sequences at a detectable or significant level. Stringent conditions are sequence-dependent and will be different in different circumstances. Stringent conditions are those in which the salt concentration is less than about 1.0 M sodium ion, such as less than about 0.01 M, including from about 0.001 M to about 1.0 M sodium ion concentration (or other salts) at a pH between about 6 to about 8 and the temperature is in the range of about 20° C. to about 65° C. Stringent conditions may also be achieved with the addition of destabilizing agents, such as but not limited to formamide.

The oligonucleotide sequences, nucleic acid sequences, or other agents of the present disclosure can be administered, inter alia, as pharmaceutically acceptable salts, esters, or amides. The term "salts" refers to inorganic and organic salts of compounds of the present disclosure. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977). In some embodiments, the compositions disclosed herein comprise one or a plurality of salts of the oligonucleotide sequences disclosed herein.

The terms "thermal melting point", "melting temperature" or "$T_m$" refer herein to the temperature (under defined ionic strength, pH, and nucleic acid concentration) at which 50% of probes complementary to a target hybridize to the target sequence at equilibrium (as the target sequences are present in excess, at $T_m$, 50% of the probes are occupied at equilibrium). In some cases, the term "Td" is used to define the temperature at which at least half of a probe dissociates from a perfectly matched target nucleic acid.

The formation of a duplex molecule with all perfectly formed hydrogen-bonds between corresponding nucleotides is referred as "matched" or "perfectly matched", and duplexes with single or several pairs of nucleotides that do not correspond are referred to as "mismatched." Any combination of single-stranded RNA or DNA molecules can form duplex molecules (DNA:DNA, DNA:RNA, RNA:DNA, or RNA:RNA) under appropriate experimental conditions. Similarly, synthetic analogs can form duplex molecules with each other or RNA and DNA under the appropriate conditions.

The phrase "selectively (or specifically) hybridizing" refers to the binding, duplexing, or hybridizing of a molecule only to a particular nucleotide sequence under stringent hybridization conditions when that sequence is present in a complex mixture (e.g. total cellular or library DNA or RNA). Those of ordinary skill in the art will readily recognize that alternative hybridization and wash conditions can be utilized to provide conditions of similar stringency and will recognize that the combination of parameters is much more important than the measure of any single parameter.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (I(d) of $10^{-6}$ $M^{-1}$ or lower. "Affinity" refers to the strength of binding: increased binding affinity being correlated with a lower $K_d$.

The term "substantially similar" as used in the context of nucleic acid or amino acid sequence identity refers to two or more sequences which have at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity.

As used herein "% sequence identity" is determined using the EMBOSS Pairwise Alignment Algorithms tool available from The European Bioinformatics Institute (EMBL-EBI), which is part of the European Molecular Biology Laboratory (EMBL). This tool is accessible at the website located by placing "www," in front of "ebi.ac.uk/Tools/emboss/align/". This tool utilizes the Needleman-Wunsch global alignment algorithm (Needleman, S. B. and Wunsch, C. D. (1970) J. Mol. Biol. 48, 443-453; Kruskal, J. B. (1983) An overview of sequence comparison In D. Sankoff and B. Kruskal, (ed.), Time warps, string edits and macromolecules: the theory and practice of sequence comparison, pp. 1-44 Addison Wesley. Default settings are utilized which include Gap Open: 10.0 and Gap Extend 0.5. The default matrix "Blosum62" is utilized for amino acid sequences and the default matrix "DNAfull" is utilized for nucleic acid sequences.

The terms "operably linked" refers to a juxtaposition of two or more components (such as sequence elements), in which the components are arranged such that both components function normally and allow the possibility that at least one of the components can mediate a function that is exerted upon at least one of the other components.

"Barcode" as used herein refers to a tag or combination of tags associated with a polynucleotide the identity of which (e.g., the tag DNA sequence) can be used to differentiate polynucleotides in a sample. In certain embodiments, the barcode on a polynucleotide is used to identify the source from which the polynucleotide is derived. For example, a nucleic acid sample may be a pool of polynucleotides derived from different sources, (e.g., polynucleotides derived from different individuals, different tissues or cells, or polynucleotides isolated at different times points), where the polynucleotides from each different source are tagged with a unique barcode. As such, a barcode provides a correlation between a polynucleotide and its source. In certain embodiments, barcodes are employed to uniquely tag each individual polynucleotide in a sample. Identification of the number of unique barcodes in a sample can provide a readout of how many individual polynucleotides are present in the sample (or from how many original polynucleotides a manipulated polynucleotide sample was derived; see, e.g., U.S. Pat. No. 7,537,897, incorporated herein by reference in its entirety). Barcodes can range in length from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotide bases or more and may include multiple subunits, where each different barcode has a distinct identity and/or order of subunits. Exemplary nucleic acid tags that find use as barcodes are described in U.S. Pat. No. 7,544,473, as well as U.S. Pat. No. 7,393,665, both of which are incorporated herein by reference in their entirety for their description of nucleic acid tags and their use in identifying oligonucleotides. In certain embodiments, a set of barcodes employed to tag a plurality of samples need not have any particular common property (e.g., $T_m$, length, base composition, etc.), as the methods described herein can accommodate a wide variety of unique barcode sets. It is emphasized here that barcodes need only be unique within a given experiment. Thus, the same barcode may be used to tag a different sample being processed in a different experiment. In addition, in certain experiments, a user may use the same barcode to tag a subset of different samples within the same experiment. For example, all samples derived from individuals having a specific phenotype may be tagged with the same barcode, e.g., all samples derived from control (or wildtype) subjects can be tagged with a first barcode while subjects having a disease condition can be tagged with a second barcode (different than the first barcode). As another example, it may be desirable to tag different samples derived from the same source with different barcodes (e.g., samples derived over time or derived from different sites within a tissue). Further, barcodes can be generated in a variety of different ways, e.g., by a combinatorial tagging approach in which one barcode is attached by ligation and a second barcode is attached by primer extension. In some embodiments, multiple unique barcodes can be attached to the same sample so as to increase its uniqueness with respect to other samples. Alternatively, one barcode could represent a class of samples (e.g., a well plate), and a second or third barcode could represent a specific well within that plate. Samples can be tagged, in some embodiments, with multiple barcodes by hybridizing more than one barcode oligonucleotide to a lipid-modified or hydrophobic-anchored oligonucleotide, or samples can be labeled with multiple barcoded lipid-modified or hydrophobic-anchored oligonucleotides. In some embodiments, individual cells could be barcoded via split-pool labeling to generate a unique barcode profile that is distinct from every other cell in the pool Thus, barcodes can be designed and implemented in a variety of different ways to track polynucleotide fragments during processing and analysis, and thus no limitation in this regard is intended.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer sites, such reaction comprising one or more repetitions of the following steps: (i) denaturing the target nucleic acid, (ii) annealing primers to the primer sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQMAN®"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al., Anal. Biochem. 273:221-28 (1999) (two-color real-time PCR). Usually, distinct sets of primers are employed for each sequence being amplified.

The term "hyperproliferative cell" means a cell that is cancerous, pre-cancerous, hyperplastic, or senescent and unable to proceed through mitosis normally. In some embodiments, the hyperproliferative cell is a tumor cell. In some embodiments, the hyperproliferative cell comprises a dysfunctional cell cycle rendering it deficient in apoptosis or metabolically unstable such that the cell proliferates faster than a cell of the same type and metabolically stable.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "functional fragment" means any portion of a polypeptide or nucleic acid sequence from which the respective full-length polypeptide or nucleic acid relates that is of a sufficient length and has a sufficient structure to confer a biological affect that is at least similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the wild-type human sequence upon which the sequence is derived. In some embodiments, the functional fragment may retain 85%, 80%, 75%, 70%, 65%, or 60% sequence homology to the wild-type sequence or oligo portion of the nucleotide upon which the sequence is derived.

Lipid-Modified Oligonucleotides

The disclosure relates to a composition and a method of using the composition for a cell barcoding method that uses recently developed specific sets of lipid-conjugated or hydrophobic-anchored oligonucleotides to efficiently label single cells derived from distinct patients or test conditions. Oligonucleotide barcodes (engineered with a PCR handle, unique identifier and capture sequence) can be subsequently introduced to the cells and subsets of the cells processed for droplet microfluidics-based RNA sequencing library preparation.

Stably embedding lipid-modified oligonucleotides within the cellular plasma membrane via a two-component system is disclosed in Selden et al., J. Am. Chem. Soc. 134:765-68 (2012); Weber et al., BioMacromolecules 15:4621-26 (2014); and Published U.S. Patent Application No. 2017/0305955, each of which incorporated herein by reference in their entireties.

Figure 5:
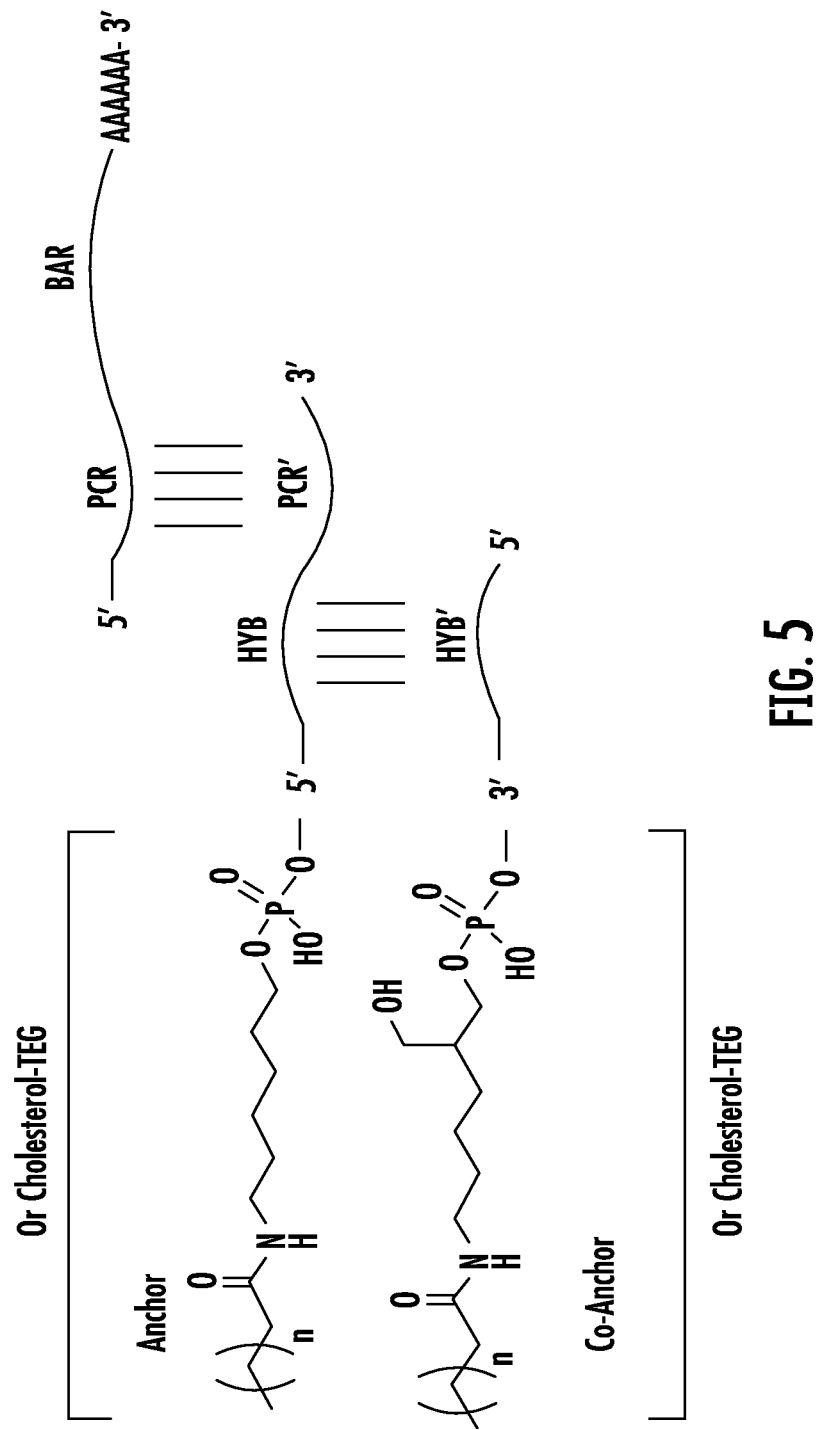
FIG. 5 shows a schematic representation of a lipid-modified oligonucleotide complex comprising an anchor lipid operably linked to the 5' end of a first DNA oligonucleotide (i.e., an "anchor" lipid-modified oligonucleotide) comprising at a hybridization sequence and a primer region; a co-anchor lipid operably linked to the 3' end of a second DNA oligonucleotide (i.e., a co-anchor lipid-modified oligonucleotide) comprising a hybridization sequence that is the reverse complement of the hybridization sequence of the first DNA oligonucleotide; and a third DNA oligonucleotide (i.e., a "barcode" oligonucleotide) comprising a primer region that is the reverse complement of the primer region of the first DNA oligonucleotide, a barcode region, and a capture sequence.

One general and non-limiting example of a lipid-modified oligonucleotide as disclosed herein is presented in FIG. 5. This lipid-modified oligonucleotide comprises three oligonucleotides: a first oligonucleotide comprising, from a 5' to 3' orientation, a first lipid moiety, a first hybridization region, and a first primer region; a second oligonucleotide comprising, from a 5' to a 3' orientation, a second hybridization region and a second lipid moiety, wherein the second hybridization region is the reverse complement of the first hybridization region; and a third oligonucleotide comprising, from a 5' to a 3' orientation, a second primer region, a barcode region, and a capture sequence, wherein the second primer region is the reverse complement of the first primer region.

The present disclosure also relates to microfluidics and labeled nucleic acids. For example, certain aspects are generally directed to systems and methods for labeling nucleic acids within microfluidic droplets or other compartments, for instance, arising from a cell. In one set of embodiments, particles may be prepared containing oligonucleotides that can be used to determine target nucleic acids, e.g., attached to the surface of the particles. The oligonucleotides may include "barcodes" or unique sequences that can be used to distinguish nucleic acids in a droplet from those in another droplet, for instance, even after the nucleic acids are pooled together or removed from the droplets. Certain embodiments of the invention are generally directed to systems and methods for attaching additional or arbitrary sequences to the nucleic acids within microfluidic droplets or other compartments, e.g., recognition sequences that can be used to selectively determine or amplify a desired sequence suspected of being present within a droplet. Such systems may be useful, for example, for selective amplification in various applications, such as high-throughput sequencing applications. Some aspects of the present disclosure are generally directed to systems and methods for containing or encapsulating nucleic acids with lipid-modified or hydrophobic-anchored oligonucleotides within microfluidic droplets or other suitable compartments, for example, microwells of a microwell plate, individual spots on a slide or other surface, or the like. The nucleic acids and the oligonucleotides may be ligated or attached together in some cases. The nucleic acids may arise from lysed cells, organelles, or other material within the droplets. The oligonucleotides within a droplet may be distinguishable from oligonucleotides in other droplets, e.g., within a plurality or population of droplets. For instance, the oligonucleotides may contain one or more unique sequences or "barcodes" that are different between the various droplets. Thus, the nucleic acid within each droplet can be uniquely identified by determining the barcodes associated with the nucleic acid. This may be important, for example, if the droplets are "broken" or ruptured and the nucleic acids from different droplets are subsequently combined or pooled together, e.g., for sequencing or other analyses.

The disclosure relates to a cell comprising one or a plurality of lipid-modified oligonucleotides, wherein the lipid-modified oligonucleotide comprises a lipid moiety region and, optionally, a capture regions. In some embodiments, the cell is a hyperproliferative cell, a transformed cell from a cell line, or a primary cell isolated from a subject or patient.

Lipid Moiety Regions

In some embodiments, the lipid moiety region comprises an alkyl chain and an alkenyl, alkyl, aryl, or aralkyl chain. This alkenyl, alkyl, aryl, or aralkyl chain may comprise about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 carbon atoms or more. In some embodiments, the alkyl chain comprises about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 carbon atoms or more, and the alkenyl, alkyl, aryl, or aralkyl chain comprises about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 carbon atoms or more. In some embodiments, the chains share the same number of carbon atoms. In other embodiments, one chain has between about 1, 2, 3, 4, 5, 6, 7, 8, 9, or 10 fewer carbon atoms than the other chain. The lipid moiety region may comprise more than one alkenyl, aryl, or aralkyl chain, with each chain comprising 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 carbon atoms or more.

In some embodiments, the lipid moiety region may contain one or more unsaturated carbon bonds. In some embodiments, the unsaturated bonds are all contained within the same chain. In still other embodiments, the unsaturated bonds may be contained in more than one chain.

In certain embodiments, the lipid moiety region comprises a dialkylphosphoglycieride, and the polynucleotide is conjugated to the dialkylphosphoglycieride. In some embodiments, each chain of the dialkylphosphoglycieride has the same number of carbon atoms with the other chain. In other embodiments, the number of carbon atoms is different between the two alkyl chains of the dialkylphosphoglycieride. In some embodiments, each chain has 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 carbon atoms or more. In some embodiments, each chain has about 12 carbon atoms, or about 14 carbon atoms, about 16 carbon atoms, about 18 carbon atoms, about 20 carbon atoms, or about 22 carbon atoms. In some embodiments, at least one chain has about 12 carbon atoms, about 14 carbon atoms, about 16 carbon atoms, about 18 carbon atoms, about 20 carbon atoms, or about 22 carbon atoms.

The lipid moiety region may comprise a monoalkylamide, and the polynucleotide may be conjugated to the monoalkylamide. In some embodiments, the monoalkylamide chain has about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 carbon atoms or more. In some embodiments, the monoalkylamide chain has about 12 carbon atoms, or about 14 carbon atoms, about 16 carbon atoms, about 18 carbon atoms, about 20 carbon atoms, or about 22 carbon atoms. In certain embodiments, the monoalkylamide comprises about 16 or 18 carbon atoms.

In other embodiments, the lipid moiety region and the polynucleotide are joined by a compound comprising, a phosphate group. In other embodiments, the lipid moiety region and the polynucleotide are joined by a compound comprising a urea group. In still other embodiments, the lipid moiety region and the polynucleotide are joined by a compound comprising a sulfonyl group. In another embodiment, the lipid moiety region and the polynucleotide are joined by a compound comprising a sulfonamide, ether, thioether, carbamate, or carbonate group.

In still other embodiments, the lipid moiety region may comprise a sterol group. In some embodiments, the sterol group may be natural or synthetic or derived from a sterol compound bearing (or modified to bear) a functional group used for attachment to the polynucleotide. For instance, sterols from biological sources are usually found either as free sterol alcohols, acylated (sterol esters), alkylated (steryl alkyl ethers), sulfated (cholesterol sulfate), or linked to a glycoside moiety (steryl glycosides) which can be itself acylated (acylated sterol glycosides) (See, e.g., Fahy et al., J. Lipid Res. 46:839-61 (2005), which reference is incorporated in its entirety). Examples include (1) sterols obtainable from animal sources, referred to herein "zoosterols" such as the zoosterols cholesterol and certain steroid hormones; and (2) sterols obtainable from plants, fungi and marine sources, referred to herein as "phytosterols," such as the phytosterols campesterol, sitosterol, stigmasterol, and ergosterol. These sterols generally bear at least one free hydroxyl group, usually at the 3 position of ring A, at another position, or combinations thereof, or can be modified to incorporate a suitable hydroxyl or other functional group as needed.

Sterols of particular interest are the simple sterols, which bear a unique functional group for attachment to the polynucleotide. Of specific interest are simple sterols in which the unique functional group is a hydroxyl, and in particular, the simple sterol alcohols having a hydroxyl group located at position 3 of ring A (e.g., cholesterol, .beta.-sitosterol, stigmasterol, campesterol, and brassicasterol, ergosterol and the like, and derivatives thereof).

Cholesterol is of particular interest in certain embodiments for inclusion in the lipid moiety region. Representative sterols of the cholesterol class (including substituted cholesterols) of interest include, for example, the following: (1) natural and synthetic sterols such as cholesterol (ovine wool), cholesterol (plant derived), desmosterol, stigmasterol, β-sitosterol, thiocholesterol, 3-cholesteryl acrylate; (2) A-ring substituted oxysterols such as cholestanol, and cholestenone; (3) B-ring substituted oxysterols such as 7-ketocholesterol, 5α,6α-epoxycholestanol, 5β,6β-epoxycholestanol, and 7-dehydrocholesterol; (4) D-ring substituted oxysterols such as 25-ketocholestene, and 15-ketocholestane; (5) side-chain substituted oxysterols such as 25-hydroxycholesterol, 27-hydroxycholesterol, 24(R/S)-hydroxycholesterol, 24(R/S),25-epoxycholesterol, and 24(S),25-epoxycholesterol; (6) lanosterols such as 24-dihydrolanosterol and lanosterol; (7) fluorinated sterols such as F7-cholesterol, F7-5α,6α-epoxycholestanol, F7-5β,6β-epoxycholostanol, and F7-7-ketocholesterol; (8) fluorescent cholesterol such as 25-NBD cholesterol, dehydroergosterol, and cholesterol triene. These compounds may also include deuterated and non-deuterated versions, and are available commercially, such as from Avanti Polar Lipids, Inc.

In certain embodiments, the lipid moiety region may comprise a saturated or unsaturated, linear or branched, substituted or unsubstituted aliphatic chain. Of particular interest are saturated or unsaturated, linear or branched, substituted or unsubstituted hydrocarbon chains having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 carbons.

Further embodiments may comprise elements based on or derivable from various lipids, such the aliphatic acids, glycerolipids, glycerophospholipids, sphingolipids, prenol lipids, polyprenol lipids, and saccharolipids, such as the from lipids described in Fahy et al., J. Lipid Res. 46:839-61 (2005).

An "anchor" lipid-modified or hydrophobic-anchored oligonucleotide (e.g., a lipid-modified oligonucleotide comprising, from a 5' to 3' orientation or from a 3' to 5' orientation, a first lipid moiety, a first hybridization region, and a first primer region) and a "co-anchor" lipid-modified or hydrophobic-anchored oligonucleotide (e.g., a lipid-modified oligonucleotide comprising, from a 5' to a 3' orientation or from a 3' to 5' orientation, a second hybridization region and a second lipid moiety, wherein the second hybridization region is the reverse complement of the first hybridization region) can comprise the same lipid moiety or a different lipid moiety (e.g., different carbon chain lengths, different compositions, or different modifications). In some embodiments, the "anchor" lipid-modified or hydrophobic-anchored oligonucleotide comprises a lipid moiety that containing the same number of carbons as the lipid moiety of the "co-anchor" lipid-modified or hydrophobic-anchored oligonucleotide. In some embodiments, the "anchor" lipid-modified or hydrophobic-anchored oligonucleotide comprises a lipid moiety that contains about 1, 2, 3, 4, 5, 6, 7, 8, 9, 10, 11, or 12 or more carbons as compared to the lipid moiety of the "co-anchor" lipid-modified or hydrophobic-anchored oligonucleotide. In some embodiments, the "co-anchor" lipid-modified or hydrophobic-anchored oligonucleotide comprises a lipid moiety that contains about 1, 2, 3, 4, 5, 6, 7, 8, 9, 10, 11, or 12 or more carbons as compared to the lipid moiety of the "anchor" lipid-modified or hydrophobic-anchored oligonucleotide. In some embodiments, the "anchor" lipid-modified or hydrophobic-anchored oligonucleotide comprises a lipid moiety that contains about 1, 2, 3, 4, 5, 6, 7, 8, 9, 10, 11, or 12 or more carbons as compared to the lipid moiety of the "co-anchor" lipid-modified or hydrophobic-anchored oligonucleotide. In some embodiments, only an anchor lipid-modified or hydrophobic-anchored oligonucleotide is used without a corresponding co-anchor lipid-modified or hydrophobic-anchored oligonucleotide.

In some embodiments, the lipid moiety (i.e., the lipid moiety in embodiments with only an anchor lipid-modified or hydrophobic-anchored oligonucleotide or either the first or second lipid moiety in embodiments with both an anchor lipid-modified or hydrophobic-anchored oligonucleotide and a co-anchor lipid-modified or hydrophobic-anchored oligonucleotide) comprises a compound of Formula I:

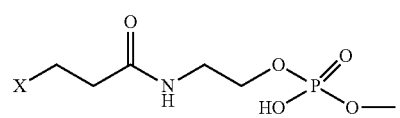

Formula I or a physiologically acceptable salt thereof,
wherein $n^1$ is from 5 to 25, $n^2$ is from 1 to 25, and X is selected from the group consisting of NH, $CH_2$, O, and CH—R, wherein R is a C12 to C28 monoglyceride, alkenyl, alkyl, aryl, or aralkyl.

In some embodiments, the lipid moiety (i.e., the lipid moiety in embodiments with only an anchor lipid-modified or hydrophobic-anchored oligonucleotide or either the first or second lipid moiety in embodiments with both an anchor lipid-modified or hydrophobic-anchored oligonucleotide and a co-anchor lipid-modified or hydrophobic-anchored oligonucleotide) comprises a compound of Formula II:

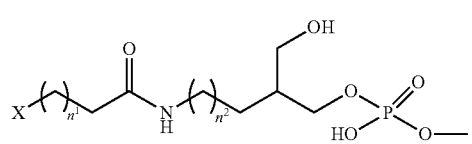

Formula II or a physiologically acceptable salt thereof,
wherein n 1 is from 5 to 25, n 2 is from 0 to 24, and X is selected from the group consisting of NH, $CH_2$, O, and CH—R, wherein R is a C12 to C28 monoglyceride, alkenyl, alkyl, aryl, or aralkyl. In some embodiments, the lipid moiety, first lipid moiety, the second lipid moiety, or both lipid moieties comprises a compound of Formula III:

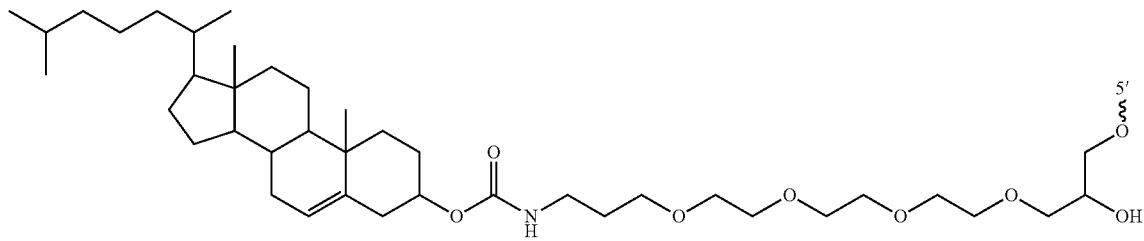

In some embodiments, the "anchor" lipid-modified or hydrophobic-anchored oligonucleotide comprises a sterol moiety and the "co-anchor" lipid-modified or hydrophobic-anchored oligonucleotide comprises a lipid moiety. In some embodiments, the "co-anchor" lipid-modified or hydrophobic-anchored oligonucleotide comprises a sterol moiety and the "anchor" lipid-modified or hydrophobic-anchored oligonucleotide comprises a lipid moiety. In some embodiments, both the "anchor" lipid-modified or hydrophobic-anchored oligonucleotide and the "co-anchor" lipid-modified or hydrophobic-anchored oligonucleotide comprises a sterol moiety.

Hybridization Regions

Anchor lipid-modified or hydrophobic-anchored oligonucleotides and co-anchor lipid-modified or hydrophobic-anchored oligonucleotides comprise hybridization regions that are complementary to each other. An anchor lipid-modified or hydrophobic-anchored oligonucleotide comprises the lipid moiety operably linked (e.g., covalently linked) to a first hybridization region comprising an oligonucleotide of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more nucleotide bases. The oligonucleotide can be DNA, RNA, or modified or synthetic DNA or RNA.

The co-anchor lipid-modified or hydrophobic-anchored oligonucleotides comprise the lipid moiety operably linked (e.g., covalently linked) to a second hybridization region comprising an oligonucleotide of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more nucleotide bases. The oligonucleotide can be DNA, RNA, or modified or synthetic DNA or RNA. In some embodiments, the second hybridization region is the same type of nucleic acid as the first hybridization region (e.g., if the first hybridization region is DNA, then the second hybridization region is DNA), or the second hybridization region can be a different type of nucleic acid compared to the first hybridization region (e.g., if the first hybridization region is DNA, then the second hybridization region could be RNA, or modified or synthetic DNA or RNA).

The second hybridization region is a reverse complement of the first hybridization region. In some embodiments, the complementarity can be perfect complementarity (i.e., the second hybridization region is the same length as the first hybridization region and each base of the second hybridization region is a perfect complement to the its basepair on the first hybridization region). In some embodiments, the first hybridization region contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 or more additional bases than the second hybridization region. In some embodiments, the second hybridization region contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 or more additional bases than the first hybridization region. In some embodiments, the first hybridization region has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to the second hybridization region.

In some embodiments, the first hybridization region has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO:4 (GTAACGATCCAGCTGT-CACT).

In some embodiments, the second hybridization region has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO:2 (AGTGACAGCTG-GATCGTTAC).

Primer Regions

Anchor lipid-modified or hydrophobic-anchored oligonucleotides and barcode oligonucleotides comprise primer regions that are complementary to each other. An anchor lipid-modified or hydrophobic-anchored oligonucleotide comprises the lipid moiety operably linked (e.g., covalently linked) to the first hybridization region which is operably linked (e.g., covalently linked) to a first primer region comprising an oligonucleotide of 10, 11, 12, 13, 14, 15, 16, 17, 18, 19, 20, 21, 22, 23, 24, 25, 26, 27, 28, 29, or 30 or more nucleotide bases. The oligonucleotide can be DNA, RNA, or modified or synthetic DNA or RNA.

The barcode oligonucleotides comprise a second primer region operably linked (e.g., covalently linked) to a barcode region (described below) which in turn is operably linked (e.g., covalently linked) to a capture sequence (described below), the second primer region comprising an oligonucleotide of 10, 11, 12, 13, 14, 15, 16, 17, 18, 19, 20, 21, 22, 23, 24, 25, 26, 27, 28, 29, or 30 or more nucleotide bases. The oligonucleotide can be DNA, RNA, or modified or synthetic DNA or RNA. In some embodiments, the second primer region is the same type of nucleic acid as the first primer region (e.g., if the first primer region is DNA, then the second primer region is DNA), or the second primer region can be a different type of nucleic acid compared to the first primer region (e.g., if the first primer region is DNA, then the second primer region could be RNA, or modified or synthetic DNA or RNA).

The second primer region is a reverse complement of the first primer region. In some embodiments, the complementarity can be perfect complementarity (i.e., the second primer region is the same length as the first primer region and each base of the second primer region is a perfect complement to the its basepair on the first primer region). In some embodiments, the first primer region contains 1, 2, 3, 4, 5, 6, 7, 8, 9, 10, 11, 12, 13, 14, 15, 16, 17, 18, 19, or 20 or more additional bases than the second primer region. In some embodiments, the second primer region contains 1, 2, 3, 4, 5, 6, 7, 8, 9, 10, 11, 12, 13, 14, 15, 16, 17, 18, 19, or 20 or more additional bases than the first primer region. In some embodiments, the first primer region has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to the second primer region.

In some embodiments, the first primer region has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO:5 (TGGAATTCTCGGGTGCCAAGG).

In some embodiments, the second primer region has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO:6 (CCTTGGCACCCGAGAAT-TCCA).

Barcode Regions

The barcode oligonucleotides comprise the second primer region operably linked (e.g., covalently linked) to a barcode region which in turn is operably linked (e.g., covalently linked) to a capture sequence (described below), the barcode region comprising an oligonucleotide of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more nucleotide bases. The oligonucleotide can be DNA, RNA, or modified or synthetic DNA or RNA. Methods of designing sets of barcode sequences are shown for example in U.S. Pat. No. 6,235,475, the contents of which are incorporated by reference herein in their entirety. Attaching barcode sequences to nucleic acid templates is shown in U.S. Pub. 2008/0081330 and U.S. Pub. 2011/0301042, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety. Barcodes for sequencing and copy number estimation are described in U.S. Pub. 2016/0046986, incorporated herein by reference in its entirety.

Barcodes can be completely random or they can be engineered with certain predetermined sequences. They may have regions of randomness or semi-randomness and other fixed regions. The barcodes may include other regions, such as priming sites, adapters, or other complimentary regions that would facilitate further processing and analysis. The identity of a specific barcode itself in relation to its second primer region can be created prior to any binding or capture of an anchor lipid-modified or hydrophobic-anchored oligonucleotide through hybridization of the first and second primer regions. Thus, in some embodiments, a database of all barcodes is created and stored, in some embodiments, on a computer storage medium.

In some embodiments, the last nucleotide of the barcode region will not be identical to the first nucleotide of the capture sequence. For example, if the capture sequence is a polyadenylation tail, the last nucleotide of the barcode region, in some embodiments, will not be adenine.

The barcode enables tagging or tracking of cells or membranes comprising the lipid-modified or hydrophobic-anchored oligonucleotides in order to permit subsequent identification and origin of the particular cell or membrane. The assignment of a barcode to individual or subgroups of oligonucleotides may allow for a unique identity to be assigned to individual sequences, fragments of sequences, or cells. This may allow acquisition of data from individual samples and is not limited to averages of samples.

In some embodiments, oligonucleotides may share a common barcode and therefore may be later identified as being derived from the same target cell. Multiple cells (of the same or different types) can be identified through use of multiple barcodes, with each barcode identifying a specific cell type or multiple cells within a specific cell type.

A single cell or membrane could comprise more than one lipid-modified or hydrophobic-anchored oligonucleotide, with each lipid-modified or hydrophobic-anchored oligonucleotide having a different first primer region. Such cells or membranes could thus be isolated and/or identified through different barcode oligonucleotides, each comprising a second primer region having complementarity to a different first primer region, and a single barcode for each barcode oligonucleotide or different barcodes for some or all of the barcode oligonucleotides.

Capture Sequence

In some embodiments, the barcode oligonucleotides comprise the second primer region operably linked (e.g., covalently linked) to the barcode region which in turn is operably linked (e.g., covalently linked) to a capture sequence (described below), the capture sequence comprising an oligonucleotide of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more nucleotide bases. The oligonucleotide can be DNA, RNA, or modified or synthetic DNA or RNA.

In some embodiments, the capture sequence is a polyadenylated tail (a "poly(A) tail"), that is, the entire capture sequence consists of adenine bases. In some embodiments, the capture sequence has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to a poly(A) tail. In some embodiments, the capture sequence has the sequence of SEQ ID NO:7 (AAAAAAAAAAAAAAAAAAAAAAAAAAAAAAAA).

In some embodiments, the capture sequence is a polythymine tail (a "poly(T) tail"), that is, the entire capture sequence consists of thymine bases. In some embodiments, the capture sequence has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to a poly(T) tail.

In some embodiments, the capture sequence is a polyuracil tail (a "poly(U) tail"), that is, the entire capture sequence consists of uracil bases. In some embodiments, the capture sequence has at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to a poly(U) tail.

In some embodiments, the capture sequence is a variant of a poly(A), poly(T), or poly(U) tail. Such variants include bases besides a pure poly(A), poly(T), or poly(U) tail. For example, variants can include capture sequences such as poly(A) variants like AAUAAA, AUUAAA AACAAG, AACAAA, AAUAAU, AAUAAG, UAUAAA, AGUAAA, AAUACA, CAUAAA, AAUAUA, GAUAAA, AAUGAA, AAGAAA, ACUAAA, AAUAGA, AAUAAU, AACAAA, AUUACA, AUUAUA, AACAAG, or AAUAAG, with each variant containing additional nucleotide bases if needed, e.g. 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 additional nucleotide bases, with the majority, and in some embodiments all, of the additional nucleotide bases being adenine. Variant poly(T) and poly(U) capture sequences can be similarly constructed.

In some embodiments, instead of a capture sequence, a member of a coupling pair (such as, e.g., antibody/antigen, receptor/ligand, or the avidin-biotin pair as described in, e.g., U.S. Patent Application No. 2006/0252077, incorporated herein by reference) may be linked to each fragment to be captured on a surface coated with a respective second member of that coupling pair. Subsequent to the capture, the sequence may be analyzed, for example, by single molecule detection/sequencing, e.g., as described in U.S. Pat. No. 7,283,337, incorporated herein by reference.

Methods of Synthesizing Lipid-Modified or Hydrophobic-Anchored Oligonucleotides

Oligonucleotides can be synthesized using protocols known in the art, for example as described in Caruthers et al., Meth. Enzymol. 211:3 (1992); WO 99/54459; Wincott et al., Nucleic Acids Res. 23:2677 (1995); Wincott et al., Meth. Mol. Bio. 74:59 (1997); Brennan et al., Biotechnol. Bioeng. 61:33 (1998); and U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end.

Oligonucleotides disclosed herein encompass native and synthetic or modified oligonucleotides. A modified nucleic acid has one or more modifications, e.g., a base modification, a backbone modification, etc., to provide the nucleic acid with a new or enhanced feature (e.g., improved stability). A nucleoside can be a base-sugar combination, the base portion of which is a heterocyclic base. Heterocyclic bases include the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In some cases, the respective ends of this linear polymeric compound can be further joined to form a circular compound. In addition, linear compounds may have internal nucleotide base complementarity and may therefore fold in a manner as to produce a fully or partially double-stranded compound. Within oligonucleotides, the phosphate groups can be referred to as forming the internucleoside backbone of the oligonucleotide. The linkage or backbone of RNA and DNA can be a 3' to 5' phosphodiester linkage.

Examples of suitable nucleic acids containing modifications include nucleic acids with modified backbones or non-natural internucleoside linkages. Nucleic acids having modified backbones include those that retain a phosphorus atom in the backbone and those that do not have a phosphorus atom in the backbone. Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity include a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid has one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in U.S. Pat. No. 5,602,240.

Also suitable are nucleic acids having morpholino backbone structures as described in, e.g., U.S. Pat. No. 5,034,506. For example, in some embodiments, a subject nucleic acid includes a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Also included are nucleic acid mimetics. The term "mimetic" as it is applied to polynucleotides encompasses polynucleotides where only the furanose ring or both the furanose ring and the internucleotide linkage are replaced with non-furanose groups, replacement of only the furanose ring is also referred to as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of suitable polynucleotide mimetic is based on linked morpholino units (morpholino nucleic acid) having heterocyclic bases attached to the morpholino ring. A number of linking groups have been reported that can link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Braasch et al., Biochemistry, 41(14): 4503-10 (2002)). Morpholino-based polynucleotides are disclosed in U.S. Pat. No. 5,034,506. A variety of compounds within the morpholino class of polynucleotides have been prepared, having a variety of different linking groups joining the monomeric subunits.

Another suitable class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 122:8595-8602 (2000)). The incorporation of CeNA monomers into a DNA chain increases the stability of a DNA/RNA hybrid. CeNA oligoadenylates formed complexes with RNA and DNA complements with similar stability to the native complexes. The incorporation CeNA structures into natural nucleic acid structures was shown by NMR and circular dichroism to proceed with conformational adaptation.

Also suitable as modified nucleic acids are Locked Nucleic Acids (LNAs) and/or LNA analogs. In an LNA, the 2'-hydroxyl group is linked to the 4' carbon atom of the sugar ring thereby forming a 2'-C,4'-C-oxymethylene linkage, and thereby forming a bicyclic sugar moiety. The linkage can be a methylene (—CH$_2$—), group bridging the 2' oxygen atom and the 4' carbon atom wherein n is 1 or 2 (Singh et al., Chem. Commun., 4:455-456 (1998)). LNA and LNA analogs display very high duplex thermal stabilities with complementary DNA and RNA (T$_m$=+3 to +10° C.), stability towards 3'-exonucleolytic degradation and good solubility properties. Potent and nontoxic oligonucleotides containing LNAs have been described (Wahlestedt et al., Proc. Natl. Acad. Sci. U.S.A., 97:5633-38 (2000)).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 54:3607-30 (1998)). LNAs and preparation thereof are also described in WO98/39352 and WO99/14226, both of which are hereby incorporated by reference in their entirety. Exemplary LNA analogs are described in U.S. Pat. Nos. 7,399,845 and 7,569,686, both of which are hereby incorporated by reference in their entirety.

A nucleic acid can also include one or more substituted sugar moieties. Suitable polynucleotides include a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Also suitable are O((CH$_2$)$_n$O)$_m$CH$_3$, O(CH$_2$)$_n$OCH$_3$, XO(CH$_2$)$_n$NH$_2$, O(CH$_2$)$_n$CH$_3$, O(CH$_2$)$_n$ONH$_2$, and O(CH$_2$)$_n$ON((CH$_2$)$_n$CH$_3$)$_2$, where n and m are from 1 to about 10. Other suitable polynucleotides include a sugar substituent group selected from: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, N$_3$, NH$_2$, heterocycloalkyl, heterocycloalkaryl, aminoalkylamino, polyalkylamino, substituted silyl, an RNA cleaving group, a reporter group, an intercalator, and other substituents having similar properties. A suitable modification can include 2'-methoxyethoxy (2'-O—CH$_2$CH$_2$OCH$_3$, also known as 2'-O-(2-methoxyethyl) or 2'-MOE) (Martin et al., Helv. Chim. Acta, 78:486-504 (1995)) i.e., an alkoxyalkoxy group. A suitable modification can include 2'-dimethylaminooxyethoxy, i.e., a O(CH$_2$)$_2$ON(CH$_3$)$_2$ group, also known as 2'-DMAOE, and 2'-dimethylaminoethoxyethoxy (also referred to as 2'-O-dimethyl-amino-ethoxy-ethyl or 2'-DMAEOE), i.e., 2'-O—CH$_2$—O—CH$_2$—N(CH$_3$)$_2$.

Other suitable sugar substituent groups include methoxy (~O—CH$_3$), aminopropoxy (~OCH$_2$CH$_2$CH$_2$NH$_2$), allyl (—CH$_2$—CH=CH$_2$),—O-allyl (—O—CH$_2$—CH=CH$_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

A nucleic acid may also include a nucleobase (also referred to as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C-CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Modified nucleobases also include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), and pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Lipids (e.g., lipid, lipids, lipid precursors, lipid precursor, oleochemicals, or oleochemical) can be produced by any chemical or biochemical (e.g., as found in U.S. Pat. Nos. 9,896,691, 9,598,710, 9,499,829, 9,428,779, 9,127,288, incorporated herein by reference in their entireties; and Kinney, 1997, Genetic Engeneering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Guhnemann-Schafer & Kindl, 1995, Biochim. Biophys Acta 1256:181-186; Kunau et al., 1995, Prog. Lipid Res. 34:267-342; Styrone et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16) and collected by any convenient method (e.g. centrifugation of extracellular secreted lipids, exposure to solvent, whole cell extraction (e.g. cell disruption and collection), hydrophobic solvent extraction (e.g. hexane), liquefaction, supercritical carbon dioxide extraction, freeze drying, mechanical pulverization, secretion (e.g. by addition of effective exporter proteins), or combinations thereof). In some embodiments, the lipids can be extracted and purified from, e.g., a plant, bacteria, or oleaginous yeast or fungi.

In some embodiments, lipids are covalently linked to the oligonucleotides disclosed herein. In some embodiments, lipids are cross-linked to the oligonucleotides disclosed herein. The manner of binding the lipids to the oligonucleotides is not particularly limited. The lipids and the oligonucleotides may be bound directly or via a linker (a linkage region). In some embodiments, the linker used to bind the lipids to the oligonucleotides comprises a nucleic acid. In some embodiments, the linker used to bind the lipids to the oligonucleotides does not comprise a nucleic acid.

The linker that can be used is not particularly limited insofar as the lipids and the oligonucleotide are covalently linked to each other. Examples of usable linkers include those of the following structures:—O—P(=O)(OH)—O—, —O—CO—O—, —NH—CO—O—, —NH—CO—NH—, —NH—$(CH_2)_{n1}$—, —S—$(CH_2)_{n1}$—, —CO—$(CH_2)_{n1}$—CO—, —CO—$(CH_2)_{n1}$—NH—, —NH—$(CH_2)_{n1}$—NH—, —CO—NH—$(CH_2)_{n1}$—NH—CO—, —C(=S)—NH—$(CH_2)_{n1}$—NH—CO—, —C(=S)—NH—$(CH_2)_{n1}$—NH—C—(=S)—, —CO—O—$(CH_2)_{n1}$—O—CO—, —C(=S)—O—$(CH_2)_{n1}$—O—CO—, —C(=S)—O—$(CH_2)_{n1}$—O—C—(=S)—, —CO—NH—$(CH_2)_{n1}$—O—CO—, —C(=S)—NH—$(CH_2)_{n1}$—O—CO—, C(=S)—NH—$(CH_2)_{n1}$—O—C—(=S)—, —CO—NH—$(CH_2)_{n1}$—O—CO—, —C(=S)—NH—$(CH_2)_{n1}$—CO—, —C(=S)—O—$(CH_2)_{n1}$—NH—CO—, —C(=S)—NH—$(CH_2)_{n1}$—O—C—(=S)—, —NH—$(CH_2CH_2O)_{n2}$—CH$(CH_2OH)$—, —NH—$(CH_2CH_2O)_{n2}$—CH$_2$—, —NH—$(CH_2CH_2O)_{n2}$—CH$_2$—CO—, —O—$(CH_2)_{n3}$—S—S—$(CH_2)_{n4}$—O—P(=O)$_2$—, —CO—$(CH_2)_{n3}$—O—CO—NH—$(CH_2)_{n4}$—, —CO—$(CH_2)_{n3}$—CO—NH—$(CH_2)_{n4}$—, wherein n1 is an integer from about 1 to about 40, n2 is an integer from about 1 to about 20, and, n3 and n4 may be the same or different, and are an integer from about 1 to about 20. In some embodiments, the linker is a phosphate group (—O—P(=O)(OH)—O—).

Membranes

Another aspect of the present disclosure relates to composition comprising membrane, particles or beads comprising a lipid-modified or hydrophobic-anchored oligonucleotide disclosed herein. In some embodiments, the membrane is a biological membrane (e.g., a lipid bilayer surrounding a biological compartment such as a cell, including artificial cells, or a membrane vesicle or sheet or cell internal compartments such as nuclei, mitochondria, and peroxisomes). In some embodiments, the membrane is part of a living cell. In other embodiments, the membrane is an artificial (synthetic) membrane, e.g., a planar membrane, a liposome, etc. Membranes may be isolated membranes. In some embodiments, a membrane is affixed to a surface.

In some embodiments, the artificial membrane is a lipid bilayer. In other embodiments, the artificial membrane is a lipid monolayer. In some embodiments, the artificial membrane is part of a liposome. Liposomes include unilamellar vesicles composed of a single membrane or lipid bilayer, and multilamellar vesicles (MLVs) composed of many concentric membranes (or lipid bilayers).

Artificial membranes, and methods of making same, have been described in the art. See, e.g., U.S. Pat. No. 6,861,260; Kansy et al. (1998) J. Med. Chem. 41(7):1007-10; and Yang et al. (1996) Advanced Drug Delivery Reviews 23:229-256.

A subject artificial membrane will in some embodiments, include one or more phospholipids. In some embodiments, the artificial membrane comprises a mixture of phospholipids containing saturated or unsaturated mono or disubstituted fatty acids and a combination thereof. These phospholipids are in some embodiments selected from dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphandylserine, palmitoyloleoylphosphatidylethanolamine, palmitoyloleoylphophatidylglycerol, palmitoyloleoylphosphatidic acid, palmitelaidoyloleoylphosphatidylcholine, paimitelaidoyloleoylphosphatidylserine, palmitelaidoyloleoylphosphatidylethanolamine, pahnitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidyiglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, and palmiticlinoleoylphosphatidic acid. Suitable phospholipids also include the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidyiglycerol) and phosphatidic acid (lysophosphatidic acid), The monoacyl chain in such lysophosphatidyl derivatives will in some embodiments be palimtoyl, oleoyl, palmitoleoyl, linoleoyl myristoyl or myristoleoyl.

Methods of Use

Lipid-modified or hydrophobic-anchored oligonucleotide compounds and lipid-modified or hydrophobic-anchored oligonucleotide-containing compositions can be used in a variety of different pharmaceutical, cosmeceutical, diagnostic and biomedical applications. Non-limiting examples of such uses are described below.

For example, lipid-modified or hydrophobic-anchored oligonucleotide compounds and compositions comprising lipid-modified or hydrophobic-anchored oligonucleotide compounds find use in research and therapeutic applications, including the study of cell-cell interactions, membrane mechanics, the bottom-up assembly of tissues, the quantitative imaging of non-adherent cells, or the study of biological processes occurring near a cell surface.

In practicing such methods, a composition comprising a lipid-modified or hydrophobic-anchored oligonucleotide may first be contacted with a membrane under conditions allowing insertion of said composition into said membrane. In some embodiments, the method comprises contacting a membrane with a composition comprising a lipid-modified or hydrophobic-anchored oligonucleotide and incubating said composition with said lipid membrane under conditions allowing insertion of said composition into said membrane.

In some embodiments, anchor lipid-modified or hydrophobic-anchored oligonucleotides and co-anchor lipid-modified or hydrophobic-anchored oligonucleotides are added to cells or membranes simultaneously. In some embodiments anchor lipid-modified or hydrophobic-anchored oligonucleotides and co-anchor lipid-modified or hydrophobic-anchored oligonucleotides are added to cells or membranes sequentially, i.e. anchor lipid-modified or hydrophobic-anchored oligonucleotides added to cells or membranes first followed by addition of co-anchor lipid-modified or hydrophobic-anchored oligonucleotides to the cells or membranes or co-anchor lipid-modified or hydrophobic-anchored oligonucleotides added to cells or membranes first followed by addition of anchor lipid-modified or hydrophobic-anchored oligonucleotides to the cells or membranes.

In some embodiments, the disclosure relates to a method of labeling a cell, a method of isolating endogenous DNA from a single cell, or a method of sequencing nucleic acid sequences within a single cell comprising exposing a single cell to one or a plurality of anchor lipid-modified oligonucleotides, then adding at least a first labeling oligonucleotide sequence complementary to the anchor-lipid modified oligonucleotide, the first labeling oligonucleotide sequence comprising a known nucleic acid sequence portion on its 3' region. In some embodiments, the first labeling oligonucleotide is complementary to the 3' region of the anchor-lipid modified oligonucleotide such that at least a portion of the known nucleic acid sequence of the 3' end is single-stranded. In some embodiments, the method further comprises exposing the single-stranded 3' end of the first labeling oligonucleotide to a ligase buffer and a ligase to covalently link the first labeling oligonucleotide to the anchor lipid-modified oligonucleotide. The anchor-lipid modified oligonucleotide may be exposed sequentially to at least a second, third or fourth or more labeling oligonucleotide, each of the first, second, third, fourth or more oligonucleotides comprising a unique identifying nucleic acid sequence in their respective 3' region of the molecule. In some embodiments, the method further comprises exposing the anchor lipid-modified oligonucleotides and the first or plurality of labeling oligonucleotides to a first linker, such oligonucleotide sequence complementary to a portion of the first labeling oligonucleotide and the second labeling oligonucleotide, such that, when exposed to ligase and free dNTPs, the first linker serves as a template nucleic acid strand for ligating and forming complementary nucleic acid sequence along a strand of nucleic acid of that is single-stranded region of the 3' end of each labeling oligonucleotide. In some embodiments, the disclosure relates to a method of labeling a cell, a method of isolating endogenous DNA from a single cell, or a method of sequencing nucleic acid sequences from a single cell comprises:

(a) exposing a cell to one or a plurality of anchor-lipid modified oligonucleotides for a time period sufficient for the anchor-lipid modified oligonucleotide to embed itself within a cell membrane of the cell;

(b) exposing the cell to one or a plurality of labeling oligonucleotides complementary to the anchor-lipid modified oligonucleotides for a time period sufficient for the anchor-lipid modified oligonucleotide to form a complementary strand of nucleic acid with the one or plurality of labeling oligonucleotides;

(c) ligating the one or plurality of labeling oligonucleotides to the one or plurality of anchor-lipid modified oligonucleotides; and, optionally (d) detecting the presence of the one or plurality of labeling oligonucleotides by detection of one of more unique nucleotide sequences corresponding to the one or plurality of labeling oligonucleotides; and/or (e) isolating the cell based upon the presence one or plurality of labeling oligonucleotides, wherein the presence of the one or plurality of labeling oligonucleotides is determined by detection of one of more unique nucleotide sequences corresponding to the one or plurality of labeling oligonucleotides.

In some embodiments, the method of labeling a cell, a method of isolating endogenous DNA from a single cell, or a method of sequencing nucleic acid sequences from a single cell comprises:

(a) exposing a cell to one or a plurality of anchor-lipid modified oligonucleotides for a time period sufficient for the anchor-lipid modified oligonucleotide to embed itself within a cell membrane of the cell;

(b) exposing the cell to a first labeling oligonucleotides complementary to the anchor-lipid modified oligonucleotides for a time period sufficient for the anchor-lipid modified oligonucleotide to form a complementary strand of nucleic acid with the one or plurality of labeling oligonucleotides;

(c) ligating the one or plurality of labeling oligonucleotides to the first anchor-lipid modified oligonucleotides; and, optionally (d) detecting the presence of the first labeling oligonucleotides by detection of one of more unique nucleotide sequences corresponding to the first labeling oligonucleotides; and/or (e) isolating the cell based upon the presence the first labeling oligonucleotides, wherein the presence of the one or plurality of labeling oligonucleotides is determined by detection of one of more unique nucleotide sequences corresponding to the first labeling oligonucleotides.

In some embodiments, the method of labeling a cell, a method of isolating endogenous DNA from a single cell, or a method of sequencing nucleic acid sequences from a single cell comprises:

(a) exposing a cell to one or a plurality of anchor-lipid modified oligonucleotides for a time period sufficient for the anchor-lipid modified oligonucleotide to embed itself within a cell membrane of the cell;

(b) exposing the cell to a first, second, third fourth or more labeling oligonucleotides, wherein the first labeling oligonucleotide is complementary to the one or a plurality of anchor-lipid modified oligonucleotides and exposed to the one or a plurality of anchor-lipid modified oligonucleotides for a time period sufficient for the anchor-lipid modified oligonucleotide to form a complementary strand of nucleic acid with the first labeling oligonucleotide, and wherein the second, third and/or fourth or more labeling oligonucleotides is exposed sequentially to a 3' portion of the labeling oligonucleotide exposed to the cell immediately prior to the second, third and/or fourth or more labeling oligonucleotides are exposed to the cell and for a time period sufficient for the second, third and/or fourth or more labeling oligonucleotides to covalently or non-covalently bind to the prior exposed labeling oligonucleotide;

(c) ligating the one or plurality of labeling oligonucleotides to the first anchor-lipid modified oligonucleotides and, in the case of the second, third, fourth or more labeling oligonucleotides ligating the labeling oligonucleotides simultaneously to one another; and, optionally (d) detecting the presence of the first, second, third, fourth and/or more labeling oligonucleotides by detection of one of more unique nucleotide sequences corresponding to each of the first, second, third, fourth labeling oligonucleotides; and/or (e) isolating the cell based upon the presence the first, second, third, fourth and/or more labeling oligonucleotides or on the sequential combination of unique nucleotide sequences of each of the first, second, third, fourth and/or more labeling oligonucleotides, wherein the presence of the first, second, third, fourth and/or more labeling oligonucleotides is determined by detection of one of more unique nucleotide sequences corresponding to the one or a combination of each of the labeling oligonucleotides.

In some embodiments, the disclosure relates to a method of labeling a plurality of cells from a sample, and, if the method comprises exposing the cell to a plurality of labeling oligonucleotides, the method further comprises a step of pooling the cells in a single vessel before exposing the cell to each sequential step of exposure to a second, third, fourth or more labeling oligonucleotide.

In one aspect, microfluidic droplets are used, for example, to contain cells. Microfluidic droplets may be used to keep the cells of a plurality of cells separate and identifiable, e.g., such that differences between the different cells may be identified. A plurality of cells, some or all of which may contain individual differences, may be studied, at resolutions down to the single-cell level, for example, by using the lipid-modified or hydrophobic-anchored oligonucleotides disclosed herein.

The cells may arise from any subject, e.g., a human, or from a non-human animal, for example, an invertebrate cell (e.g., a cell from a fruit fly), a fish cell (e.g., a zebrafish cell), an amphibian cell (e.g., a frog cell), a reptile cell, a bird cell, or a mammal cell, such as a monkey, ape, cow, sheep, goat, horse, donkey, camel, llama, alpaca, rabbit, pig, mouse, rat, guinea pig, hamster, dog, cat, etc. If the cell is from a multicellular organism, the cell may be from any part of the organism. In some embodiments, a tissue may be studied. For example, a tissue from an organism may be processed to produce cells (e.g., through tissue homogenization or by laser-capturing the cells from the tissue), such that the differences within the tissue may be determined, as discussed herein.

The cells or tissues may arise from a healthy subject, or one that is diseased or suspected of being diseased. For example, blood cells from a subject may be removed and studied to determine differences or changes in the profile of those cells, e.g., to determine if the subject is healthy or has a disease, for example, if the animal has cancer (e.g., by determining cancer cells within the blood). In some cases, a tumor may be studied (e.g., using a biopsy), and the profile of the tumor may be determined. For instance, the cells may be studied to determine if any of the cells are cancer stem cells.

The cells may also be determined using other techniques, in addition to the ones discussed herein, which may assist in determining the epigenetic profile of the cells. For example, the cells may be studied using flow cytometry, microscopy, the cells may be cultured, etc., to determine whether the profile (or changes in the profile) correlate to other changes in the cell, for example, expression levels of a protein, changes in morphology, ability to reproduce or differentiate, etc.

The droplets may be contained in a microfluidic channel. For example, in certain embodiments, the droplets may have an average dimension or diameter of less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 10 micrometers, less than about 5 micrometers, less than about 3 micrometers, or less than about 1 micrometer in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain instances. The droplets may be spherical or non-spherical. The average diameter or dimension of a droplet, if the droplet is non-spherical, may be taken as the diameter of a perfect sphere having the same volume as the non-spherical droplet.

The droplets may be produced using any suitable technique. For example, a junction of channels may be used to create the droplets. The junction may be, for instance, a T-junction, a Y-junction, a channel-within-a-channel junction (e.g., in a coaxial arrangement, or comprising an inner channel and an outer channel surrounding at least a portion of the inner channel), a cross (or "X") junction, a flow-focus junction, or any other suitable junction for creating droplets. See, for example, WO 2004/091763 and WO 2004/002627, each of which is incorporated herein by reference in its entirety. In some embodiments, the junction may be configured and arranged to produce substantially monodisperse droplets.

In some cases, the cells may be encapsulated within the droplets at a relatively high rate. For example, the rate of cell encapsulation in droplets may be at least about 10 cells/s, at least about 30 cells/s, at least about 100 cells/s, at least about 300 cells/s, at least about 1,000 cells/s, at least about 3,000 cells/s, at least about 10,000 cells/s, at least about 30,000 cells/s, at least about 100,000 cells/s, at least about 300,000 cells/s, or at least about $10^6$ cells/s.

PCR reactions (including, for example, reverse transcription PCR and primer extension PCR utilizing the lipid-modified or hydrophobic-anchored oligonucleotides disclosed herein) can be performed using, e.g., any microfluidic device (including, e.g., microfluidic devices interfaced with a multisample nanodispenser). Microfluidic devices are fluid systems in which the volumes of fluid are small, typically on the order of microliters to nanoliters. In some embodiments the microfluidics can handle tens to thousands of samples in small volumes. Microfluidics can be active or passive. By using active elements such as valves in the microfluidic device, microfluidic circuits can be created. This allows not only the use of small reagent volumes but also a high task parallelization since several procedures can be processed and physically be fitted on the same chip.

In microfluidic channels the flow of liquid can be completely laminar, that is, all of the fluid moves in the same direction and at the same speed. Unlike turbulent flow this allows the transport of molecules in the fluid to be very predictable. Microfluidic devices can be made of glass or plastic. In some embodiments, polydimethylsiloxane (PDMS), a type of silicone can be used. Some advantages of PDMS are that it is inexpensive, optically clear and permeable to several substances, including gases. In some embodiments soft lithography or micromolding can be used to create PDMS based microfluidic devices. The devices can use pressure driven flow, electrodynamic flow, or wetting driven flow.

In some embodiments, the microfluidic device has multiple chambers, each chamber having a real-time microarray. In some embodiments, the array is incorporated into the microfluidic device. In some embodiments, the microfluidic device is formed by adding features to a planar surface having multiple real-time microarrays in order to create chambers wherein the chamber correspond to the real-time microarray. In some embodiments, a substrate having 3-dimensional features, for example a PDMS surface with wells and channels, is placed in contact with a surface having multiple real-time microarrays to form a microfluidic device having multiple arrays in multiple chambers.

A device having multiple chambers, each with a real-time microarray can be used in order to analyze multiple samples simultaneously. In some embodiments, multiple chambers have sample fluid derived from the same sample. Having sample fluid from the same sample in multiple chambers can be useful, for example to measure each with different arrays for analyzing different aspects of the same sample, or for example for increasing accuracy by parallel measurements on identical arrays. In some cases, different amplicons within the same sample will have different optimum temperature profile conditions. Thus, in some embodiments, the same sample is divided into different fluid volumes, and the different fluid volumes are in different chambers with real-time microarrays; and at least some of the different fluid volumes are given a different temperature cycle.

In some embodiments, multiple chambers have sample fluid from different sources. Having sample fluid from different sources can be useful in order to increase throughput by measuring more samples in a given time period on a given instrument. In some embodiments, the microfluidic with multiple chambers containing real-time microarrays can be used for diagnostic applications. The device may have about 2, 3, 4, 5, 6, 7, 8, 9, 10, 10-15, 15-20, 20-30, 30-50, 50-75, 75-100, or more than 100 chambers each having a real time microarray.

Some embodiments relate to use of the lipid-modified or hydrophobic-anchored oligonucleotides in conjunction with solid supports. "Solid support" refers to any substrate having a surface to which molecules may be attached, directly or indirectly, through either covalent or non-covalent bonds. The solid support may include any substrate material that is capable of providing physical support for the probes that are attached to the surface. The material is generally capable of enduring conditions related to the attachment of the barcode oligonucleotides to the surface and any subsequent treatment, handling, or processing encountered during the performance of an assay. The materials may be naturally occurring, synthetic, or a modification of a naturally occurring material. Suitable solid support materials may include silicon, graphite, mirrored surfaces, laminates, ceramics, plastics (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the a rt that are capable of having one or more functional groups, such as any of an amino, carboxyl, thiol, or hydroxyl functional group, for example, incorporated on its surface, are also contemplated.

The material used for a solid support may take any of a variety of configurations ranging from simple to complex. The solid support can have any one of a number of shapes, including a strip, plate, disk, rod, particle, including bead, tube, well, and the like. Usually, the material is relatively planar such as, for example, a slide, though it can be spherical, such as, for example, a bead, or cylindrical (e.g., a column). In many embodiments, the material is shaped generally as a rectangular solid. Multiple predetermined arrangements such as, e.g., arrays of probes, may be synthesized on a sheet, which is then diced, i.e., cut by breaking along score lines, into single array substrates. Exemplary solid supports that may be used include microtiter wells, microscope slides, membranes, magnetic beads, charged paper, Langmuir-Blodgett films, silicon wafer chips, flow through chips, and microbeads. In some embodiments, the beads are plastic or polystyrene. In some embodiments, the beads are magnetic. After exposure of the beads to a magnetic force, nucleic acid molecules or sequences form the cells are capable of being isolated. Individual DNA and RNA Direct conjugation of the barcode oligonucleotide via its capture sequence, such as a poly(A) tail, to the solid support is possible in some embodiments. In such embodiments, cells or membranes comprising the anchor and co-anchor lipid-modified or hydrophobic-anchored oligonucleotides can be exposed to the solid support in hybridizing conditions such that cells or membranes comprising the anchor and co-anchor lipid-modified or hydrophobic-anchored oligonucleotides bind to the barcode oligonucleotide. The solid support can then be washed of non-binding substances and remaining solid support including bound cells and membranes further analyzed by sequencing or other identification scheme.

In some embodiments, the solid support is unbound initially and binds to a barcode oligonucleotide through the barcode oligonucleotide's capture sequence. In such embodiments, cells or membranes comprising the anchor and co-anchor lipid-modified or hydrophobic-anchored oligonucleotides have already hybridized to the barcode oligonucleotide through the first and second primer regions. The solid support can then be washed of non-binding substances and remaining solid support including bound cells and membranes further analyzed by sequencing or other identification scheme.

In some embodiments, the disclosure relates to a method of labeling a cell with a barcode or lipid-modified oligonucleotide disclosed herein. In some embodiments, the methods comprise contacting one or a plurality of homogenous mixture or heterogenous mixture of the disclosed oligonucleotides with one or a plurality of cells. In some embodiments, the cells are from a sample. In some embodiments, the cells are contacted with at least a first and a second lipid-modified oligonucleotide, such that the lipid-oligonucleotide hybridizes with an RNA, DNA, or RNA/DNA hybrid present in the cell. In some embodiments, the capture region of the oligonucleotide is used to isolate the oligonucleotide to a solid support or another fixed oligonucleotide such that unhybridized elements or components from the cells may be removed and a retentate of the captured RNA/DNA from the cell is preserved. In some embodiments, the captured RNA/DNA from a single cell may be isolated in a culture vessel. In some embodiments, a plurality of captured DNA/RNA sequences may be maintained in a library corresponding to the cell from which it was isolated. In some embodiments, the plurality of captured DNA/RNA sequences are sequenced, such that the sequenced DNA or RNA corresponds to an expression pattern of that cell.

The disclosure relates to a method of preparing a library of oligonucleotides expressed by a single cell or multiple cells in isolation, the method of generating the library comprising sequencing RNA or DNA from the one or multiple cells after the one or multiple cells are exposed to one or a plurality of lipid-modified oligonucleotides disclosed herein. In some embodiments, endogenous nucleotides from one or a plurality of cells can be isolated and/or identified by correlating a known signal or frequency of a probe bound to the lipid-modified oligonucleotide to the cell upon which the oligonucleotide was bound. The signal or frequency of the probe can be paired with the source of the endogenous DNA and/or RNA. In some embodiments, the endogenous nucleotides are expressed mRNA from the one or plurality of cells or cDNA that has been formed from constructing a library of complementary strand of DNA by, for example, PCR or other known technique to create cDNA library from isolated mRNA. In some embodiments, cDNA or mRNA isolated from a single cell by contacting the cell to one or plurality of lipid-modified oligonucleotide disclosed herein such that each cell captured can be correlated to the identify, number or detection of a probe bound to the lipid-modified oligonucleotide or oligonucleotides. Different distributions of one or a plurality of lipid-modified oligonucleotides on one or plurality of cells can be used to correlate that cell with its particular set of endogenous expression patterns. Cells carrying one or two or more lipid-modified oligonucleotides may be isolated using an antibody specific for an antigen or other protein on the surface of the cells. An expression pattern of a cell (created by sequencing one or a plurality od endogenous sequences expressed by the cell) can be correlated to a corresponding identity of a cell with a known antigen identified by adhesion of an antibody known to bind the target sequence of the antibody.

Kits

Kits and systems are provided which can facilitate the production and/or use of the compositions disclosed herein. Kits contemplated herein can include one or more of a lipid-modified or hydrophobic-anchored oligonucleotide, compositions comprising lipid-modified or hydrophobic-anchored oligonucleotides, an agent of interest for delivery, which may be provided in separate containers or, more usually, in a single composition in a sterile container.

In addition, the kit can contain instructions for using the components of the kit.

In some embodiments, the kits comprise a multiwell plate, e.g. a 96-, 384-, 1536- or 3456-well plate, containing anchor lipid-modified or hydrophobic-anchored oligonucleotides pre-hybridized to sample barcodes. Cells derived from distinct patients, conditions, etc. could be barcoded via dispensing into unique wells, upstream of co-anchor labeling, washing, and single-cell RNA sequencing.

EXAMPLES

Example 1

Lignoceric acid moiety (LMO) or Cholesterol-TEG (CMO) were adapted from the barcode design from Cite-Seq (Stoekius et al., Nat. Meth. 14:865-68 (2017)) for LMOs/CMOs, synthesizing/ordering the following materials:

(1) A 41 nt "anchor" DNA oligo coupled at the 5' end to a lignoceric acid moiety (LMO) or Cholesterol-TEG (CMO). The most 5' 20 nts are the reverse complement of co-anchor sequence (see below) and stabilize membrane labeling. The downstream 21 nts are the reverse complement of the TruSeq Small RNA PCR handle located at the 5' end of the unmodified DNA barcode (see below). The LMO/CMO anchor sequences are as follows:

5'-{24C.FA}-GTAACGATCCAGCTGTCACTTGGAATTCTCGGGTGCCAAGG-3'

5'-{Chol-TEG}-GTAACGATCCAGCTGTCACTTGGAATTCTCGGGTGCCAAGG-3'

(2) A 20 nt "co-anchor" DNA oligo coupled at the 3' end to a palmitic acid moiety (LMO) or Cholesterol-TEG (CMO). The co-anchor is the reverse complement of the 5' end of the anchor and have the following sequences:

```
5'-AGTGACAGCTGGATCGTTAC-{16C.FA}-3'

5'-AGTGACAGCTGGATCGTTAC-{TEG-Chol}-3'
```

(3) A set of 59 nt scRNAseq barcodes, each of which are localized to cells via hybridization to the 3' end of the anchor sequence. The hybridization region is the TruSeq Small RNA PCR handle, which is used for PCR-based enrichment of barcodes during library preparation. The barcode includes a 6 nt sample barcode and a 32 nt poly-A region for capture on scRNAseq mRNA capture beads. The barcodes have the following sequence:

```
5'-CCTTGGCACCCGAGAATTCCANNNNNNAAAAAAAAAAAAAAAAAAAA
AAAAAAAAAAAA-3'
```

Figure 1:
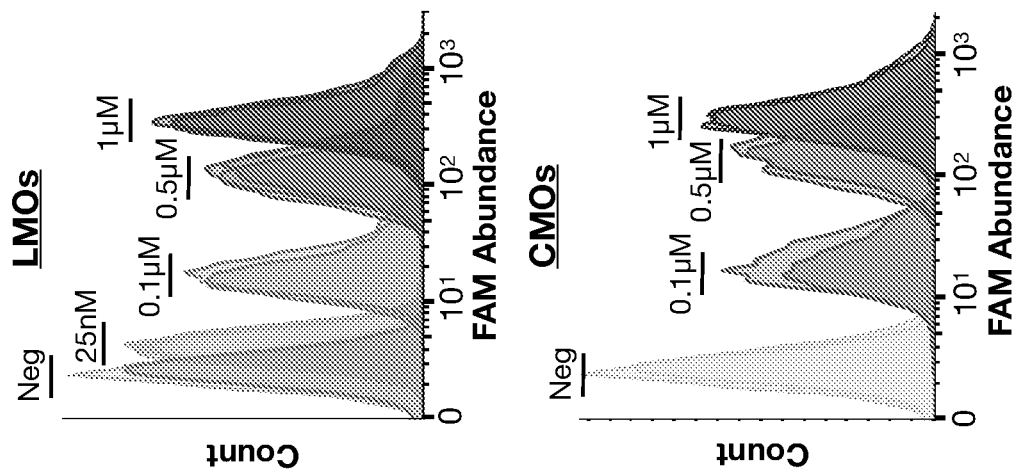
FIG. 1 shows flow cytometry analysis of human embryonic kidney cells (HEK293s), mouse embryonic fibroblasts (NIH3T3s), and human mammary epithelial cells (HMECs) labeled with LMOs and/or CMOs.
Figure 2:
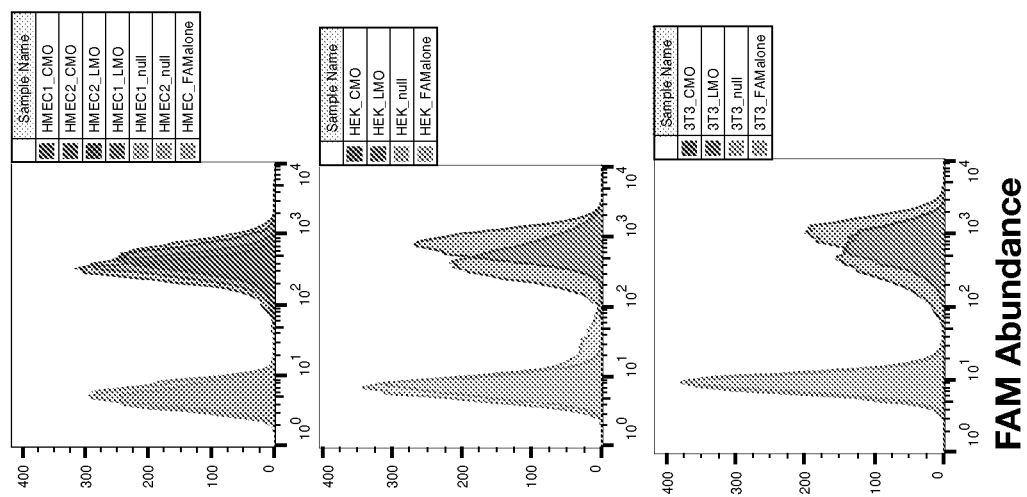
FIG. 2 shows that labeling efficiency is predictable and scales across a titration series in HEKs.
Figure 3:
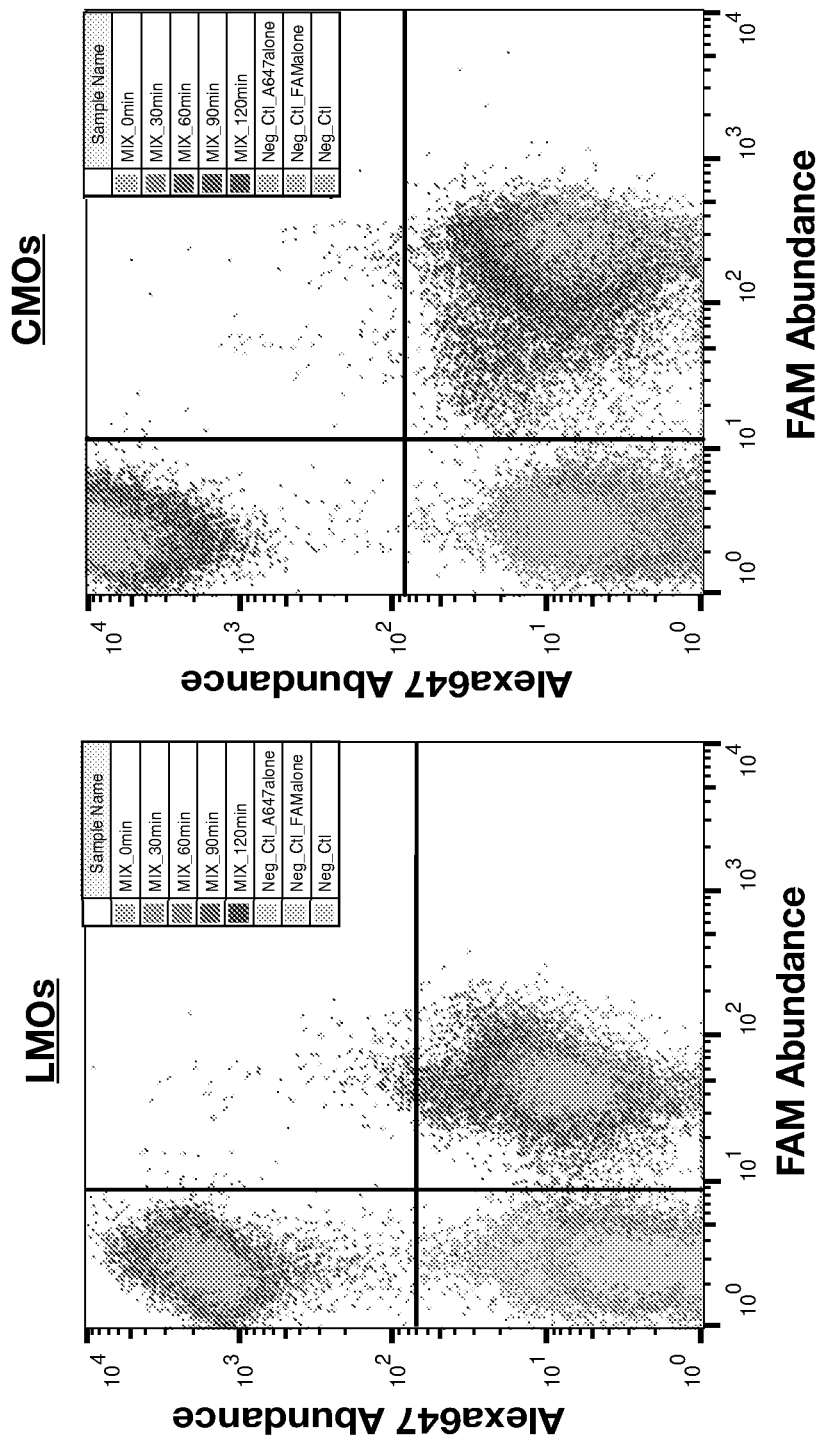
FIG. 3 shows that, with mixed cells labeled with distinct LMOs or CMOs, the extent of barcode scrambling is negligible in HEKs.
Figure 4:
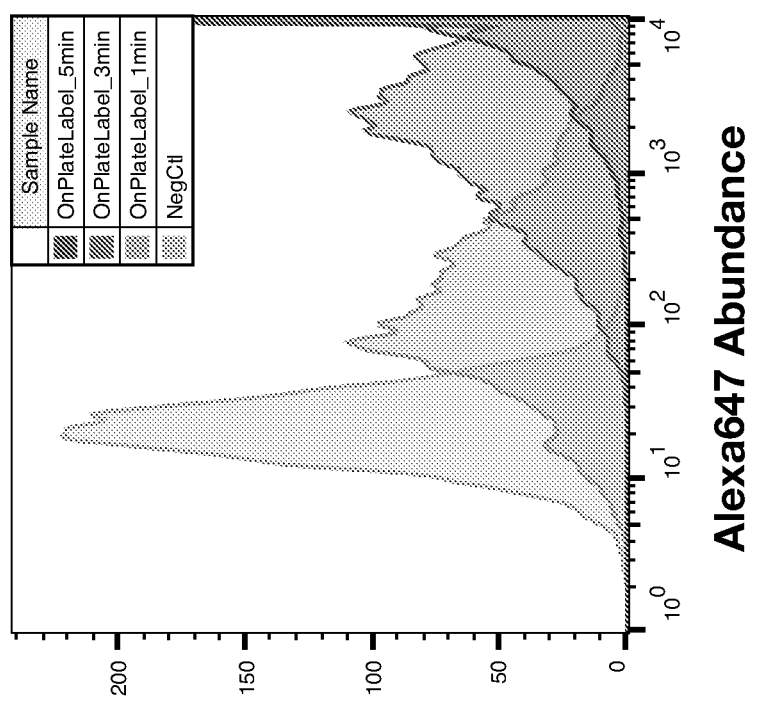
FIG. 4 shows that cells were labeled while adhered to the tissue culture dish and that the signal was not lost after trypsinization.

Flow cytometry was then used to ascertain (1) Whether different cell types could be successfully and predictably labeled using LMOs and CMOs and (2) Whether the labels were stable (i.e., did not scramble between cells) in scRNAseq buffer over a time frame that matches the 10× Genomics scRNAseq workflow. In FIG. 1, we show that human embryonic kidney cells (HEK293s), mouse embryonic fibroblasts (NIH3T3s), and human mammary epithelial cells (HMECs) can be labeled with LMOs and/or CMOs. This is an improvement over the existing BD technology, which can only be used to label cells from a single species. In FIG. 2, labeling efficiency is predictable and scales across a titration series in HEKs. In FIG. 3, mixed cells were labeled with distinct LMOs or CMOs (i.e., common anchor sequence hybridized to distinct fluorophore-conjugated oligos) and showed that the extent of barcode scrambling is negligible in HEKs. In FIG. 4, cells were labeled while adhered to the tissue culture dish and that the signal was not lost after trypsinization. This is also an improvement over existing antibody-based labeling techniques, which would be degraded upon trypsin exposure.

Example 2

HEKs and HMECs were cultured that were either treated with vehicle or 5 ng/§ L TGF-β for 24 hrs to elicit a transcriptional response. After trypsinizing the cells, these cell types were labeled with distinct LMO, CMO, or BD antibody-based barcodes and pooled cells labeled with the same TYPE of barcode immediately before microfluidic encapsulation. Four lanes of a 10× microfluidic chip were used, and each lane contained a mixture of cells labeled with LMO, CMO, BD, or no barcodes at all.

Figure 6:
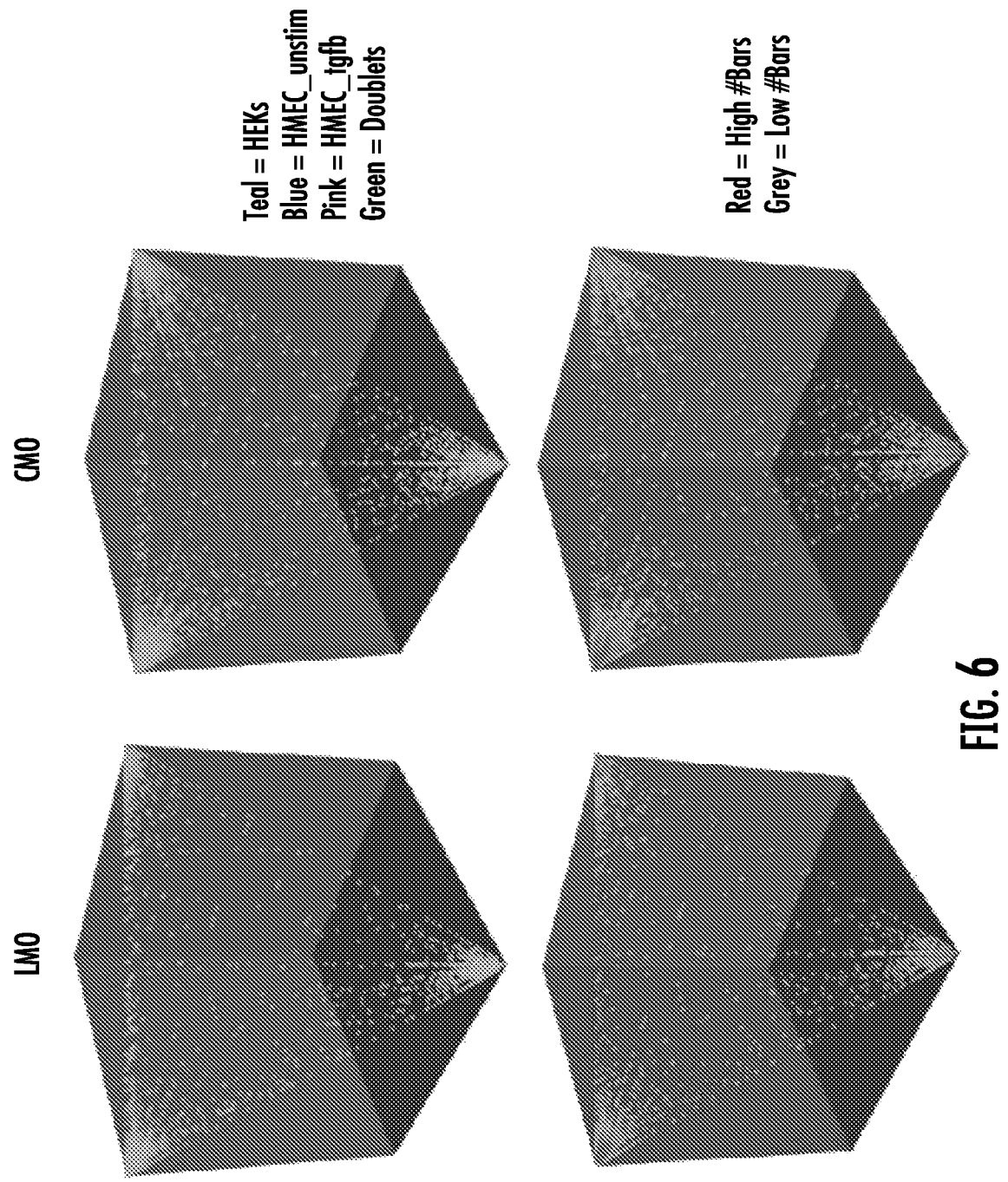
FIG. 6 shows the distribution of the proportions of sample barcodes for every single cell detected in the HiSeq data.
Figure 7:
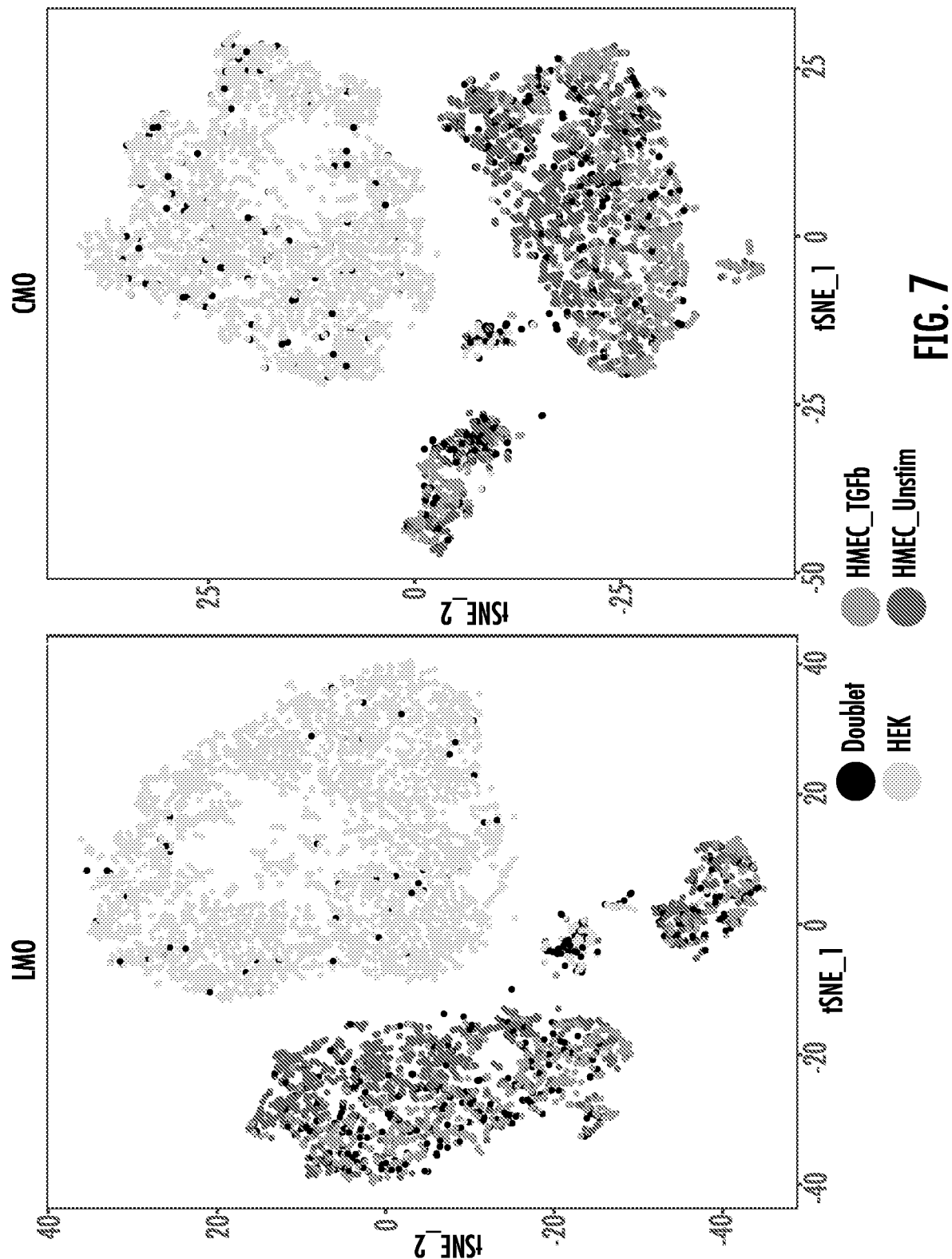
FIG. 7 visualizes the relationships between cells in the expression library data and color each cell by its associated sample call in the MiSeq data.

After validating that sequencing library preparation was successful for the LMO and CMO barcodes, the barcode libraries were sequenced using a V2 MiSeq kit and the expression libraries using the HiSeq 4000. FIG. 6 shows the distribution of the proportions of sample barcodes for every single cell detected in the HiSeq data. As would be expected for stable labeling of cells without significant barcode exchange, cells are enriched in the corners of the 3D plot (i.e., most cells are highly enriched with only a single sample barcode) for both LMO- and CMO-labeled samples.

tSNE was then used to visualize the relationships between cells in the expression library data and color each cell by its associated sample call in the MiSeq data (FIG. 7). Again, as would be expected for successful labeling, sample barcodes are not scrambled randomly throughout the clusters but, rather, are specifically enriched in distinct clusters or regions of clusters. While the stimulation of HMECs with TGFb did not elicit a sufficiently large transcriptional response to cause them to cluster completely separately from the unstimulated HMECs, sample barcodes are not scrambled within the HMEC clusters but, rather, define distinct domains within those clusters.

Example 3

Single-cell and single-nucleus RNA sequencing (scRNA-seq, snRNA-seq) have emerged as powerful technologies for interrogating the heterogeneous transcriptional profiles of multicellular systems. Early scRNA-seq workflows were limited to analyzing tens to hundreds of single-cell transcriptomes at a time. With the advent of single-cell sequencing technologies based on microwell, split-pool barcoding, and droplet-microfluidics the parallel transcriptional analysis of $10^3$-$10^5$ cells or nuclei is now routine. This increase in cell-throughput has catalyzed efforts to characterize the composition of whole organs and entire organisms.

These technologies will increasingly be used to reveal the mechanisms by which cell populations interact to promote development, homeostasis, and disease. This shift from descriptive to mechanistic analyses requires integrating spatiotemporal information, diverse perturbations, and experimental replicates in order to draw strong conclusions. While existing methods can assay many thousands of cells, sample-specific barcodes (e.g., Illumina library indices) are incorporated at the very end of standard library preparation workflows, which limits scRNA-seq sample-throughput due to reagent costs and the physical constraints of droplet microfluidics devices. Sample multiplexing approaches address this limitation by labeling cells with sample-specific barcodes prior to pooling and single-cell isolation. Several multiplexing methods have been described that distinguish samples using pre-existing genetic diversity, or introduce sample barcodes using either genetic or non-genetic mechanisms. However, each of these methods has liabilities, including issues with scalability, universality, and the potential to introduce secondary perturbations to experiments.

We identified lipid- and cholesterol-modified oligonucleotides (LMOs, CMOs) as reagents that circumvent many of the limitations of other sample multiplexing techniques. We previously described LMO and CMO scaffolds that rapidly and stably incorporate into the plasma membrane of live cells by step-wise assembly. Here, we adapt LMOs and CMOs into MULTI-seq-scRNA-seq and snRNA-seq sample multiplexing using lipid-tagged indices. MULTI-seq localizes sample barcodes to live cells and nuclei regardless of species or genetic background. MULTI-seq is non-perturbative, rapid, and involves minimal sample processing. Here, MULTI-seq simplicity and modularity enabled the analysis of a T-cell activation time-course, 96 human mammary epithelial cell (HMEC) culture conditions, and cryopreserved primary cells isolated from patient-derived xenograft (PDX) mouse models at varying stages of metastatic progression.

Design and synthesis of LMOs, CMOs, and sample barcode oligonucleotides: Anchor and co-anchor LMO and CMO designs were adapted from Weber et al. Briefly, the anchor LMO has a 5' lignoceric acid (LA) modification with two oligonucleotide domains. The 5' end is complimentary to the co-anchor LMO, which bears a 3' palmitic acid (PA), and the 3' end is complimentary to the PCR handle of the sample barcode oligonucleotide. The sample barcode was designed to have three components (as in Stoeckius et al): (1) a 5' PCR handle for barcode amplification and library preparation, (2) an 8 bp barcode with Hamming distance >3 relative to all other utilized barcodes, and (3) a 30 bp poly-A tail necessary for hybridization to the oligo-dT region of mRNA capture bead oligonucleotides. Identically designed anchor and co-anchor CMOs are conjugated to cholesterol at the 3' or 5' ends via a triethylene glycol (TEG) linker and are commercially available from Integrated DNA Technologies.

```
Anchor:
{LA/Chol-TEG}-5'-GTAACGATCCAGCTGTCACTTGGAATTCTCGGG
TGCCAAGG-3'

Co-anchor:
5'-AGTGACAGCTGGATCGTTAC-3'-{PA/TEG-Chol}

Sample barcode:
5'-CCTTGGCACCCGAGAATTCCANNNNNNNNA₃₀-3'
```

Anchor LMO and co-anchor LMO synthesis: Oligonucleotides were synthesized on an Applied Biosystems Expedite 8909 DNA synthesizer, as previously described (Weber et al, Supplemental Materials).

Cell culture: For the proof-of-concept scRNA-seq and snRNA-seq experiments, HEK293 cells, HMECs, Jurkat cells, and MEF cells were maintained at 37° C. with 5% $CO_2$. HEK293 and MEF cells were cultured in Dulbecco's Modified Eagle's Medium, High Glucose (DMEM H-21) containing 4.5 g/L glucose, 0.584 g/L L-glutamine, 3.7 g/L $NaHCO_3$, supplemented with 10% fetal bovine serum (FBS) and penicillin/streptomycin (100 U/mL and 100 µg/mL, respectively). HMECs were cultured in M87A media with or without 24 hours of stimulation with 5 ng/mL human recombinant TGF-β (Peprotech). Jurkat cells were cultured in RPMI-1640 with 25 mM HEPES and 2.0 g/L $NaHCO_3$ supplemented with 10% FBS and penicillin/streptomycin (100 U/mL and 100 µg/mL, respectively).

For the 96-sample HMEC experiments, fourth passage HMECs were lifted using 0.05% trypsin-EDTA for 5 minutes. The cell suspension was passed through a 45 µm cell strainer to remove any clumps. The cells were washed with M87A media once and resuspended at $10^7$ cells/mL. The cells were incubated with 1:50 APC/Cy-7 anti-human/mouse CD49f (Biolegend, #313628) and 1:200 FITC anti-human CD326 (EpCAM) (Biolegend, #324204) antibodies for 30 minutes on ice. The cells were washed once with PBS and resuspended in PBS with 2% BSA with DAPI at 2-4 million cells/mL. Cells were sorted on BD FACSAria III. DAPI+ cells were discarded. LEPs were gated as $EpCAM^{hi}$/$CD49f^{lo}$ and MEPs were gated as $EpCAM^{lo}$/$CD491^{hi}$ (FIG. 17). Notably, this gating strategy results in trace numbers of MEPs and LEPs sorted incorrectly. HMEC sub-populations were sorted into 24-well plates such that wells contained LEPs only, MEPs only, or a 2:1 ratio of LEPs to MEPs. Sorted cell populations were cultured for 48 hours in M87A media before culturing for 72 hours in M87A media (-EGF) supplemented with different signaling molecules or signaling molecule combinations. Specifically, M87A media (-EGF) was supplemented with 100 ng/mL RANKL, 100 ng/mL WNT4, 100 ng/mL IGF-1, 113 ng/mL AREG, and/or 5 ng/mL EGF (all from Peprotech) alone or in all possible pairwise combinations. For the 96-sample HMEC technical replicate experiment, in vitro cultures were prepared as described above, except all sorted wells contained both LEPs and MEPs. Cultures were then grown in complete M87A media for 72 hours prior to isolation.

scRNA-seq sample preparation: For the proof-of-concept experiment, cells were first treated with trypsin for 5 minutes at 37° C. in 0.05% trypsin-EDTA before quenching with appropriate cell culture media. Single-cell suspensions were then pelleted for 4 minutes at 160 rcf and washed once with PBS before suspension in 90 µL of a 200 nM solution containing equimolar amounts of anchor LMO and sample barcode oligonucleotides in PBS. Anchor LMO-barcode labeling was performed for 5 minutes on ice before 10 µL of 2 µM co-anchor LMO in PBS (for a final concentration of 200 nM) was added to each cell pool. Following gentle mixing, the labeling reaction was continued on ice for another 5 minutes before cells were washed twice with PBS, resuspended in PBS with 0.04% BSA, filtered, and pooled. The same workflow was also performed with CMOs. LMO—, CMO—, and unlabeled control cells were then loaded into three distinct 10× microfluidics lanes.

For the original 96-plex HMEC experiment, LMO labeling was performed during trypsinization in order to minimize wash steps and thereby limit cell loss and preserve cell viability. HMECs cultured in 24-well plates were labeled for 5 minutes at 37° C. and 5% $CO_2$ in 190 µL of a 200 nM solution containing equimolar amounts of anchor LMO and sample barcode oligonucleotides in 0.05% trypsin-EDTA. 10 µL of 4 µM co-anchor LMO in 0.05% trypsin-EDTA was then added to each well (for a final concentration of 200 nM) and labeling/trypsinization was continued for another 5 minutes at 37° C. and 5% $CO_2$ before quenching with appropriate cell culture media. A similar labeling protocol was used for the technical replicate experiment, except LMOs were incorporated once the cells were in single-cell suspension. Cells were then transferred to a 96-well plate for washing with 0.04% BSA in PBS. Finally, cells were pooled into a single aliquot, filtered through a 0.45 µm cell strainer, and counted before loading 10× microfluidics lanes.

For the PDX experiment, primary tumors and lungs were cryopreserved after dissection from triple-negative breast cancer PDX models generated in NOD-SCID gamma (NSG) mice as described previously. The UCSF Institutional Animal Care and Use Committee (IACUC) reviewed and approved all animal experiments. On the day of the experiment, cryopreserved tissues were thawed and dissociated in digestion media containing 50 µg/mL Liberase TL (Sigma-Aldrich) and $2×10^4$ U/mL DNase I (Sigma-Aldrich) in DMEM/F12 (Gibco) using standard GentleMacs protocols. Dissociated cells were then filtered through a 70 µm cell strainer to obtain a single-cell suspension prior to washing with PBS. Cells were then stained for 15 minutes on ice with 1:500 Zombie NIR (BioLegend, #423105) viability dye in PBS. Cells were then washed with 2% FBS in PBS prior to blocking for 5 minutes on ice with 100 µL 1:200 Fc-block (Tonbo, #70-0161-U500) in 2% FBS in PBS. After blocking, cells were stained for 45 minutes on ice with 100 µL of an antibody cocktail containing anti-mouse TER119 (FITC, ThermoFisher, #11-5921-82), anti-mouse CD31 (FITC, ThermoFisher, #11-0311-85), anti-mouse CD45 (BV450, Tonbo, #75-0451-U100), anti-mouse MHC-I (APC, eBioscience, #17-5999-82) and anti-human CD298 (PE, BioLegend, #341704). Cells were then washed with PBS prior to MULTI-seq labeling for 5 minutes on ice with 100 µL of 2.5 µM anchor LMO-barcode in PBS. 20 µL of 15 µM co-anchor LMO in PBS was added to each cell pool (for a final concentration of 2.5 μM) and labeling was continued for another 5 minutes.

Notably, we used a 10-fold greater LMO concentration for this experiment to account for increases in the total number of cells and lipophilic molecules remaining after dissociation. Following LMO labeling, cells were diluted with 100 μL of 2% FBS in PBS to 'quench' LMOs and washed once in 2% FBS in PBS. Finally, mCD45+ mouse immune cells and hCD298+ human metastases from dissociated primary tumors and lungs were pooled after FACS enrichment, as described previously (Lawson et al., 2015; FIG. 18, FIG. 19). Cell pools were then sequenced in a single 10× microfluidics lane.

snRNA-seq sample preparation: For the Jurkat cell activation time-course, $2\times10^5$ Jurkat cells were added to 8 wells of a 12-well plate and treated with 10 ng/μL phorbol 12-myristate 13-acetate (PMA, Sigma-Aldrich #P8139) and 1.3 μM ionomycin (Sigma-Aldrich #10634) at 15 min, 30 min, 1 hr, 2 hr, 4 hr, 6 hr, or 24 hr prior to barcoding with LMOs. A single well of Jurkat cells were left untreated. HEK293 and MEF cells were cultured as described above. Nuclei were isolated from cells using a protocol adapted from 10× Genomics. Briefly, suspensions of HEK293, MEF, or treated Jurkat cells were washed once with PBS, pelleted at 160 rcf (HEK293, MEFS) or 300 rcf (Jurkat) for 4 min at 4° C. and suspended in chilled lysis buffer (0.5% Nonidet P40 Substitute, 10 mM Tris-HCl, 10 mM NaCl, and 3 mM $MgCl_2$ in milliQ water) to a density of $2.5\times10^6$ cells/mL. Lysis proceeded for 5 minutes on ice, after which the lysate was pelleted (500 rcf, 4° C., 4 minutes) and washed three times in chilled resuspension buffer (2% BSA in PBS). Nuclei were then diluted to a concentration of $\sim10^6$ nuclei/mL prior to LMO or CMO labeling. HEK293 and MEF cells were each divided into two samples and labeled with LMOs or CMOs (500 nM in resuspension buffer) using the same procedure as described for live cells (presence of BSA during labeling is the lone alteration as it is required to prevent nuclei clumping). Each Jurkat sample was labeled with LMOs, alone. Each sample was washed 3× in 1 mL resuspension buffer (500 rcf, 4° C., 4 min). The four LMO- and CMO-labeled HEK293 and MEF samples were pooled in equal portions and, separately, Jurkat samples were pooled in equal proportions. These final two samples were combined in a 1:1 ratio and sequenced on a single 10× microfluidics lane.

scRNA-seq and snRNA-seq library preparation: Sequencing libraries were prepared using a custom protocol based on the 10× Genomics Single Cell V2 and CITE-seq workflows. Briefly, the 10× workflow was followed up until cDNA amplification, where 1 uL of 2.5 uM MULTI-Seq additive primer was added to the cDNA amplification master mix:

```
MULTI-seq additive primer:
5'-CCTTGGCACCCGAGAATTCC-3'
```

This primer increases barcode sequencing yield by enabling the amplification of barcodes that successfully primed reverse transcription on mRNA capture beads but were not extended via template switching (FIG. 110C). Notably, the MULTI-seq additive primer was erroneously excluded during the proof-of-concept snRNA-seq library preparation, and nuclei were still able to be robustly classified. Following amplification, barcode and endogenous cDNA fractions were separated using a 0.6×SPRI size selection. The endogenous cDNA fraction was then processed according to the 10× workflow until next-generation sequencing (NGS) with the following formats:

| Dataset | NGS Format |
|---|---|
| Proof-of-concept (scRNA-seq) | 2× HiSeq 4000 |
| Proof-of-concept (snRNA-seq) | NovaSeq (20%) |
| HMEC | NovaSeq (100%) |
| HMEC (technical replicate) | NovaSeq (5%) |
| PDX | NovaSeq (70%) |

To prepare the barcode fraction for NGS, contaminating oligonucleotides remaining from cDNA amplification were first removed using an established small RNA enrichment protocol (Beckman Coulter). Specifically, we increased the final SPRI ratio in the barcode fraction to 3.2× reaction volumes and added 1.8× reaction volumes of 100% isopropanol (Sigma-Aldrich). Beads were then washed twice with 400 μL of 80% ethanol and allowed to air dry for 2-3 minutes before elution with 50 μL of Buffer EB (Qiagen, USA). Eluted barcode cDNA was then quantified using QuBit before library preparation PCR (95° C., 5'; 98° C., 15"; 60° C., 30"; 72° C., 30"; 8 cycles; 72° C., 1'; 4° C. hold). Each reaction volume was a total of 50 μL containing 26.25 μL 2×KAPA HiFi HotStart master mix (Roche), 2.5 μL of 10 μM TruSeq RPIX primer (Illumina), 2.5 μL of 10 μM TruSeq Universal Adaptor primer (Illumina), 3.5 ng barcode cDNA, and nuclease-free water. container—chunk of cell (lipid)—barcode—each well From about 100 to about-1000 microns of thickness of tissue or cell slices taken from a sample from a subject
1. Spatially barcode
2. Correlate position of slice with barcode
3. Vibrotone—biopsy tissue slices
4. Dropseq
5. Mark or recruit to process—cells out of wells and sequence single cell

```
TruSeq RPIX5'-
CAAGCAGAAGACGGCATACGAGATNNNNNNNGTGACTGGAGTTCCTTGGCA
CCCGAGAATTCCA-3'
``` where N is any nucleotide.

```
TruSeq P5 Adaptor:
5'-AATGATACGGCGACCACCGAGATCTACACTCTTTCCCTACACGACGC
TCTTCCGATCT-3'
```

Following library preparation PCR, remaining sequencing primers and contaminating oligonucleotides were removed via a 1.6×SPRI clean-up. Representative Bioanalyzer traces at different stages of the MULTI-seq library preparation workflow are documented in FIG. 11. Barcode libraries were sequenced using the NGS formats documented in FIG. 21. Notably, sequencing reads predominantly aligned to the barcode reference sequences, and resulted in high SNRs with low rates of duplicated UMIs, suggesting that barcode libraries were not sequenced to saturation for any of the presented experiments.

Expression library pre-processing: Expression library FASTQs were pre-processed using CellRanger (10× Genomics) and aligned to the hg19 (proof-of-concept scRNA-seq, HMEC), concatenated mm10-hg19 (PDX), or concatenated mm10-hg19 pre-mRNA (proof-of-concept snRNA-seq) reference transcriptomes. When multiple 10× lanes were sequenced in an experiment, CellRanger aggregate was used to perform read-depth normalization.

Cell/Nuclei calling: For the proof-of-concept scRNA-seq, snRNA-seq and HMEC technical replicate experiments, cell-associated barcodes were defined using CellRanger. For the original 96-plex HMEC experiment, cells were defined as cell barcodes (1) associated with >=600 total RNA UMIs that (2) were successfully classified during MULTI-seq sample classification workflow. We manually selected 600 RNA UMIs as a threshold in order to exclude low-quality cell barcodes. For the PDX experiment, we defined cells as barcodes (1) associated with >=100 total RNA UMIs that (2) were successfully classified during the MULTI-seq sample classification workflow (Supplemental Materials).

Expression library analysis: Following pre-processing and cell/nuclei calling, RNA UMI count matrices were prepared for analysis using the 'Seurat' R package, as described previously. Briefly, genes expressed in fewer than 3 cells were discarded before the percentage of reads mapping to mitochondrial genes (% Mito) was computed for each cell. Outlier cells with elevated % Mito were visually defined and discarded. Data was then log 2-transformed, centered, and scaled before variance due to % Mito and the total number of RNA UMIs were regressed out. Highly variable genes were then defined for each dataset by selecting mean expression and dispersion thresholds resulting in ~2000 total genes. These variable genes were then used during PCA, and statistically-significant PCs were defined by PC elbow plot inflection point estimation. Significant PCs were then utilized for unsupervised Louvian clustering and dimensionality reduction with t-SNE.

Following pre-processing, differential gene expression analysis was performed using the 'FindMarkers' command in 'Seurat', with 'test.use set to 'bimod' and log fold-change thresholds set in a context-dependent fashion (Supplemental Materials). Other dataset-specific analyses are discussed in the Supplemental Materials. Dataset-specific 'Seurat' pre-processing parameters:

| Dataset | PCs | Variable gene dispersion threshold | Variable gene expression threshold |
|---|---|---|---|
| Proof-of-concept, live cells | 8 | 0.5 | 0.025 |
| Proof-of-concept, human nuclei | 8 | 0.5 | 0.0125 |
| Proof-of-concept, mouse nuclei | 6 | 0.5 | 0.0125 |
| Proof-of-concept, Jurkat nuclei | 10 | 0.5 | 0.0125 |
| 96-Plex HMEC, all cells | 8 | 0.65 | 0.05 |
| 96-Plex HMEC, all LEPs | 9 | 0.4 | 0.05 |
| 96-Plex HMEC, all MEPs | 10 | 0.75 | 0.05 |
| 96-Plex HMEC, resting LEPs | 8 | 0.4 | 0.05 |
| 96-Plex HMEC, resting MEPs | 6 | 1.0 | 0.05 |
| PDX, mouse immune cells | 15 | 0.75 | 0.05 |
| PDX, mouse lung immune cells | 14 | 0.7 | 0.05 |
| PDX, classical monocytes | 10 | 0.53 | 0.05 |
| PDX, late-stage classical monocytes | 6 | 0.65 | 0.05 |

Barcode library pre-processing: Raw barcode library FASTQs were converted to barcode UMI count matrices using custom scripts leveraging the 'ShortRead' and 'stringdist' R packages (FIG. 13). Briefly, raw FASTQs were first parsed to discard reads where the first 16 bases of R1 did not perfectly match any of the cell barcodes associated a pre-defined list of cell barcodes. Second, reads where the first 8 bases of R2 did not align with <1 mismatch to any reference barcode were discarded. Third, reads were binned by cell barcodes and duplicated UMIs were identified as reads where bases 17-26 of R2 exactly matched. Finally, reference barcode alignment results were then parsed to remove duplicated UMIs before being converted into a final barcode UMI count matrix.

Barcode library sequencing statistics: MULTI-seq barcode library sequencing statistics were computed for classified singlets in all datasets presented in this study. SNR was computed for every cell by finding the quotient of the top two most abundant barcodes. Mean SNRs among all singlets for each dataset presented in this study are documented in FIG. 21. The alignment rate was defined as the proportion of singlet-associated sequencing reads where the first 8 bases of R2 aligned with <1 mismatch to any reference barcode.

MULTI-seq sample classification: MULTI-seq barcode UMI count matrices were used to classify cells into sample groups via a workflow inspired by previous scRNA-seq multiplexing approaches (FIG. 13). First, raw barcode reads were $\log_2$-transformed and mean-centered. The presence of each barcode was then visually inspected by performing t-SNE on the normalized barcode count matrix, as implemented in the 'Rtsne' R package with 'initial_dims' set to the total number of barcodes. Missing barcodes (observed only for the 96-plex HMEC experiment) were discerned as those lacking any enrichment in barcode space and were removed.

Next, the top and bottom 0.1% of values for each barcode were excluded and the probability density function (PDF) for each barcode was defined by applying the 'approxfun' R function to Gaussian kernel density estimations produced using the 'bkde' function from the 'KernSmooth' R package. We then sought to classify cells according to the assumption that groups of cells that are positive and negative for each barcode should manifest as local PDF maxima. To this end, we computed all local maxima for each PDF and defined negative and positive maxima as the most frequent and highest local maxima, respectively. Notably, this strategy assumes that truly-barcoded cells will have the highest abundance for any given barcode, and that no individual sample group will have more members than the sum of all other groups.

With these positive and negative approximations in hand, we next sought to define barcode-specific UMI thresholds. To find the best inter-maxima quantile for threshold definition (e.g., an inter-maxima quantile of 0.5 corresponds to the mid-point), we iterated across 0.02-quantile increments and chose the value that maximized the number of singlet classifications. Sample classifications were then made using these barcode-specific UMI thresholds by discerning which thresholds each cell surpasses, with doublets being defined as cells surpassing >1 threshold. Negative cells (i.e., cells surpassing 0 thresholds) were then removed, and this procedure was repeated until all cells were classified as singlets or doublets. Subsets of negative cells could then be reclassified using semi-supervised learning, where singlets defined during the initial workflow are used to initialize cluster centers during k-means clustering of negative cells (Supplemental Materials).

Statistical Tests: Statistically-significant TGFBI expression enrichment amongst TGF-β-stimulated and unstimulated HMECs in the proof-of-concept scRNA-seq experiment was assessed using the Wilcoxon rank-sum test (two-sided, n=1,950 cells). Statistically-significant TGFBI expression enrichment amongst LEPs and MEPs grouped according to signaling molecule exposure was assessed using the Wilcoxon rank-sum test (two-sided, n=32 signaling molecule condition groups). Differentially expressed genes between clusters in all datasets were defined using the likelihood-ratio test for single cell gene expression with Bonferroni multiple comparisons adjustment. Statistically-significant changes in lung immune cell type proportions during metastatic progression were assessed using the two-proportion z-test with Bonferroni multiple comparisons adjustment (n=44 tumor-stage/cell type groups).

Raw gene expression and barcode count matrices were uploaded to the Gene Expression Omnibus (GSE . . . ) along with pertinent metadata.

Figure 8A:
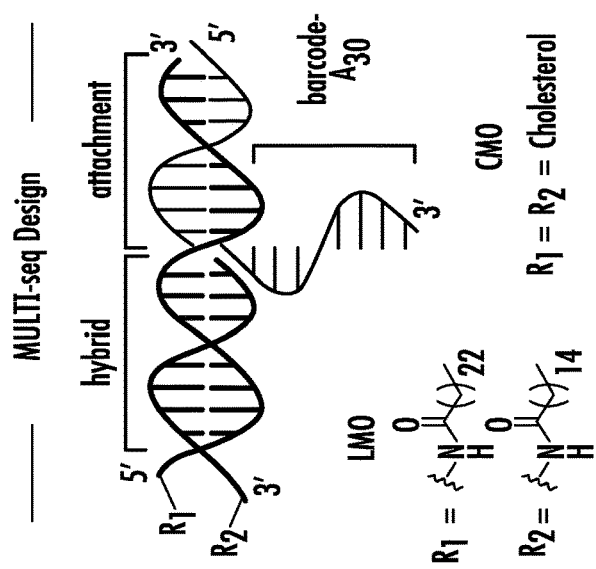
FIG. 8A shows a diagram of the anchor/co-anchor LMO and CMO scaffolds (black) with hybridized sample barcode oligonucleotide (red). LMOs and CMOs are distinguished by their unique lipophilic moieties (e.g., lignoceric acid, palmitic acid, or cholesterol).

MULTI-seq overview: MULTI-seq localizes DNA barcodes to plasma membranes by hybridization to an 'anchor' LMO. The 'anchor' LMO associates with membranes through a hydrophobic 5' lignoceric acid amide. Subsequent hybridization to a 'co-anchor' LMO incorporating a 3' palmitic acid amide increases the hydrophobicity of the complex and thereby prolongs membrane retention (FIG. 8A). MULTI-seq sample barcodes include a 3' poly-A capture sequence, an 8 bp sample barcode, and a 5' PCR handle necessary for library preparation and anchor hybridization. Cells or nuclei carry membrane-associated MULTI-seq barcodes into emulsion droplets where the 3' poly-A domain mimics endogenous transcripts during hybridization to mRNA capture beads. Endogenous transcripts and MULTI-seq barcodes are then linked to a common cell- or nucleus-specific barcode during reverse transcription, which enables sample demultiplexing. MULTI-seq barcode and endogenous expression libraries are separated by size selection prior to next-generation sequencing library construction, enabling pooled sequencing at user-defined proportions (Experimental Methods). The same strategy can be applied to commercially-available CMOs.

Figures 11A, 11B:
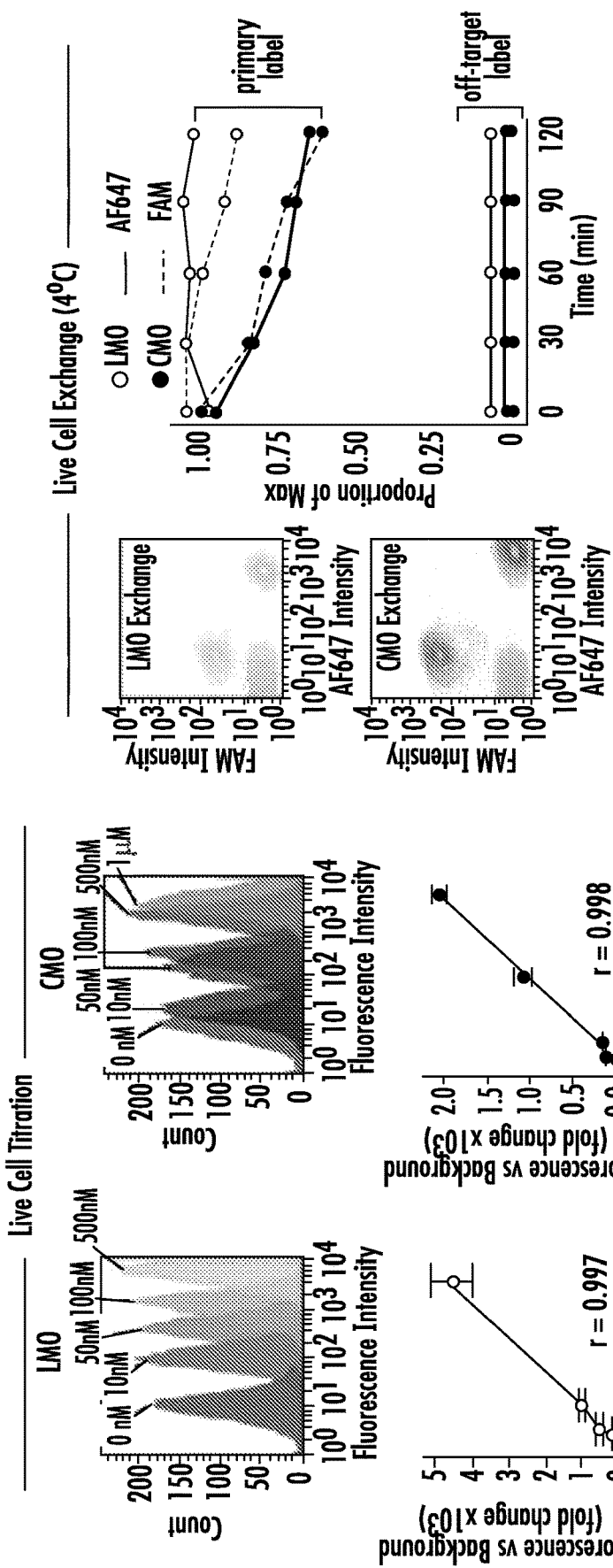
FIG. 11A shows live-cell LMO (gold) and CMO (purple) labeling efficiency varies predictably across a titration curve of anchor and co-anchor LMO/CMO concentrations. Qualitative trends shown with histograms (top) are supported by regression analyses (bottom) demonstrating technical reproducibility and linear relationship between LMO/CMO concentration and fluorescence abundance. n=10,000 events/sample. Data represented as mean±SEM over 3 experimental replicates.
FIG. 11B shows a time-course analysis of LMO and CMO scaffold loss and exchange on ice following mixing of live cell populations labeled with either AF647- or FAM-conjugated barcode probes. Qualitative trends (contour plots, left) document how LMO or CMO labeled cells maintain fluorescence signal over unlabeled control cells (grey) over time. Quantitative analysis (right) illustrates how LMO scaffolds more stably embed in the plasma membrane relative to CMO scaffolds, although sample-to-sample cross-talk is minimal. n=10,000 events/time-point. Experiment was repeated 3 times with similar results.
Figures 11C, 11D:
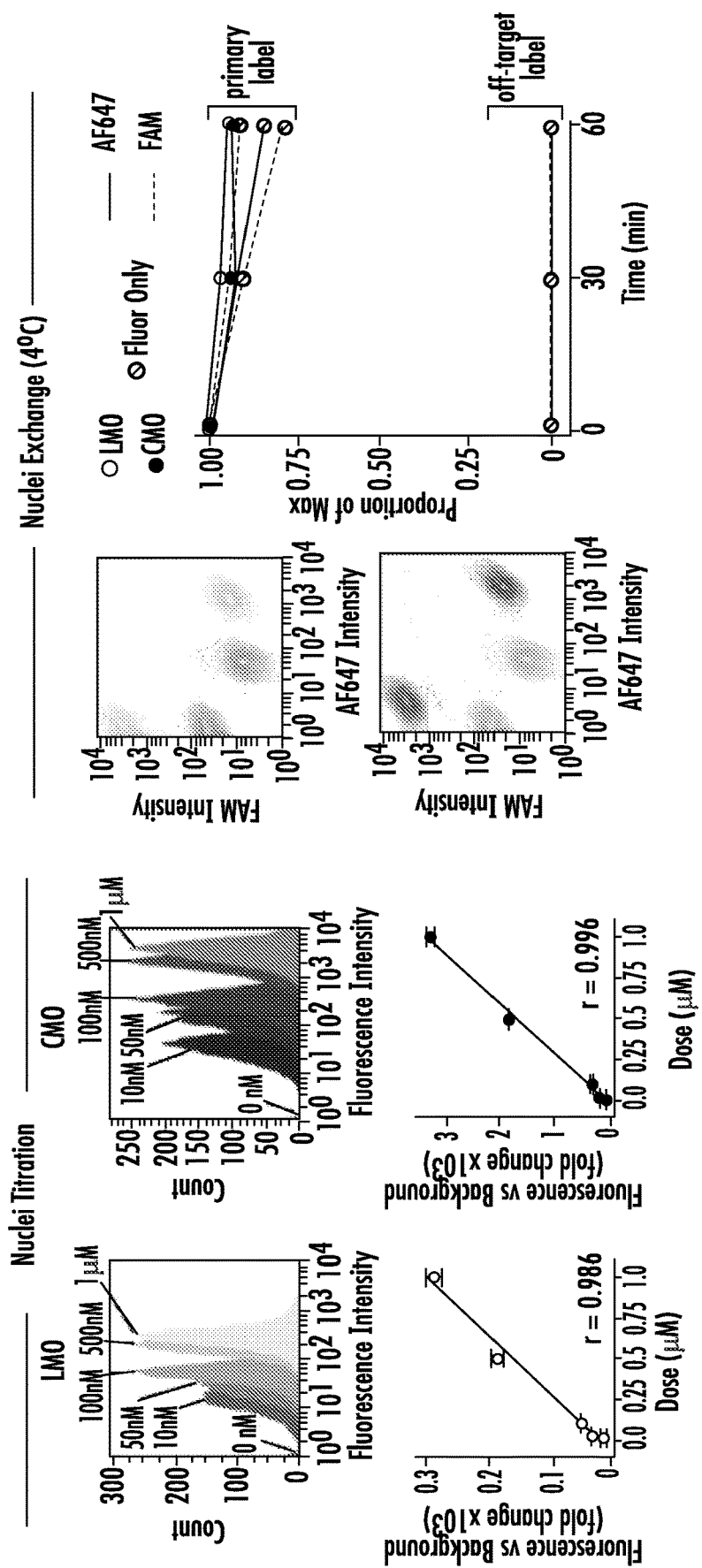
FIG. 11C shows the same experiment as described in FIG. 11A, except with nuclei. n=10,000 events/sample. Data represented as mean±SEM over 3 experimental replicates.
FIG. 11D shows the same experiment as described in FIG. 11B, except with nuclei. Difference between LMO and CMO membrane residency kinetics does not occur during nuclear membrane labeling. n=10,000 events/time-point.
Figures 11E, 11F:
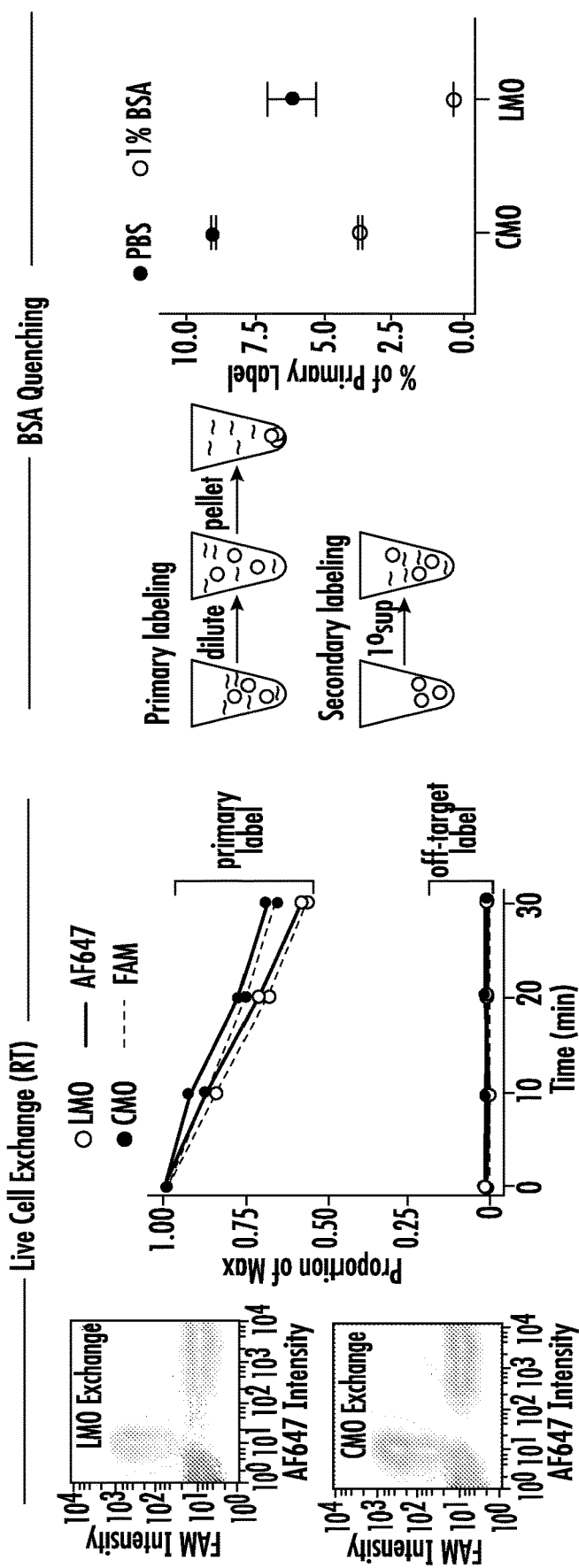
FIG. 11E shows the same experiment as described in FIG. 11C, except at room temperature. The LMO advantage in label stability shown at 4° C. is lost at RT as both CMO (purple) and LMO (gold) labels decrease at similar rates. n=10,000 events/time-point.
FIG. 11F shows live-cells were labeled with LMO or CMO at 200 nM and diluted with either PBS (black) or 1% BSA in PBS (red). The cells were pelleted and the supernatant was transferred to unlabeled cells to determine the labeling efficiency of remaining LMO or CMO label. Dilution with BSA leads to a decrease in supernatant labeling relative to dilution with PBS alone. n=10,000 events/sample. Data represented as mean±SEM over 3 experimental replicates.

We used flow cytometry to evaluate whether LMOs and CMOs predictably label and minimally exchange between live cells at typical sample preparation temperatures of 4° C. (FIG. 11A, S 1B). Identical experiments were also performed using freshly-isolated nuclei (FIG. 11C, SID). These data revealed that LMOs exhibit longer membrane residency times than CMOs on live-cell membranes at 4° C., whereas LMOs and CMOs exchange comparably between live cells at room temperature, suggesting cells should be maintained on ice to achieve optimal sample multiplexing results (FIG. 11E). For nuclei, both oligonucleotide conjugates showed minimal exchange between nuclear membranes (FIG. 11D), however, bovine serum albumin (BSA) in nuclei isolation buffer specifically quenched LMOs, reducing labeling efficiency (FIG. 11B). While problematic during nuclei labeling, we reasoned that LMO quenching could be strategically employed during live cell labeling to reduce off-target barcoding and potentially minimize washes prior to sample pooling. Indeed, we found that diluting LMO-labeling reactions with 1% BSA in PBS resulted in minimal off-target labeling following pooling (<1% of primary labeling signal), which was 18-fold lower than dilution with PBS (FIG. 11F).

Figure 8B:
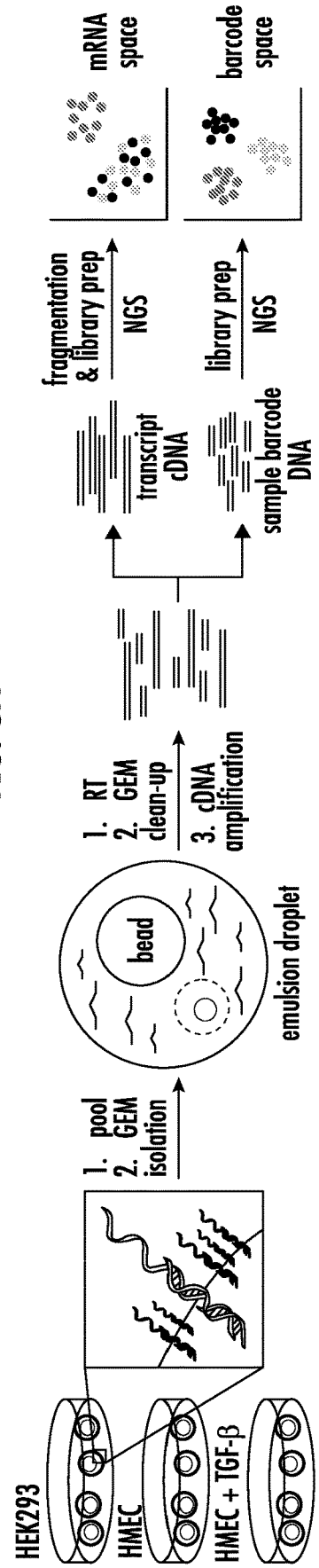
FIG. 8B shows a Schematic overview of a proof-of-concept single-cell RNA sequencing experiment using MULTI-seq. Three samples (HEKs and HMECs with and without TGF-β stimulation) were barcoded with either LMOs or CMOs and sequenced alongside unlabeled controls. Cells were pooled together prior to scRNA-seq. Next-generation sequencing produces two UMI count matrices corresponding to gene expression and barcode abundances.

MULTI-seq enables scRNA-seq sample demultiplexing: We tested the capacity of MULTI-seq to demultiplex scRNA-seq samples by performing a proof-of-concept experiment using HEK293 cells (HEKs) and primary human mammary epithelial cells (HMECs) cultured in the presence or absence of TGF-β (FIG. 8B). Cells were trypsinized, barcoded with LMOs or CMOs, and pooled prior to droplet microfluidic-emulsion with the 10× Genomics Chromium system. In parallel, we prepared un-barcoded replicates to test whether MULTI-seq influenced gene expression or mRNA capture efficiency.

Figure 12A:
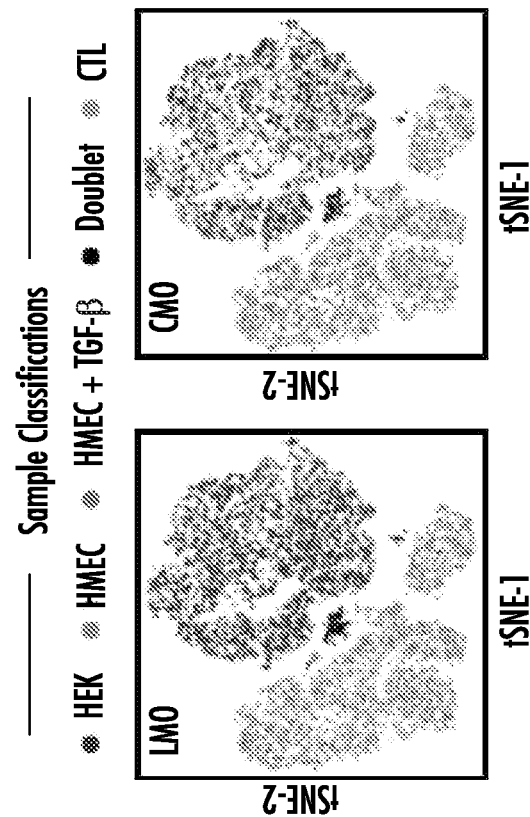
FIG. 12A shows cell state annotations for aggregated LMO, CMO, and unlabeled control scRNA-seq data. Violin plots illustrate marker genes used to define HEKs (pink), MEPs (cyan), and LEPs (dark teal). n=15,482 cells.
Figure 12B:
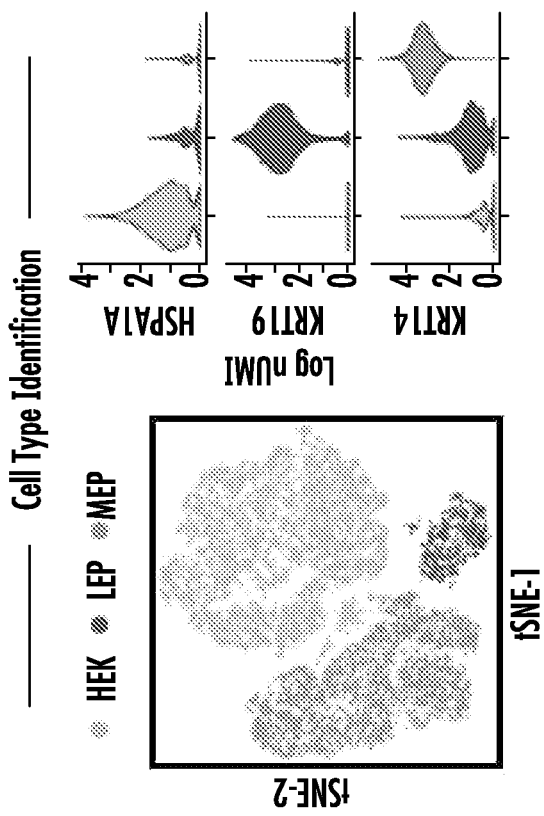
FIG. 12B shows MULTI-seq classifications for LMO- (left) and CMO-labeled cells (right) mapped onto aggregated gene expression space. As with LMO labeling, sample classifications for CMO-labeled samples match their expected cell type annotations. n=15,482 cells.

Following data pre-processing (Computational Methods), we analyzed a final scRNA-seq dataset containing 14,377 total cells. We identified clusters in gene expression space according to known markers for HEKs as well as the two cellular components of HMECs, myoepithelial (MEPs) and luminal epithelial cells (LEPs, FIG. 8C, FIG. 12A). Projecting MULTI-seq barcode classifications onto gene expression space for LMO-labeled (FIG. 8D) and CMO-labeled cells (FIG. 12B) illustrates that both membrane scaffolds successfully demultiplexed each sample. HMECs predicted to have been cultured with TGF-β exhibited enriched TGFBI expression (FIG. 8E). Importantly, RNA and MULTI-seq barcode UMI counts were not negatively correlated, demonstrating that MULTI-seq does not impair mRNA capture (FIG. 12C). However, we observed transcriptional changes in CMO-labeled HEKs (FIG. 12D, FIG. 20) that were absent in LMO-labeled HEKs.

Figure 12G:
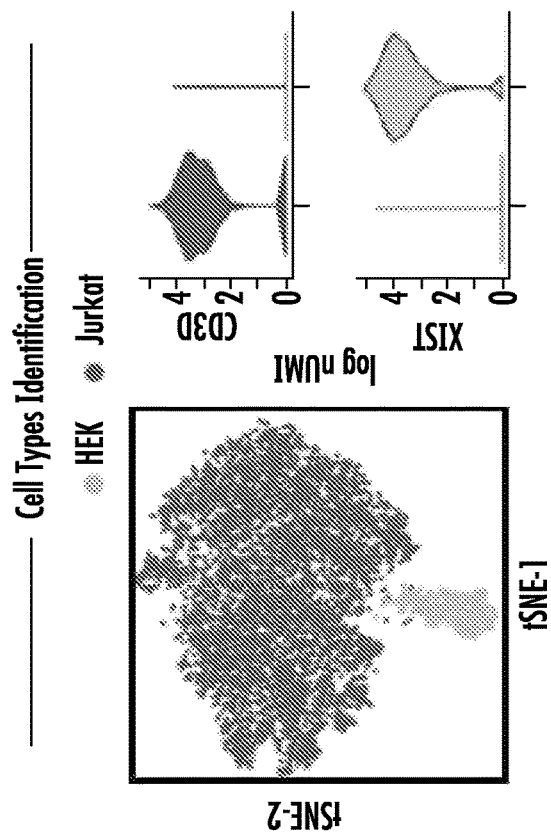
FIG. 12G shows cell state annotations for aggregated LMO, CMO, and unlabeled control snRNA-seq data. Violin plots illustrate marker genes used to define HEKs (pink) and Jurkats (dark teal). n=8,468 human nuclei.
Figure 12F:
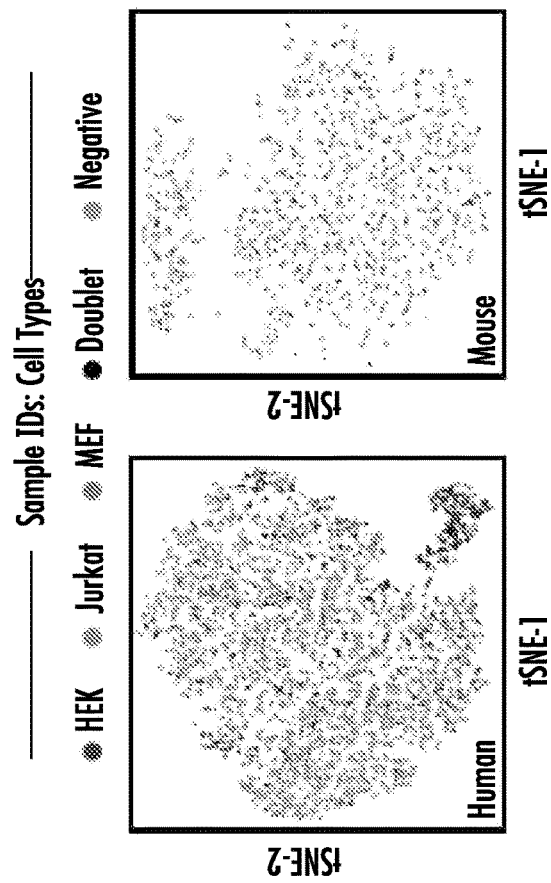
FIG. 12F shows MULTI-seq classifications exhibit species-specificity between Jurkat cells (green), HEKs (dark red) and MEFs (blue). n=4,848 (human) and 1,046 (mouse) MULTI-seq labeled nuclei.
Figure 12H:
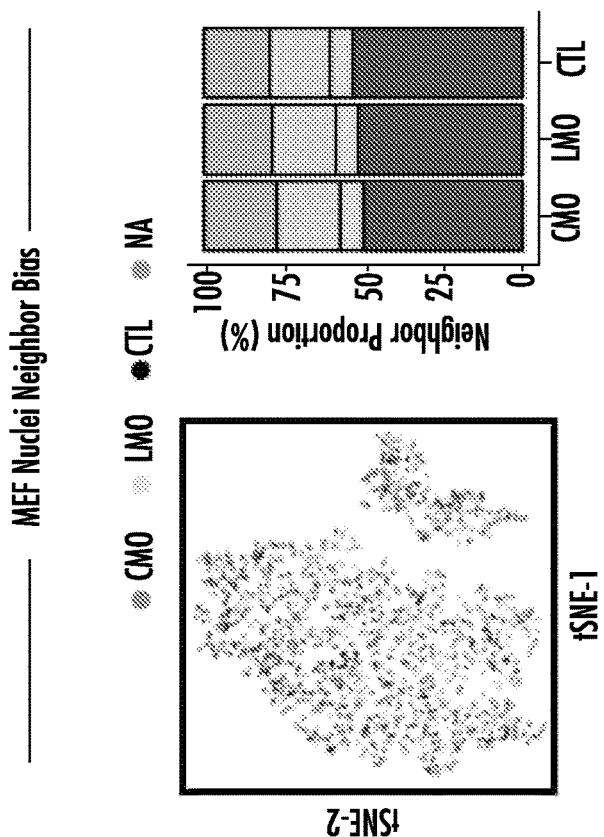
FIG. 12H shows the same analysis as described in FIG. 12C on snRNA-seq data. n=2,113 MEF nuclei. r=Pearson's correlation.
Figure 12I:
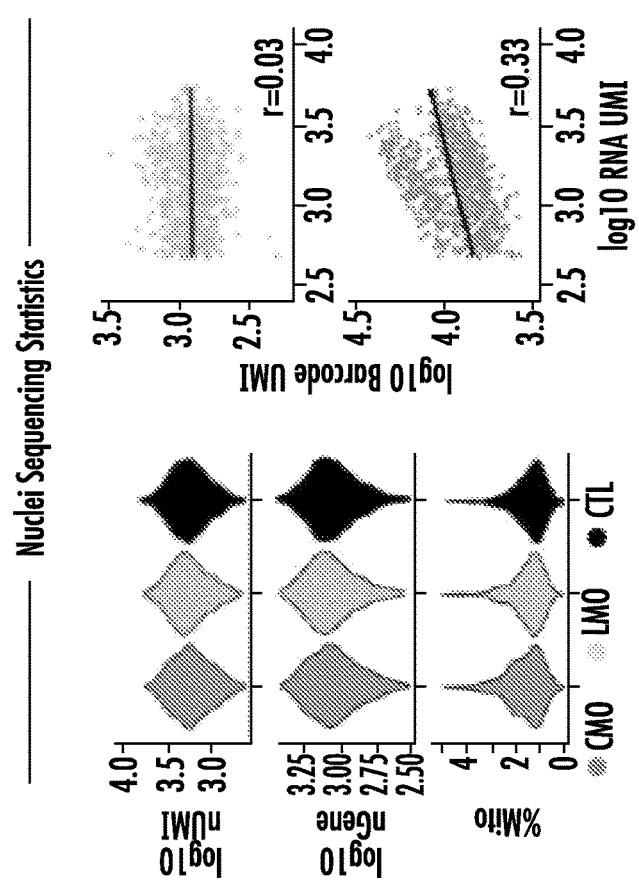
FIG. 12I shows the same analysis as described in FIG. 12D on snRNA-seq data. Unlike in live cells, gene expression neighborhoods for LMO- and CMO-labeled cells both mirror unlabeled cells, suggesting that both LMOs and CMOs enable nonperturbative single-nucleus RNA sequencing sample multiplexing. n=2,113 MEF nuclei.

Demultiplexing single nucleus RNA-seq (snRNA-seq) and time-course experiments: snRNA-seq is widely used for the analyses of solid tissues that are difficult to dissociate. We explored whether MULTI-seq could demultiplex snRNA-seq samples by purifying nuclei from HEKs and mouse embryonic fibroblasts (MEFs) and labeling each pool of nuclei with LMOs or CMOs prior to snRNA-seq. In parallel, we multiplexed Jurkat cells treated with ionomycin and phorbol 12-myristate 13-acetate (PMA) at eight time points (0-24 hours) to track T-cell activation dynamics (FIG. 12E). MULTI-seq sample classifications matched their intended cell type clusters in gene expression space (FIG. 12F, FIG. 12G) with a ~0.5% misclassification rate (FIG. 8F). Notably, MULTI-seq classifications were species-specific and predicted-85% of mouse-human doublets, which approximates the theoretical doublet detection limit of ~92%. Matching live-cell results, MULTI-seq barcoding did not impair mRNA capture (FIG. 12H). In contrast to live-cell results, both CMO- and LMO-labeled nuclei were transcriptionally indistinguishable from unbarcoded controls (FIG. 12I). Moreover, CMO-labeled nuclei had higher average signal-to-noise ratio (SNR) and total number of barcode UMIs relative to LMO-labeled nuclei (FIG. 21), consistent with previous flow cytometry results.

Upon demultiplexing individual time points along the trajectory of T-cell activation (FIG. 8G), we observed multiple literature-supported transcriptional dynamics (FIG. 8H). For example, genes undergoing early down-regulation (e.g., TSHR) and transient (e.g., DUSP2), sustained (e.g., CD69), and late (e.g., GRZA) up-regulation were readily identified in the data.

MULTI-seq identifies doublets in scRNA-seq data: We next sought to demonstrate MULTI-seq scalability by multiplexing 96 unique HMEC samples spanning a range of microenvironmental conditions. We exposed duplicate cultures consisting of MEPs, LEPs, and both cell types grown in M87A media without EGF to 15 physiologically-relevant signaling molecules or signaling molecule combinations (FIG. 13A). We barcoded each sample before pooling and loaded cells across three 10× microfluidics lanes, resulting in a 32-fold reduction in reagent use relative to standard practices.

Figure 9E:
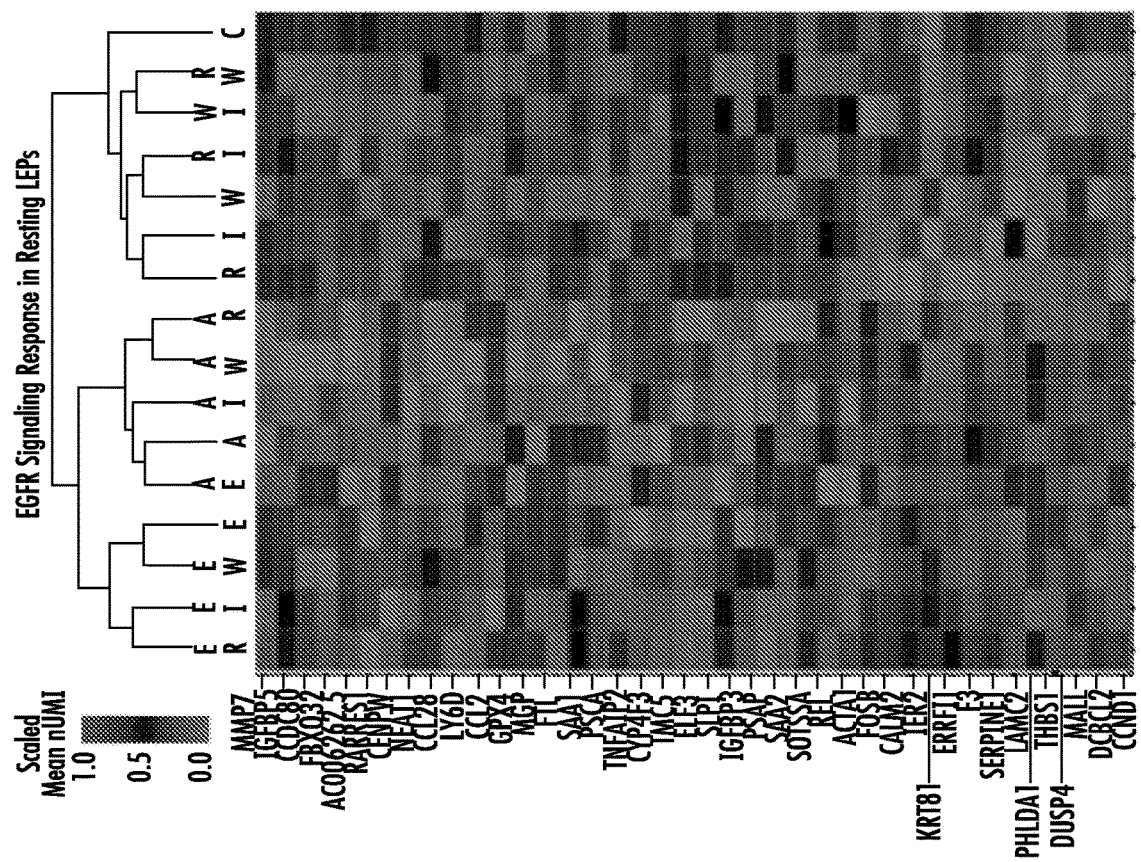
FIG. 9E shows a hierarchical clustering and heat map analysis of resting LEPs grouped by treatment. Emphasized genes are known EGFR signaling targets. RNA UMI abundances are scaled from 0-1 for each gene. Values correspond to the average expression within each signaling molecule treatment group. Dendrogram labels: E=EGF, W=WNT4, A=AREG, I=IGF-1, R=RANKL, C=Control.
Figure 14:
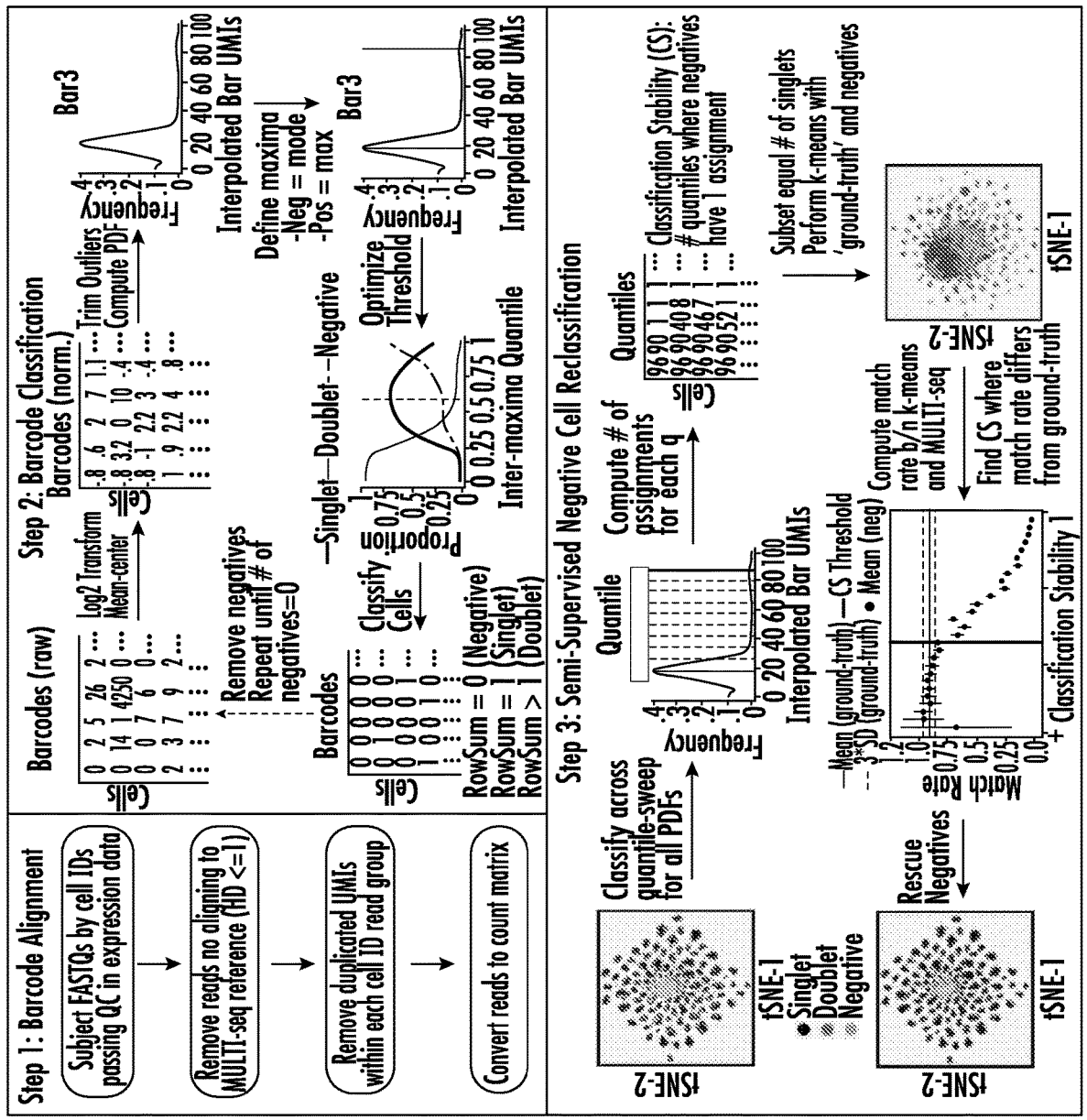
FIG. 14 shows results from the 96-plex HMEC experiment are used as representative examples for the barcode classification workflow. Results from the 96-plex technical replicate HMEC experiment as used as representative examples for the semi-supervised negative cell reclassification workflow. PDF=probability density function.

To classify HMECs into sample groups, we implemented a sample classification workflow inspired by previous strategies (Computational Methods, Supplemental Materials, FIG. 13) which identified 76 sample groups consisting of 26,439 total cells (FIG. 14). Each group was exclusively enriched for a single barcode (FIG. 9A, left, FIG. 13C) an average of ~199-fold above the most abundant off-target barcode (FIG. 13D). Unlike sample multiplexing data with relatively few samples, MULTI-seq-defined doublets localized to the peripheries of singlet clusters in barcode space for this experiment (FIG. 9A, right). We suspected missing barcodes resulted from handling errors (FIG. 13B, Supplemental Materials), as a technical replicate yielded all 96 sample groups (FIG. 13E-G).

To assess demultiplexing accuracy, we grouped MULTI-seq classifications according to cell type composition (e.g., MEPs alone, LEPs alone, or both) and visualized these groups in gene expression space. Unsupervised clustering and marker analysis of the resulting transcriptome data distinguished LEPs from MEPs along with a subset of ambiguous cells expressing markers for both cell types (FIG. 9B, left, FIG. 15A). MULTI-seq classifications matched their expected cell type clusters (FIG. 9B, right), while cells co-expressing MEP and LEP markers were predominantly defined as doublets. MULTI-seq identified doublets that were overlooked when predicting doublets using marker genes (FIG. 9B, arrow). Additionally, MULTI-seq doublet classifications generally agreed with computational predictions (FIG. 9C, Sensitivity=0.283 Specificity=0.965), with the exception of 'homotypic' doublets—i.e., doublets formed from transcriptionally-similar cells—to which computational doublet detection techniques are insensitive (Supplemental Materials). Moreover, DoubletFinder erroneously classified proliferative LEPs as doublets (FIG. 9C, arrow), illustrating how computational doublet inference performance suffers when applied to datasets with low cell type numbers.

Figure 9D:
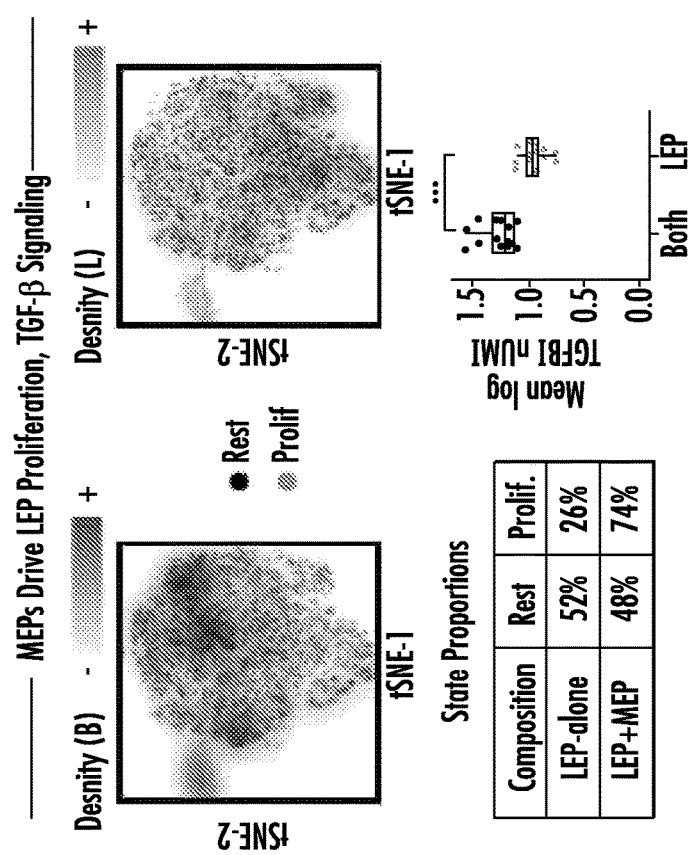
FIG. 9D shows MEP co-culture induces LEP proliferation and TGF-β signaling. Clusters corresponding to resting (black) and proliferative (green) LEPs are identifiable in gene expression space (FIG. 15B). Projecting sample classification densities onto gene expression space for co-cultured LEPs (dark red, top left) and LEPs cultured alone (blue, top right) illustrates that co-cultured LEPs are enriched in the proliferative state (table, bottom left). Co-cultured LEPs also express more TGFBI than LEPs cultured alone. Each point represents an average of LEPs grouped according growth factor condition. ***=Wilcoxon rank sum test (two-sided), p=3.1×10−6. n=32 signaling molecule condition groups. Data are represented as mean±SEM.

MULTI-seq identifies transcriptional responses to co-culture conditions and signaling molecules: Sample demultiplexing, doublet removal, and quality-control filtering resulted in a final scRNA-seq dataset including 21,753 total cells, revealing two transcriptional responses linked to culture composition. First, we observed that LEPs co-cultured with MEPs exhibited enriched proliferation relative to LEPs cultured alone (FIG. 9D, FIG. 15B). In contrast, MEPs were equally proliferative when cultured alone or with LEPs (FIG. 15C). Second, we observed that non-proliferative co-cultured MEPs and LEPs are enriched for TGFBI expression relative to MEPs and LEPs cultured alone (FIG. 9D, bottom right, FIG. 15D).

We next used hierarchical clustering to assess how LEPs or MEPs responded to signaling molecule exposure. HMECs exposed to the EGFR ligands AREG and EGF exhibited gene expression profiles that were significantly different from control cells. AREG- and EGF-stimulated LEPs expressed increased levels of EGFR signaling genes (e.g., DUSP4) and genes up-regulated in HER2+ breast cancers (e.g., PHLDA1, FIG. 9E) relative to control LEPs. AREG- and EGF-stimulated MEPs also express high levels of known EGFR-regulated genes (e.g., ANGPTL4, FIG. 15E).

MULTI-seq identifies low-RNA cells in cryopreserved, primary PDX samples: Using scRNA-seq to analyze archival primary tissue samples is often difficult because these samples can have low cell viability that is compounded during cryopreservation, thawing, enzymatic digestion, and scRNA-seq sample preparation. We investigated whether the rapid and non-perturbative nature of MULTI-seq barcoding would enable cryopreserved tissue multiplexing using samples dissected from a PDX mouse model of metastatic triple-negative breast cancer. In this model system, the diameter of primary tumors was used as a proxy for metastatic progression in the lung (FIG. 16A). We barcoded 9 distinct samples representing primary tumors and lungs from early- and mid-stage PDX mice (in duplicate), one late-stage PDX mouse, and a single lung from an immunodeficient mouse without tumors (FIG. 10A). We then pooled FACS-enriched populations of barcoded hCD298+ human metastases with mCD45+ mouse immune cells prior to "super-loading" a single 10× Genomics microfluidics lane.

Quality-control filtering, sample classification, and doublet removal resulted in a final scRNA-seq dataset of 9,110 mouse and human singlets spanning all 9 samples (FIG. 10B, FIG. 16B). Under the conditions tested, barcode SNR was largely invariant to inter-sample differences in total cell number and viability (FIG. 16C, FIG. 22). Classification accuracy was supported by tissue-specific gene expression patterns (FIG. 16D) and comparisons to FACS enrichment results (FIG. 16E). Additionally, MULTI-seq classifications identified high-quality single-cell transcriptomes that would have been discarded using standard quality-control workflows (e.g., CellRanger RNA UMI inflection point threshold=1350, FIG. 10C). When comparing cells with 100-1350 RNA UMIs, classified cells included immune cell types that are difficult to detect using single-cell and bulk transcriptomics (e.g., neutrophils). Strikingly, 90.8% of sequenced neutrophils would have been discarded by CellRanger. In contrast, unclassified low-RNA cells had poor-quality gene expression profiles predominantly corresponding to broken cells (FIG. 23).

Characterizing the lung immune response to metastatic progression: We next sought to describe how lung immune cells respond to metastatic progression. Beginning with a dataset comprised of 5,690 mCD45+ cells, we identified gene expression profiles associated with neutrophils, monocytes and macrophages (alveolar, interstitial, and (non)-classical monocytes), dendritic cells (mature, immature, Ccr7+, and plasmocytoid DCs), and endothelial cells (FIG. 10C, top, FIG. 16F). The use of immunodeficient PDX mice resulted in a lack of lymphocytes (e.g., T, B, and NK cells).

We observed literature-supported changes in immune cell proportions (FIG. 10D) and transcriptional state (FIG. 10E) at each tumor stage. For instance, neutrophils were enriched in early-stage PDX mice while alveolar macrophages were depleted over the course of metastasis. Moreover, stage-specific transcriptional heterogeneity among classical monocytes (CMs, FIG. 10F) reflects previous descriptions of lung CM state transitions in PDX breast cancer models.

Unsupervised clustering of CMs cleanly resolved cells from each tumor stage (FIG. 17G), enabling the identification of genes upregulated in CMs during metastatic progression (FIG. 24). Notably, clustering also revealed that CMs from late-stage PDX mice fell into two distinct transcriptional states discernible by Cd14 expression (FIG. 10F, inset, FIG. 25) matching previous observations. Genes that are differentially-expressed between CM subsets include genes known to influence metastatic progression (e.g., Thbs1, S100α8/9, and Wfdc21). To discern whether the results were primarily attributable to inter-mouse variability, we used Earth Mover's Distance (EMD) to quantify the magnitude of transcriptional dissimilarity between lung CMs from each mouse and tumor stage. These results illustrate that CMs from early- and mid-stage mouse replicates (scaled EMD=0.16) were more similar than CMs from distinct tumor stages (scaled EMD=0.69).

MULTI-seq is an ideal sample multiplexing approach because it is scalable, universal, and improves scRNA-seq data quality. MULTI-seq is scalable because it uses inexpensive reagents, involves minimal sample handling, and is rapid and modular in design. MULTI-seq modularity enables any number of samples to be multiplexed with a single pair of 'anchor' and 'co-anchor' LMOs. Moreover, since LMOs are quenchable with BSA and can be incorporated during proteolytic dissociation, we anticipate that further method optimization will facilitate wash-free sample preparation workflows. When integrated with automated liquid handling, these features position MULTI-seq as a powerful technology enabling 'screen-by-sequencing' applications (e.g., L1000, DRUG-seq) in multicellular systems (e.g., organoids, PBMCs, etc.).

In this study, we leveraged MULTI-seq scalability to perform a 96-plex HMEC perturbation assay, revealing noteworthy principles for future scRNA-seq sample multiplexing experiments. Specifically, we observed that responses to signaling molecules were less pronounced than responses linked to cellular composition. For instance, co-cultured MEPs and LEPs engage in TGF-β signaling that is absent in the associated monocultures. In contrast, MEPs and LEPs only exhibited pronounced transcriptional responses to the EGFR ligands AREG and EGF in these data, despite the established roles of all tested signaling molecules in mammary morphogenesis. We speculate that rich media formulations used to expand cells, such as the M87A media (-EGF) used here, likely buffer cells against microenvironmental perturbations. Thus, careful consideration of cell-type composition and media formulation will be essential to accurately interpret future scRNA-seq experiments.

Beyond its scalability, MULTI-seq improves scRNA-seq data quality in two distinct ways. First, MULTI-seq identifies doublets as cells associated with multiple sample indices. The ability to detect doublets allows for droplet-microfluidics devices to be "super-loaded", resulting in ~5-fold improvement in cellular throughput. Moreover, unlike computational doublet prediction methods, MULTI-seq detects homotypic doublets and performs well on scRNA-seq data with minimal cell-type complexity. However, since computational doublet detection methods detect doublets formed from cells with shared sample barcodes, doublet detection should ideally involve a synergy of computational and molecular approaches.

Second, MULTI-seq improves scRNA-seq data quality by 'rescuing' cells that would otherwise be discarded by quality-control workflows utilizing RNA UMI thresholds. Such workflows are systematically biased against cell types with low RNA content. MULTI-seq classifications provide an orthogonal metric to RNA UMIs for distinguishing low-RNA from low-quality cells. We leveraged this feature (described initially by Stoeckius et al) to improve the quality of the PDX dataset, where MULTI-seq classifications 'rescued' >90% of the sequenced neutrophils while avoiding misclassification of broken cells.

Finally, MULTI-seq is universally applicable to any sample including cells or nuclei with an accessible plasma membrane. As a result, we used the same set of MULTI-seq reagents to multiplex 15 distinct cell types or nuclei from both mice and humans. Notably, CMOs outperformed LMOs in nuclei isolation buffers containing BSA because BSA sequesters LMOs. Additionally, we anticipate that MULTI-seq is compatible with sample preservation strategies such as flash-freezing and fixation.

We leveraged all three of these features—scalability, universality, and data quality improvement—to multiplex cryopreserved primary tumors and lungs dissected from PDX mouse models at varying stages of metastatic progression. PDX sample multiplexing requires barcoding cells from (i) multiple species that may (ii) down-regulate surface epitopes commonly targeted by antibody-based multiplexing techniques (e.g., MHC—1), and (iii) have intrinsically-low viability requiring minimal sample handling. MULTI-seq successfully demultiplexed every sample, revealing novel and literature-supported immune cell responses to metastatic progression in the lung. For example, while metastasis-associated shifts in neutrophil, alveolar macrophage, and CM proportions were previously observed, we described significant shifts in interstitial macrophages, dendritic cells, and non-classical monocytes that, to our knowledge, are novel and require further experimental validation.

Moreover, we identified CM subsets that were discernible by Cd14 expression and genes with diverse effects on metastatic progression. Perplexingly, Cd14-high CMs expressing the pro-metastatic gene Thbs1 and CD14-low CMs expressing the anti-metastatic genes S100α8/9 and Wfdc21 coexisted in metastasized lungs. Since we isolated immune cells from the whole lung in this study, we could not discern whether CD14-high and CD14-low states were spatially correlated with metastatic sites. However, MULTI-seq could be employed to spatially barcode distinct regions of a single metastatic lung, enabling direct interrogation of CM spatial heterogeneity.

In summary, MULTI-seq broadly enables users to incorporate additional layers of information into scRNA-seq experiments. In the future, we anticipate that more diverse types of information will be targeted including spatial coordinates, time-points, species-of-origin, and sub-cellular structures (e.g., nuclei from multinucleated cells). We also anticipate that increasing LMO membrane residency time using alternative oligonucleotide conjugate designs may enable MULTI-seq applications for non-genetic lineage tracing and/or cellular competition assays.

Example 4—Split-Pool Barcoding and mRNA Capture with LMOs

Single-cell RNA-sequencing fundamentally requires mRNA molecules to be captured and tagged with both transcript-specific and cell-specific barcodes. Traditionally, this goal has been achieved by co-encapsulating individual cells with hydrogel beads bound to oligonucleotides with (i) a 5' PCR handle, (ii) a cell-specific barcode shared between all bead-bound oligos, (iii) a unique molecular identifier (UMI), and (iv) an oligo-dT poly-A mRNA capture sequence. However, bead-free scRNA-seq applications are highly desirable. Lipid-modified oligonucleotides (LMOs) form stable DNA scaffolds on the surface of live cells that can be leveraged to build barcoded mRNA capture sequences. Cell-specific barcodes are generated through a split-pool approach.

Referring to FIG. 28, single cell suspensions of samples are labeled with 0.5-5 µM LMO and a barcode oligo as previously described. Samples are then washed with 2% BSA in PBS, pooled, mixed, and divided up across many (e.g. 96 or 384) wells. Each well receives 0.5-5 µM of a second barcode containing a 5' phosphate and a linker oligo which hybridizes to the first and second barcodes to link them together. This process is repeated as many times as necessary for each cell to receive a unique set of barcodes with the final barcode always containing the capture sequence (e.g. oligo-dT). After barcoding rounds, the cells are pooled one last time and diluted to a concentration of 1000 cell per µL. Single cells are isolated in microfluidic droplets along with a buffer containing 80 mM Tris-HCl (pH 8.0-8.4), 2 U/µL RNase inhibitor, 20 U/µL T4 DNA ligase and 1× ligation buffer from NEB quick ligation kit, 0.1-0.5% Igepal CA-630 detergent for lysis, 1.0 mM dNTPs, 1.5 U/µL WarmStart RTx Reverse Transcriptase (RT) (NEB). After single cell isolation and lysis, the cells are kept on ice for ~30 minutes to allow the ligase to covalently link each barcode into a single strand. Then the mixture is heated to 55° C. to deactivate the ligase and activate the RT enzyme. After ~1 hr at 55° C., the emulsion is heated to 80° C. for 10 minutes, then cooled to room temperature. The emulsion is broken with 1 mL perfluorooctanol. At this point, the sample can be taken through any number of standard cDNA amplification and next-generation sequencing library preparation workflows.

Example 5— General Spatial Information within Tissue or Sample

LMOs can also be used to barcode cells based on the relative spatial orientation. There are, generally speaking, two approaches to achieving spatial barcoding: (1) physical separation cells/tissue regions followed by barcoding as described previously and; (2) addition of lipid-modified oligonucleotide anchors to cells followed by addition of spatially-defined barcode oligonucleotides. In first case, the physical separation can be achieved across a range of length scales through dissection with scalpel, microwell isolation, or laser-capture microdissection. Once cells are isolated, barcodes can be introduced to each unique sample indicating the relative location of the cells in that sample. In the second case, all cells receive anchor and co-anchor before addition of barcode oligonucleotides. The barcodes are specific to a location and diffuse from the location of introduction to be captured on cells via hybridization to the anchor strand. The relative locations of cells are determined by the amount and relative ratios of the spatial barcodes. Introduction of spatial barcodes can be achieved by several methods including microarrayres, inkjet printers, acoustic liquid handlers, and cleavage from a solid-support (e.g., array or beads).

Spatial Barcoding of the Developing Gut (Experimental and Data)

To apply MULTI-seq for mesoscale spatial barcoding of scRNA-seq samples, we first surgically-removed the small intestine from freshly-euthanized mice or from dissected embryos dissected. The small intestine was then stretched along a surface before connective tissue and fat was removed with a scalpel. The small intestine was then filleted prior to 4× washes with ice-cold PBS with shaking. After washing, each intestine was cut into equally-sized segments (i.e., ~1 cm in length along the proximal-distal axis for adult intestines; ~2.5 mm for developing intestine). Segments were then dissociated for 20 minutes at room temperature with shaking in 2 mL dissociation media (RPMI1640 with 3% FBS, 1% pen/strep, 1% sodium pyruvate, 1% MEM non-essential amino acids, 1% L-glutamine, 2.5% HEPES, 5 mM EDTA and 10 mM DTT).

Following dissociation and manual agitation with a p1000 pipette, the dissociation solution was strained through a 100 mM filter into 15 mL conical vial on ice. Tissue chunks remaining at the top of strainer were then transferred to a separate 15 mL conical vial containing 4 mL EDTA for further digestion (e.g., vigorous shaking for 30 seconds) prior to re-filtering. This process was repeated twice, generating a roughly-filtered cell suspension. This roughly-filtered suspension was then filtered through a 70 mM filter into a new 15 mL conical vial prior to centrifugation for 8 minutes at 1500 rpm.

Each cell suspension was then washed once with 10 mL ice-cold PBS prior to resuspension to a single-cell suspension in 160 mL in ice-cold PBS. Single-cell suspensions were then transferred to individual wells of a 48-well plate before adding 20 mL of 2.5 mM anchor LMO pre-hybridized to a single MULTI-seq sample barcode. Cell suspensions were then manually agitated and incubated on ice for 5 minutes prior to addition of 20 mL of 2.5 mM co-anchor LMO and a subsequent 5 minute incubation on ice. Following MULTI-seq labeling, labeling solutions were diluted with 300 mL with 5% BSA to quench ambient LMOs prior to pooling, antibody staining, and FACS enrichment for live cells. Live cells were then subjected to the standard 10× Genomics scRNA-seq workflow using droplet microfluidics. Schematics and data collected over each experiment is presented in FIG. 26 and FIG. 27.

The invention claimed is:

1. A composition comprising:
   (a) a first lipid-conjugated DNA oligonucleotide comprising a first lipid moiety, a first hybridization region, and a first primer region; and
   (b) a second DNA oligonucleotide comprising a second primer region, a barcode region, and a capture sequence, wherein the second primer region is the reverse complement of the first primer region.

2. The composition of claim 1, further comprising a third lipid-conjugated DNA oligonucleotide comprising a second hybridization region and a second lipid moiety, wherein the second hybridization region is the reverse complement of the first hybridization region.

3. The composition of claim 2, wherein:
   (a) the third lipid-conjugated DNA oligonucleotide comprises, in a 5' to 3' orientation, the second hybridization region and the second lipid moiety; or
   (b) the third lipid-conjugated DNA oligonucleotide comprises, in a 3' to 5' orientation, the second hybridization region and the second lipid moiety.

4. The composition of claim 2, wherein the first lipid moiety and the second lipid moiety comprise a fatty acid having from 12 to 28 carbons.

5. The composition of claim 2, wherein the second lipid moiety comprises a compound of Formula II:

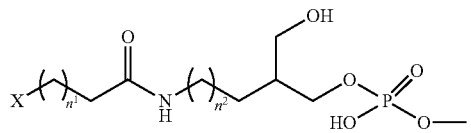

Formula II or a physiologically acceptable salt thereof,
wherein n1 is from 5 to 25, n 2 is from 0 to 24, and X is selected from the group consisting of NH, $CH_2$, O, and CH—R, wherein R is a C12 to C28 monoglyceride, alkenyl, alkyl, aryl, or aralkyl.

6. The composition of claim 2, wherein:
   (a) the first lipid-conjugated DNA oligonucleotide comprises a nucleic acid sequence having at least 70% sequence identity to the nucleic acid sequence of SEQ ID NO: 1;
   (b) the second oligonucleotide comprises a nucleic acid sequence having at least 70% sequence identity to the nucleic acid sequence of SEQ ID NO: 3; and/or
   (c) the third lipid-conjugated DNA oligonucleotide comprises a nucleic acid sequence having at least 70% sequence identity to the nucleic acid sequence of SEQ ID NO: 2.

7. The composition of claim 2, wherein one or more of the first lipid-conjugated DNA oligonucleotide, the second DNA oligonucleotide, and the third lipid-conjugated DNA oligonucleotide is bound to a solid support.

8. The composition of claim 7, wherein the solid support is a bead.

9. The composition of claim 1, wherein:
   (a) the first lipid-conjugated DNA oligonucleotide comprises, in a 5' to 3' orientation, the first lipid moiety, the first hybridization region, and the first primer region; or
   (b) the first lipid-conjugated DNA oligonucleotide comprises, in a 3' to 5' orientation, the first lipid moiety, the first hybridization region, and the first primer region;

(c) the second DNA oligonucleotide comprises, in a 5' to 3' orientation, the second primer region, the barcode region, and the capture sequence; or
   (d) the second DNA oligonucleotide comprises, in a 3' to 5' orientation, the second primer region, the barcode region, and the capture sequence.

10. The composition of claim 1, wherein the first lipid moiety comprises a compound of Formula I:

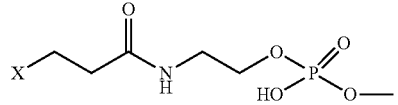

Formula I or a physiologically acceptable salt thereof,
wherein n 1 is from 5 to 25, n 2 is from 1 to 25, and X is selected from the group consisting of NH, $CH_2$, O, and CH—R, wherein R is a C12 to C28 monoglyceride, alkenyl, alkyl, aryl, or aralkyl.

11. The composition of claim 1, wherein the first lipid moiety comprises a lipid selected from lignoceric acid and cholesterol.

12. A method of quantifying mRNA levels in a sample, the method comprising:
   (a) adding two or more single cells from the sample to two or more vessels on a solid support comprising at least one surface, wherein each vessel comprises a single cell from the sample and is addressable from a point external to the solid support; and
   (b) contacting each of the single cells with the composition of claim 1 such that each cell comprises the composition, and each cell is independently addressable to measure differences in mRNA levels between the at least two cells.

13. The method of claim 12 further comprising reverse transcribing RNA in the cell to cDNA and amplifying the cDNA.

14. A method of diagnosing a disorder in a subject, the method comprising measuring expression of a marker gene in a sample obtained from the subject, wherein the measuring comprises contacting the sample with the composition of claim 1, and wherein an increase or decrease in expression of the marker gene from a predetermined level indicates that the subject is afflicted with the disorder.

15. The method of claim 14 wherein the measuring further comprises reverse transcribing RNA in the cell to cDNA and amplifying the cDNA.

16. The method of claim 14, wherein the disorder is lung cancer.

17. A method of labeling a cell, a method of isolating endogenous DNA from a single cell, or a method of sequencing nucleic acid sequences from a single cell comprises:
   (a) exposing the cell to one or a plurality of anchor-lipid modified oligonucleotides disclosed herein or the composition of claim 1 for a time period sufficient for the anchor-lipid modified oligonucleotide to embed itself within a cell membrane of the cell;
   (b) exposing the cell to one or a plurality of labeling oligonucleotides complementary to the anchor-lipid modified oligonucleotides for a time period sufficient for the anchor-lipid modified oligonucleotide to form a complementary strand of nucleic acid with the one or plurality of labeling oligonucleotides;

(c) ligating the one or plurality of labeling oligonucleotides to the one or plurality of anchor-lipid modified oligonucleotides; and, optionally (d) detecting the presence of the one or plurality of labeling oligonucleotides by detection of one of more unique nucleotide sequences corresponding to the one or plurality of labeling oligonucleotides; and/or (e) isolating the cell based upon the presence of the one or plurality of labeling oligonucleotides, wherein the presence of the one or plurality of labeling oligonucleotides is determined by detection of one of more unique nucleotide sequences corresponding to the one or plurality of labeling oligonucleotides.

18. A method of identifying a spatial position of a pattern of nucleic acid expression within a sample or tissue of a subject, the method comprising:

(a) partitioning one or a plurality of cells from the sample or the tissue corresponding to a region of the sample into one of a plurality of vessels;

(b) exposing the one or plurality of cells corresponding to a region of the sample with an known oligonucleotide disclosed herein for a time sufficient for incorporation of the known oligonucleotide into the one or plurality of cells, each oligonucleotide unique for and corresponding to one of the plurality of vessels into which the one or plurality of cells are exposed;

(c) isolating nucleic acid from the one or plurality of cells according to the known oligonucleotide;

(d) quantifying expression of nucleic acids and/or sequencing the nucleic acid from the one or plurality of cells;

(e) normalizing the expression of nucleic acid in an expression profile; and (f) correlating the expression profile from the one or plurality of cells to the spatial position of the cells within the sample, relative to the tissue, or within the tissue, wherein the known oligonucleotide disclosed herein in each of the plurality of vessels is independently selected from one or a combination of:

(x) a first lipid-conjugated DNA oligonucleotide comprising a first lipid moiety, a first hybridization region, and a first primer region; and/or (y) a second lipid-conjugated DNA oligonucleotide comprising a second hybridization region and a second lipid moiety, wherein the second hybridization region is the reverse complement of the first hybridization region; and/or (z) a third DNA oligonucleotide comprising from a second primer region, a barcode region, and a capture sequence, wherein the second primer region is the reverse complement of the first primer region.

\* \* \* \* \*